(12) United States Patent
Boudreaux et al.

(10) Patent No.: US 10,136,938 B2
(45) Date of Patent: Nov. 27, 2018

(54) ELECTROSURGICAL INSTRUMENT WITH SENSOR

(71) Applicant: Ethicon Endo-Surgery, Inc., Cincinnati, OH (US)

(72) Inventors: Chad P. Boudreaux, Cincinnati, OH (US); John M. Sarley, Mason, OH (US); Mark A. Davison, Mason, OH (US); Catherine A. Corbett, Cincinnati, OH (US); Jeff K. Bargemann, Morrow, OH (US)

(73) Assignee: Ethicon LLC, Guaynabo, PR (US)

( * ) Notice: Subject to any disclaimer, the term of this patent is extended or adjusted under 35 U.S.C. 154(b) by 861 days.

(21) Appl. No.: 14/526,974

(22) Filed: Oct. 29, 2014

(65) Prior Publication Data

US 2016/0120601 A1    May 5, 2016

(51) Int. Cl.
*A61B 18/18*    (2006.01)
*A61B 18/14*    (2006.01)
*A61B 17/00*    (2006.01)
*A61B 18/00*    (2006.01)
(Continued)

(52) U.S. Cl.
CPC ............ *A61B 18/1445* (2013.01); *A61B 2017/00075* (2013.01); *A61B 2017/2916* (2013.01); *A61B 2017/2923* (2013.01); *A61B 2018/00708* (2013.01); *A61B 2018/00875* (2013.01); *A61B 2018/00892* (2013.01); *A61B 2018/00922* (2013.01); *A61B 2018/00928* (2013.01); *A61B 2018/00946* (2013.01);
(Continued)

(58) Field of Classification Search
USPC .......................................................... 606/51
See application file for complete search history.

(56) References Cited

U.S. PATENT DOCUMENTS

| 1,754,806 A | 4/1930 | Stevenson |
| 3,297,192 A | 1/1967 | Swett |
| 3,419,198 A | 12/1968 | Pettersen |

(Continued)

FOREIGN PATENT DOCUMENTS

| CN | 101819334 A | 9/2010 |
| DE | 102008051866 | 10/2010 |

(Continued)

OTHER PUBLICATIONS

U.S. Appl. No. 61/410,603, filed Nov. 5, 2010.

(Continued)

*Primary Examiner* — Nicole F Johnson
(74) *Attorney, Agent, or Firm* — Frost Brown Todd LLC

(57) ABSTRACT

An apparatus comprises a body, a shaft, an end effector and a sensor. The shaft extends distally from the body. The end effector is configured to receive energy from an energy source. The end effector comprises a first jaw and a second jaw. The second jaw is pivotable relative to the first jaw to transition the end effector from an open configuration to a closed configuration. In the closed configuration, the first jaw and second jaw define a closure gap. The sensor is operable to detect when the end effector is in the closed configuration. The sensor is also in communication with the energy source, such that the sensor is operable to communicate a signal to the energy source when the sensor detects the end effector in the closed configuration.

20 Claims, 32 Drawing Sheets

(51) Int. Cl.
 *A61B 90/00* (2016.01)
 *A61B 17/29* (2006.01)
(52) U.S. Cl.
 CPC .............. *A61B 2018/00952* (2013.01); *A61B 2018/1455* (2013.01); *A61B 2090/0811* (2016.02)

(56) References Cited

U.S. PATENT DOCUMENTS

| | | | |
|---|---|---|---|
| 3,619,671 A | 11/1971 | Shoh | |
| 4,034,762 A | 7/1977 | Cosens et al. | |
| 4,057,220 A | 11/1977 | Kudlacek | |
| 4,535,773 A | 8/1985 | Yoon | |
| 4,641,076 A | 2/1987 | Linden et al. | |
| 4,662,068 A | 5/1987 | Polonsky | |
| 4,666,037 A | 5/1987 | Weissman | |
| 4,685,459 A | 8/1987 | Koch et al. | |
| 4,717,018 A | 1/1988 | Sacherer et al. | |
| 4,717,050 A | 1/1988 | Wright | |
| 4,721,097 A | 1/1988 | D'Amelio | |
| 4,768,969 A | 9/1988 | Bauer et al. | |
| 4,800,878 A | 1/1989 | Cartmell | |
| 4,805,823 A | 2/1989 | Rothfuss | |
| 4,844,259 A | 7/1989 | Glowczewskie, Jr. | |
| 4,878,493 A | 11/1989 | Pasternak et al. | |
| 5,071,417 A | 12/1991 | Sinofsky | |
| 5,107,155 A | 4/1992 | Yamaguchi | |
| 5,144,771 A | 9/1992 | Miwa | |
| 5,169,733 A | 12/1992 | Savovic et al. | |
| 5,176,677 A | 1/1993 | Wuchinich | |
| 5,246,109 A | 9/1993 | Markle et al. | |
| 5,273,177 A | 12/1993 | Campbell | |
| 5,277,694 A | 1/1994 | Leysieffer et al. | |
| 5,308,358 A | 5/1994 | Bond et al. | |
| 5,322,055 A | 6/1994 | Davison | |
| 5,339,799 A | 8/1994 | Kami et al. | |
| 5,358,508 A | 10/1994 | Cobb et al. | |
| 5,361,902 A | 11/1994 | Abidin et al. | |
| 5,415,334 A | 5/1995 | Williamson, IV et al. | |
| 5,429,229 A | 7/1995 | Chester et al. | |
| 5,449,370 A | 9/1995 | Vaitekumas | |
| 5,454,378 A | 10/1995 | Palmer et al. | |
| 5,465,895 A | 11/1995 | Knodel et al. | |
| 5,501,607 A | 3/1996 | Yoshioka et al. | |
| 5,507,297 A | 4/1996 | Slater et al. | |
| 5,561,881 A | 10/1996 | Klinger et al. | |
| 5,578,052 A | 11/1996 | Koros et al. | |
| 5,580,258 A | 12/1996 | Wakata | |
| 5,582,617 A | 12/1996 | Klieman et al. | |
| 5,590,778 A | 1/1997 | Dutchik | |
| 5,592,065 A | 1/1997 | Oglesbee et al. | |
| 5,597,107 A | 1/1997 | Knodel et al. | |
| 5,599,350 A | 2/1997 | Schulze et al. | |
| 5,630,420 A | 5/1997 | Vaitekunas | |
| 5,630,456 A | 5/1997 | Hugo et al. | |
| 5,632,432 A | 5/1997 | Schulze et al. | |
| 5,673,840 A | 10/1997 | Schulze et al. | |
| 5,690,222 A | 11/1997 | Peters | |
| 5,704,534 A | 1/1998 | Huitema et al. | |
| 5,707,369 A | 1/1998 | Vaitekunas et al. | |
| 5,741,305 A | 4/1998 | Vincent et al. | |
| 5,776,155 A | 7/1998 | Beaupre et al. | |
| 5,800,336 A | 9/1998 | Ball et al. | |
| 5,814,055 A | 9/1998 | Knodel et al. | |
| 5,817,128 A | 10/1998 | Storz | |
| 5,868,244 A | 2/1999 | Ivanov et al. | |
| 5,873,873 A | 2/1999 | Smith et al. | |
| 5,882,310 A | 3/1999 | Marian, Jr. | |
| 5,935,144 A | 8/1999 | Estabrook | |
| 5,938,633 A | 8/1999 | Beupre | |
| 5,944,737 A | 8/1999 | Tsonton et al. | |
| 5,951,575 A | 9/1999 | Bolduc et al. | |
| 5,980,510 A | 11/1999 | Tsonton et al. | |
| 5,997,531 A | 12/1999 | Loeb et al. | |
| 6,018,227 A | 1/2000 | Kumar et al. | |
| 6,051,010 A | 4/2000 | Dimatteo et al. | |
| 6,056,735 A | 5/2000 | Okada et al. | |
| 6,063,098 A | 5/2000 | Houser et al. | |
| 6,066,151 A | 5/2000 | Miyawaki et al. | |
| 6,083,191 A | 7/2000 | Rose | |
| 6,083,223 A | 7/2000 | Baker | |
| 6,099,537 A | 8/2000 | Sugai et al. | |
| 6,113,593 A | 9/2000 | Tu et al. | |
| 6,123,702 A | 9/2000 | Swanson et al. | |
| 6,147,480 A | 11/2000 | Osadchy et al. | |
| 6,165,191 A | 12/2000 | Shibata et al. | |
| 6,190,386 B1 | 2/2001 | Rydell | |
| 6,204,592 B1 | 3/2001 | Hur | |
| 6,214,023 B1 | 4/2001 | Whipple et al. | |
| 6,246,896 B1 | 6/2001 | Dumoulin et al. | |
| 6,248,238 B1 | 6/2001 | Burtin et al. | |
| 6,287,304 B1 | 9/2001 | Eggers et al. | |
| 6,325,811 B1 | 12/2001 | Messerly | |
| 6,339,368 B1 | 1/2002 | Leith | |
| 6,398,755 B1 | 6/2002 | Belef et al. | |
| 6,409,742 B1 | 6/2002 | Fulton, III et al. | |
| 6,500,176 B1 | 12/2002 | Truckai et al. | |
| 6,500,188 B2 | 12/2002 | Harper et al. | |
| 6,512,667 B2 | 1/2003 | Shiue et al. | |
| 6,514,267 B2 | 2/2003 | Jewett | |
| 6,520,185 B1 | 2/2003 | Bommannan et al. | |
| 6,561,983 B2 | 5/2003 | Cronin et al. | |
| 6,562,032 B1 | 5/2003 | Ellman et al. | |
| 6,609,414 B2 | 8/2003 | Mayer et al. | |
| 6,622,731 B2 | 9/2003 | Daniel et al. | |
| 6,623,500 B1 | 9/2003 | Cook et al. | |
| 6,626,901 B1 | 9/2003 | Treat et al. | |
| 6,647,281 B2 | 11/2003 | Morency | |
| 6,650,091 B1 | 11/2003 | Shiue et al. | |
| 6,650,975 B2 | 11/2003 | Ruffner | |
| 6,656,177 B2 | 12/2003 | Truckai et al. | |
| 6,658,301 B2 | 12/2003 | Loeb et al. | |
| 6,666,875 B1 | 12/2003 | Sakurai et al. | |
| 6,669,690 B1 | 12/2003 | Okada et al. | |
| 6,717,193 B2 | 4/2004 | Olewine et al. | |
| 6,730,042 B2 | 5/2004 | Fulton et al. | |
| 6,753,673 B2 | 6/2004 | Shiue et al. | |
| 6,758,855 B2 | 7/2004 | Fulton, III et al. | |
| 6,761,698 B2 | 7/2004 | Shibata et al. | |
| 6,761,701 B2 | 7/2004 | Cucin | |
| 6,783,524 B2 | 8/2004 | Anderson et al. | |
| 6,815,206 B2 | 11/2004 | Lin et al. | |
| 6,821,671 B2 | 11/2004 | Hinton et al. | |
| 6,836,097 B2 | 12/2004 | Turner et al. | |
| 6,838,862 B2 | 1/2005 | Luu | |
| 6,847,192 B2 | 1/2005 | Turner et al. | |
| 6,860,880 B2 | 3/2005 | Treat et al. | |
| 6,869,435 B2 | 3/2005 | Blake | |
| 6,923,807 B2 | 8/2005 | Ryan et al. | |
| 6,978,921 B2 | 12/2005 | Shelton, IV et al. | |
| 6,982,696 B1 | 1/2006 | Shahoian | |
| 6,998,822 B2 | 2/2006 | Turner et al. | |
| 7,000,818 B2 | 2/2006 | Shelton, IV et al. | |
| 7,031,155 B2 | 4/2006 | Sauciuc et al. | |
| 7,061,749 B2 | 6/2006 | Liu et al. | |
| 7,077,853 B2 | 7/2006 | Kramer et al. | |
| 7,083,589 B2 | 8/2006 | Banko et al. | |
| 7,085,123 B2 | 8/2006 | Shiue et al. | |
| 7,101,371 B2 | 9/2006 | Dycus et al. | |
| 7,112,201 B2 | 9/2006 | Truckai et al. | |
| 7,125,409 B2 | 10/2006 | Truckai et al. | |
| 7,143,923 B2 | 12/2006 | Shelton, IV et al. | |
| 7,150,712 B2 | 12/2006 | Buehlmann et al. | |
| 7,169,146 B2 | 1/2007 | Truckai et al. | |
| 7,186,253 B2 | 3/2007 | Truckai et al. | |
| 7,186,473 B2 | 3/2007 | Shiue et al. | |
| 7,189,233 B2 | 3/2007 | Truckai et al. | |
| 7,220,951 B2 | 5/2007 | Truckai et al. | |
| 7,221,216 B2 | 5/2007 | Nguyen | |
| 7,232,440 B2 | 6/2007 | Dumbauld et al. | |
| 7,244,024 B2 | 7/2007 | Biscardi | |
| 7,292,227 B2 | 11/2007 | Fukumoto et al. | |
| 7,296,804 B2 | 11/2007 | Lechot et al. | |
| 7,303,108 B2 | 12/2007 | Shelton, IV | |

(56) References Cited

U.S. PATENT DOCUMENTS

| | | |
|---|---|---|
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckai et al. |
| 7,364,061 B2 | 4/2008 | Swayze et al. |
| 7,364,554 B2 | 4/2008 | Bolze et al. |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,404,508 B2 | 7/2008 | Smith et al. |
| 7,416,101 B2 | 8/2008 | Shelton, IV et al. |
| 7,422,139 B2 | 9/2008 | Shelton, IV et al. |
| 7,434,715 B2 | 10/2008 | Shelton, IV et al. |
| 7,464,846 B2 | 12/2008 | Shelton, IV et al. |
| 7,473,145 B2 | 1/2009 | Ehr et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,560,903 B2 | 7/2009 | Thrap |
| 7,563,142 B1 | 7/2009 | Wenger et al. |
| 7,573,151 B2 | 8/2009 | Acena et al. |
| 7,583,564 B2 | 9/2009 | Ketahara et al. |
| 7,628,791 B2 | 12/2009 | Garrison et al. |
| 7,638,958 B2 | 12/2009 | Philipp et al. |
| 7,643,378 B2 | 1/2010 | Genosar |
| 7,658,247 B2 | 2/2010 | Carter |
| 7,692,411 B2 | 4/2010 | Trainor et al. |
| 7,717,312 B2 | 5/2010 | Beetel |
| 7,721,930 B2 | 5/2010 | McKenna et al. |
| 7,721,936 B2 | 5/2010 | Shelton, IV et al. |
| 7,738,971 B2 | 6/2010 | Swayze et al. |
| 7,761,198 B2 | 7/2010 | Bhardwaj |
| 7,766,910 B2 | 8/2010 | Hixson et al. |
| 7,766,929 B2 | 8/2010 | Masuda |
| 7,770,722 B2 | 8/2010 | Donahoe et al. |
| 7,770,775 B2 | 8/2010 | Shelton et al. |
| 7,776,037 B2 | 8/2010 | Odom |
| 7,780,660 B2 | 8/2010 | Bourne et al. |
| 7,802,121 B1 | 9/2010 | Zansky et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,889,489 B2 | 2/2011 | Richardson et al. |
| 7,913,891 B2 | 3/2011 | Doll et al. |
| 7,922,063 B2 | 4/2011 | Zemlok et al. |
| 7,923,151 B2 | 4/2011 | Lam et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 7,977,921 B2 | 7/2011 | Bahai et al. |
| 7,982,439 B2 | 7/2011 | Trainor et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,083,120 B2 | 12/2011 | Shelton et al. |
| 8,097,011 B2 | 1/2012 | Hideo et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,642 B2 | 8/2012 | Houser et al. |
| 8,251,994 B2 | 8/2012 | McKenna et al. |
| 8,267,094 B2 | 9/2012 | Danek et al. |
| 8,277,446 B2 | 10/2012 | Heard |
| 8,292,882 B2 | 10/2012 | Danek et al. |
| 8,292,888 B2 | 10/2012 | Whitman |
| 8,298,253 B2 | 10/2012 | Charles |
| 8,301,262 B2 | 10/2012 | Mi et al. |
| 8,328,802 B2 | 12/2012 | Deville et al. |
| 8,333,764 B2 | 12/2012 | Francischelli et al. |
| 8,336,725 B2 | 12/2012 | Ramsey et al. |
| 8,337,097 B2 | 12/2012 | Cao |
| 8,344,690 B2 | 1/2013 | Smith et al. |
| 8,372,099 B2 | 2/2013 | Deville et al. |
| 8,377,059 B2 | 2/2013 | Deville et al. |
| 8,400,108 B2 | 3/2013 | Powell et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,408,439 B2 | 4/2013 | Huang et al. |
| 8,419,757 B2 | 4/2013 | Smith et al. |
| 8,419,758 B2 | 4/2013 | Smith et al. |
| 8,425,545 B2 | 4/2013 | Smith et al. |
| 8,444,653 B2 | 5/2013 | Nycz et al. |
| 8,444,662 B2 | 5/2013 | Palmer et al. |
| 8,449,529 B2 | 5/2013 | Bek et al. |
| 8,453,914 B2 | 6/2013 | Laurent et al. |
| 8,461,744 B2 | 6/2013 | Weiner et al. |
| 8,487,487 B2 | 7/2013 | Dietz et al. |
| 8,550,106 B2 | 10/2013 | Hebach et al. |
| 8,550,981 B2 | 10/2013 | Woodruff et al. |
| 8,551,088 B2 | 10/2013 | Falkenstein et al. |
| 8,564,242 B2 | 10/2013 | Hansford et al. |
| 8,573,461 B2 | 11/2013 | Shelton et al. |
| 8,602,287 B2 | 12/2013 | Yates et al. |
| 8,608,045 B2 | 12/2013 | Smith et al. |
| 8,617,077 B2 | 12/2013 | van Groningen et al. |
| 8,622,274 B2 | 1/2014 | Yates et al. |
| 8,623,027 B2 | 1/2014 | Price et al. |
| 8,632,535 B2 | 1/2014 | Shelton, IV et al. |
| 8,641,629 B2 | 2/2014 | Kurokawa |
| 8,657,174 B2 | 2/2014 | Yates et al. |
| 8,663,112 B2 | 3/2014 | Slayton et al. |
| 8,733,614 B2 | 5/2014 | Ross et al. |
| 8,758,342 B2 | 6/2014 | Bales et al. |
| 8,784,415 B2 | 7/2014 | Malackowski et al. |
| 8,808,319 B2 | 8/2014 | Houser et al. |
| 8,834,465 B2 | 9/2014 | Ramstein et al. |
| 8,864,761 B2 | 10/2014 | Johnson et al. |
| 8,906,017 B2 | 12/2014 | Rioux et al. |
| 8,926,610 B2 | 1/2015 | Hafner et al. |
| 8,961,441 B2 | 2/2015 | Cioanta et al. |
| 8,968,648 B2 | 3/2015 | Kaneko et al. |
| 8,998,939 B2 | 4/2015 | Price et al. |
| 9,000,720 B2 | 4/2015 | Stulen et al. |
| 9,011,336 B2 | 4/2015 | Slayton et al. |
| 9,011,427 B2 | 4/2015 | Price et al. |
| 9,011,471 B2 | 4/2015 | Timm et al. |
| 9,017,849 B2 | 4/2015 | Stulen et al. |
| 9,017,851 B2 | 4/2015 | Felder et al. |
| 9,023,071 B2 | 5/2015 | Miller et al. |
| 9,039,720 B2 | 5/2015 | Madan |
| 9,044,261 B2 | 6/2015 | Houser |
| 9,050,125 B2 | 6/2015 | Boudreaux et al. |
| 9,060,750 B2 | 6/2015 | Lam |
| 9,072,523 B2 | 7/2015 | Houser et al. |
| 9,078,671 B2 | 7/2015 | Beale |
| 9,089,338 B2 | 7/2015 | Smith et al. |
| 9,095,346 B2 | 8/2015 | Houser et al. |
| 9,113,903 B2 | 8/2015 | Unger |
| 9,179,912 B2 | 11/2015 | Yates et al. |
| 9,186,046 B2 | 11/2015 | Ramamurthy et al. |
| 9,186,047 B2 | 11/2015 | Ramamurthy et al. |
| 9,194,428 B2 | 11/2015 | Houser et al. |
| 9,247,986 B2 | 2/2016 | Haberstich et al. |
| 9,308,009 B2 | 4/2016 | Madan et al. |
| 9,318,271 B2 | 4/2016 | Fletcher et al. |
| 9,364,279 B2 | 6/2016 | Houser et al. |
| 9,364,288 B2 | 6/2016 | Smith et al. |
| 9,375,255 B2 | 6/2016 | Houser et al. |
| 9,375,258 B2 | 6/2016 | Kendrick |
| 9,381,058 B2 | 7/2016 | Houser et al. |
| 9,421,062 B2 | 8/2016 | Houser et al. |
| 9,441,954 B2 | 9/2016 | Ramamurthy et al. |

(56) References Cited

U.S. PATENT DOCUMENTS

| | | |
|---|---|---|
| 9,500,472 B2 | 11/2016 | Ramamurthy et al. |
| 9,500,473 B2 | 11/2016 | Ramamurthy et al. |
| 9,510,895 B2 | 12/2016 | Houser et al. |
| 9,526,565 B2 | 12/2016 | Strobl |
| 9,526,921 B2 | 12/2016 | Kimball et al. |
| 9,597,143 B2 | 3/2017 | Madan et al. |
| 9,622,832 B2 | 4/2017 | Birkenbach et al. |
| 9,629,652 B2 | 4/2017 | Mumaw et al. |
| 9,649,150 B2 | 5/2017 | Houser et al. |
| 9,675,375 B2 | 6/2017 | Houser et al. |
| 2001/0032666 A1 | 10/2001 | Jenson et al. |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2003/0144680 A1 | 7/2003 | Kellogg et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton et al. |
| 2005/0171522 A1 | 8/2005 | Christopherson |
| 2006/0030797 A1 | 2/2006 | Zhou et al. |
| 2006/0079829 A1 | 4/2006 | Fulton et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0078484 A1 | 4/2007 | Talarico et al. |
| 2007/0103437 A1 | 5/2007 | Rosenberg |
| 2007/0106297 A1* | 5/2007 | Dumbauld ......... A61B 18/1445 606/51 |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0228104 A1 | 9/2008 | Uber, III et al. |
| 2008/0255413 A1 | 10/2008 | Zemlok et al. |
| 2008/0281301 A1 | 11/2008 | Deboer et al. |
| 2008/0315829 A1 | 12/2008 | Jones et al. |
| 2009/0076506 A1 | 3/2009 | Baker |
| 2009/0096430 A1 | 4/2009 | Van Der Linde et al. |
| 2009/0143799 A1 | 6/2009 | Smith et al. |
| 2009/0143800 A1 | 6/2009 | Deville et al. |
| 2009/0253030 A1 | 10/2009 | Kooij |
| 2009/0281430 A1 | 11/2009 | Wilder |
| 2010/0021022 A1 | 1/2010 | Pittel et al. |
| 2010/0030218 A1 | 2/2010 | Prevost |
| 2010/0060231 A1 | 3/2010 | Trainor et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Alexander et al. |
| 2010/0249665 A1 | 9/2010 | Roche |
| 2010/0268221 A1 | 10/2010 | Beller et al. |
| 2010/0274160 A1 | 10/2010 | Yachi et al. |
| 2011/0009694 A1 | 1/2011 | Schultz et al. |
| 2011/0074336 A1 | 3/2011 | Miller |
| 2011/0077514 A1 | 3/2011 | Ulric et al. |
| 2011/0080134 A1 | 4/2011 | Miller |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087218 A1 | 4/2011 | Boudreaux et al. |
| 2011/0221398 A1 | 9/2011 | Ferber |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0111591 A1 | 5/2012 | Shelton, IV et al. |
| 2012/0116260 A1 | 5/2012 | Johnson et al. |
| 2012/0116261 A1 | 5/2012 | Mumaw et al. |
| 2012/0116262 A1 | 5/2012 | Houser et al. |
| 2012/0116263 A1 | 5/2012 | Houser et al. |
| 2012/0116265 A1 | 5/2012 | Houser et al. |
| 2012/0116266 A1 | 5/2012 | Houser et al. |
| 2012/0116379 A1 | 5/2012 | Yates et al. |
| 2012/0116381 A1 | 5/2012 | Houser et al. |
| 2012/0116391 A1 | 5/2012 | Houser et al. |
| 2012/0179036 A1 | 7/2012 | Patrick et al. |
| 2012/0292367 A1 | 11/2012 | Morgan et al. |
| 2012/0305427 A1 | 12/2012 | Felder et al. |
| 2013/0023868 A1 | 1/2013 | Worrell et al. |
| 2013/0030428 A1 | 1/2013 | Worrell et al. |
| 2013/0085330 A1 | 4/2013 | Ramamurthy et al. |
| 2013/0090528 A1 | 4/2013 | Ramamurthy et al. |
| 2013/0118733 A1 | 5/2013 | Kumar |
| 2014/0088379 A1 | 3/2014 | Bhamra et al. |
| 2014/0257284 A1 | 9/2014 | Artale |
| 2014/0263565 A1* | 9/2014 | Lytle, IV ............. A61B 17/068 227/180.1 |

FOREIGN PATENT DOCUMENTS

| | | |
|---|---|---|
| DE | 102009013034 | 10/2010 |
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1 728 475 A2 | 12/2006 |
| EP | 1743592 A1 | 1/2007 |
| EP | 1818021 A1 | 8/2007 |
| EP | 1839599 A1 | 10/2007 |
| EP | 1868275 A2 | 12/2007 |
| EP | 1886637 A1 | 2/2008 |
| EP | 1943976 A2 | 7/2008 |
| EP | 1970014 A1 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| EP | 2 772 210 A2 | 9/2014 |
| GB | 2425874 | 11/2006 |
| GB | 2440566 A | 2/2008 |
| JP | 2000-210301 A | 8/2000 |
| JP | 3989121 B | 10/2000 |
| JP | 4145069 B | 10/2003 |
| WO | WO 1997/024072 | 7/1997 |
| WO | WO 2000/065682 | 2/2000 |
| WO | WO 2003/013374 | 2/2003 |
| WO | WO 2003/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/090025 | 8/2007 |
| WO | WO 2007/137115 | 11/2007 |
| WO | WO 2007/137304 | 11/2007 |

(56) References Cited

FOREIGN PATENT DOCUMENTS

| WO | WO 2008/071898 | 6/2008 |
|---|---|---|
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |
| WO | WO 2012/009431 A2 | 1/2012 |

OTHER PUBLICATIONS

U.S. Appl. No. 61/550,768, filed Oct. 24, 2011.
Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic Battery System," Stryker (2006) pp. 1-2.
Australian First Examination Report dated May 18, 2015 for Application No. AU 2011323284.
Australian First Examination Report dated Jun. 17, 2015 for Application No. AU 2011323279.
Chinese First Office Action dated Jan. 29, 2015 for Application No. CN 2011800638159.
Chinese First Office Action dated Mar. 4, 2015 for Application No. CN 201180063595X.
Chinese First Office Action dated Mar. 27, 2015 for Application No. CN 2011800638214.
Chinese First Office Action dated Jul. 1, 2015 for Application No. CN 201180063986.1.
Chinese Second Office Action dated Aug. 4, 2015 for Application No. CN 2011800641486.
EP Communication dated Feb. 19, 2014 for Application No. EP 11781972.2.
International Search Report dated Jan. 12, 2012 for Application No. PCT/US2011/059226.
International Preliminary Report on Patentability dated May 7, 2013 for Application No. PCT/US2011/059226.
International Search Report dated Jan. 26, 2012 for Application No. PCT/US2011/059220.
International Preliminary Report on Patentability dated May 7, 2013 for Application No. PCT/US2011/059220.
International Search Report dated Feb. 1, 2012 for Application No. PCT/US2011/059223.
International Preliminary Report on Patentability dated Feb. 1, 2012 for Application No. PCT/US2011/059223.
International Search Report dated Feb. 2, 2012 for Application No. PCT/US2011/059354.
International Preliminary Report on Patentability dated May 7, 2013 for Application No. PCT/US2011/059354.
International Search Report dated Feb. 7, 2012 for Application No. PCT/US2011/059351.
International Preliminary Report on Patentability dated May 7, 2013 for Application No. PCT/US2011/059351.
International Search Report dated Feb. 13, 2012 for Application No. PCT/US2011/059217.
International Preliminary Report on Patentability dated May 7, 2013 for Application No. PCT/US2011/059217.
International Search Report dated Feb. 23, 2012 for Application No. PCT/US2011/059371.
International Preliminary Report on Patentability dated May 7, 2013 for Application No. PCT/US2011/059371.
International Search Report dated Mar. 15, 2012 for Application No. PCT/US2011/059338.
International Preliminary Report on Patentability dated May 7, 2013 for Application No. PCT/US2011/059338.
International Search Report dated Mar. 22, 2012 for Application No. PCT/US2011/059362.
International Preliminary Report on Patentability dated May 7, 2013 for Application No. PCT/US2011/059362.
International Search Report dated Apr. 4, 2012 for Application No. PCT/US2011/059215.
International Preliminary Report on Patentability dated May 8, 2013 for Application No. PCT/US2011/059215.
International Search Report dated Apr. 18, 2012 for Application No. PCT/US2011/059222.
International Preliminary Report on Patentability dated May 7, 2013 for Application No. PCT/US2011/059222.
International Search Report dated May 24, 2012 for Application No. PCT/US2011/059378.
International Preliminary Report on Patentability dated May 7, 2013 for Application No. PCT/US2011/059378.
International Search Report dated May 29, 2012 for Application No. PCT/US2011/059358.
International Preliminary Report on Patentability dated May 7, 2013 for Application No. PCT/US2011/059358.
International Search Report dated Jun. 4, 2012 for Application No. PCT/US2011/059365.
International Preliminary Report on Patentability dated May 8, 2013 for Application No. PCT/US2011/059365.
International Search Report dated Jun. 12, 2012 for Application No. PCT/US2011/059218.
International Preliminary Report on Patentability dated May 7, 2013 for Application No. PCY/US2011/059218.
International Search Report dated Apr. 11, 2012 for Application No. PCT/US2011/059381.
International Search Report, revised, dated Jul. 6, 2012 for Application No. PCT/US2011/059381.
International Preliminary Report on Patentability dated May 8, 2013 for Application No. PCT/US2011/059381.
International Search Report and Written Opinion dated Jan. 26, 2012 for Application No. PCT/US2011/059212.
International Preliminary Report on Patentability dated May 7, 2013 for Application No. PCT/US2011/059212.
Japanese Office Action, Notification of Reasons for Refusal, dated Sep. 8, 2015 for Application No. 2013/537829.
Japanese Office Action, Notification of Reasons for Refusal, dated Jul. 5, 2016 for Application No. 2013/537829.
Japanese Office Action, Notification of Reasons for Refusal, dated Sep. 29, 2015 for Application No. 2013/537877.
U.S. Office Action, Non/Final dated Aug. 6, 2013 for U.S. Appl. No. 13/151,471.
U.S. Office Action, Notice of Allowance, dated Dec. 6, 2013 for U.S. Appl. No. 13/151,471.
U.S. Office Action, Non/Final, dated Mar. 28, 2014 for U.S. Appl. No. 13/151,471.
U.S. Office Action, Notice of Allowance, dated Aug. 19, 2014 for U.S. Appl. No. 13/151,471.
U.S. Office Action, Notice of Allowance, dated Nov. 21, 2014 for U.S. Appl. No. 13/151,471.
U.S. Office Action, Restriction Requirement, dated Dec. 11, 2012 for U.S. Appl. No. 13/151,481.
U.S. Office Action, Non/Final, dated Feb. 15, 2013 for U.S. Appl. No. 13/151,481.
U.S. Office Action, Final, dated Jun. 7, 2013 for U.S. Appl. No. 13/151,481.
U.S. Office Action, Non/Final, dated Aug. 14, 2014 for U.S. Appl. No. 13/151,481.
U.S. Office Action, Final, dated Apr. 1, 2015 for U.S. Appl. No. 13/151,481.
U.S. Office Action, Notice of Allowance, dated Jun. 10, 2015 for U.S. Appl. No. 13/151,481.
U.S. Office Action, Restriction Requirement, dated Jul. 5, 2013 for U.S. Appl. No. 13/151,488.
U.S. Office Action, Non/Final, dated Nov. 7, 2014 for U.S. Appl. No. 13/151,488.
U.S. Office Action, Non/Final, dated Jun. 14, 2013 for U.S. Appl. No. 13/151,498.

(56) References Cited

OTHER PUBLICATIONS

U.S. Office Action, Final, dated Nov. 21, 2013 for U.S. Appl. No. 13/151,498.
U.S. Office Action, Non/Final, dated Mar. 18, 2014 for U.S. Appl. No. 13/151,498.
U.S. Office Action, Notice of Allowance, dated Aug. 6, 2014 for U.S. Appl. No. 13/151,498.
U.S. Office Action, Notice of Allowance, dated Nov. 21, 2014 for U.S. Appl. No. 13/151,498.
U.S. Office Action, Non/Final, dated Jun. 18, 2014 for U.S. Appl. No. 13/151,503.
U.S. Office Action, Non/Final, dated Nov. 6, 2014 for U.S. Appl. No. 13/151,503.
U.S. Office Action, Restriction Requirement, dated Mar. 13, 2013 for U.S. Appl. No. 13/151,509.
U.S. Office Action, Restriction Requirement, dated Jun. 24, 2013 for U.S. Appl. No. 13/151,509.
U.S. Office Action, Non/Final, dated Sep. 26, 2013 for U.S. Appl. No. 13/151,509.
U.S. Office Action, Final, dated Jan. 29, 2014 for U.S. Appl. No. 13/151,509.
U.S. Office Action, Non/Final, dated Jul. 9, 2014 for U.S. Appl. No. 13/151,509.
U.S. Office Action, Notice of Allowance, dated Oct. 28, 2014 for U.S. Appl. No. 13/151,509.
U.S. Office Action, Notice of Allowance, dated Feb. 25, 2015 for U.S. Appl. No. 13/151,509.
U.S. Office Action, Restriction Requirement, dated Jun. 11, 2014 for U.S. Appl. No. 13/151,512.
U.S. Office Action, Notice of Allowance, dated Oct. 29, 2014 for U.S. Appl. No. 13/151,512.
U.S. Office Action, Notice of Allowance, dated Feb. 17, 2015 for U.S. Appl. No. 13/151,512.
U.S. Office Action, Restriction Requirement, dated Jul. 11, 2014 for U.S. Appl. No. 13/269,870.
U.S. Office Action, Non/Final, dated Jan. 5, 2015 for U.S. Appl. No. 13/269,870.
U.S. Office Action, Restriction Requirement, dated Feb. 28, 2013 for U.S. Appl. No. 13/270,667.
U.S. Office Action, Non/Final, dated Apr. 26, 2013 for U.S. Appl. No. 13/270,667.
U.S. Office Action, Final, dated Oct. 25, 2013 for U.S. Appl. No. 13/270,667.
U.S. Office Action, Non/Final, dated Jul. 29, 2014 for U.S. Appl. No. 13/270,667.
U.S. Office Action, Notice of Allowance, dated Dec. 17, 2014 for U.S. Appl. No. 13/270,667.
U.S. Office Action, Restriction Requirement, dated Jul. 9, 2014 for U.S. Appl. No. 13/270,684.
U.S. Office Action, Non/Final, dated Oct. 9, 2014 for U.S. Appl. No. 13/270,684.
U.S. Office Action, Restriction Requirement, dated Sep. 11, 2014 for U.S. Appl. No. 13/270,701.
U.S. Office Action, Non/Final, dated Dec. 16, 2014 for U.S. Appl. No. 13/270,701.
U.S. Office Action, Non/Final, dated Nov. 21, 2013 for U.S. Appl. No. 13/271,352.
U.S. Office Action, Restriction Requirement, dated Sep. 25, 2014 for U.S. Appl. No. 13/271,352.
U.S. Office Action, Restriction Requirement, dated Feb. 25, 2015 for U.S. Appl. No. 13/271,364.
U.S. Office Action, Restriction Requirement, dated Oct. 2, 2013 for U.S. Appl. No. 13/274,480.
U.S. Office Action, Non/Final, dated Feb. 14, 2014 for U.S. Appl. No. 13/274,480.
U.S. Office Action, Final, dated Jul. 17, 2014 for U.S. Appl. No. 13/274,480.
U.S. Office Action, Non/Final, dated May 1, 2015 for U.S. Appl. No. 13/274,480.
U.S. Office Action, Restriction Requirement, dated Dec. 9, 2013 for U.S. Appl. No. 13/274,496.
U.S. Office Action, Non/Final, dated Feb. 6, 2014 for Appl. No. 13/274,496.
U.S. Office Action, Final, dated May 15, 2014 for U.S. Appl. No. 13/274,496.
U.S. Office Action, Final, dated Aug. 22, 2014 for U.S. Appl. No. 13/274,496.
U.S. Office Action, Restriction Requirement, dated Mar. 28, 2014 for U.S. Appl. No. 13/274,507.
U.S. Office Action, Non/Final, dated Jun. 19, 2014 for U.S. Appl. No. 13/274,507.
U.S. Office Action, Non/Final, dated Dec. 21, 2012 for U.S. Appl. No. 13/274,516.
U.S. Office Action, Final, dated Aug. 16, 2013 for U.S. Appl. No. 13/274,516.
U.S. Office Action, Non/Final, dated Dec. 6, 2013 for U.S. Appl. No. 13/274,516.
U.S. Office Action, Final, dated Jun. 12, 2014 for U.S. Appl. No. 13/274,516.
U.S. Office Action, Non/Final, dated Oct. 8, 2014 for U.S. Appl. No. 13/274,516.
U.S. Office Action, Restriction Requirement, dated Feb. 25, 2013 for U.S. Appl. No. 13/274,540.
U.S. Office Action, Non/Final, dated Apr. 30, 2013 for U.S. Appl. No. 13/274,540.
U.S. Office Action, Final, dated Oct. 25, 2013 for U.S. Appl. No. 13/274,540.
U.S. Office Action, Non/Final, dated Aug. 26, 2014 for U.S. Appl. No. 13/274,540.
U.S. Office Action, Notice of Allowance, dated Jan. 21, 2015 for U.S. Appl. No. 13/274,540.
U.S. Office Action, Non/Final, dated Apr. 1, 2013 for U.S. Appl. No. 13/274,805.
U.S. Office Action, Final, dated Sep. 12, 2013 for U.S. Appl. No. 13/274,805.
U.S. Office Action, Non/Final, dated Aug. 14, 2014 for U.S. Appl. No. 13/274,805.
U.S. Office Action, Notice of Allowance, dated Nov. 28, 2014 for U.S. Appl. No. 13/274,805.
U.S. Office Action, Notice of Allowance, dated Jan. 21, 2015 for U.S. Appl. No. 13/274,805.
U.S. Office Action, Restriction Requirement, dated Apr. 29, 2013 for U.S. Appl. No. 13/274,830.
U.S. Office Action, Non/Final, dated Jun. 14, 2013 for U.S. Appl. No. 13/274,830.
U.S. Office Action, Final, dated Nov. 26, 2013 for U.S. Appl. No. 13/274,830.
U.S. Office Action, Non/Final, dated Oct. 22, 2014 for U.S. Appl. No. 13/274,830.
U.S. Office Action, Restriction Requirement, dated Apr. 4, 2013 for U.S. Appl. No. 13/275,495.
U.S. Office Action, Non/Final, dated May 31, 2013 for U.S. Appl. No. 13/275,495.
U.S. Office Action, Final, dated Dec. 5, 2013 for U.S. Appl. No. 13/275,495.
U.S. Office Action, Non/Final, dated Feb. 25, 2015 for U.S. Appl. No. 13/275,495.
U.S. Office Action, Non/Final, dated Jan. 6, 2014 for U.S. Appl. No. 13/275,514.
U.S. Office Action, Non/Final, dated Sep. 9, 2014 for U.S. Appl. No. 13/275,514.
U.S. Office Action, Non/Final, dated May 17, 2013 for U.S. Appl. No. 13/275,547.
U.S. Office Action, Final, dated Feb. 28, 2014 for U.S. Appl. No. 13/275,547.
U.S. Office Action, Non/Final, dated Aug. 20, 2014 for U.S. Appl. No. 13/275,547.
U.S. Office Action, Non/Final, dated Feb. 1, 2013 for U.S. Appl. No. 13/275,563.
U.S. Office Action, Final, dated Aug. 29, 2013 for U.S. Appl. No. 13/275,563.

(56) References Cited

OTHER PUBLICATIONS

U.S. Office Action, Non/Final, dated Oct. 23, 2014 for U.S. Appl. No. 13/275,563.
U.S. Office Action, Restriction Requirement, dated Feb. 6, 2013 for U.S. Appl. No. 13/276,660.
U.S. Office Action, Non/Final, dated Jun. 3, 2013 for U.S. Appl. No. 13/246,660.
U.S. Office Action, Restriction Requirement, dated Jul. 9, 2014 for U.S. Appl. No. 13/276,660.
U.S. Office Action, Notice of Allowance, dated Jun. 17, 2015 for U.S. Appl. No. 13/276,660.
U.S. Office Action, Non/Final, dated Dec. 21, 2012 for U.S. Appl. No. 13/276,673.
U.S. Office Action, Non/Final, dated Aug. 19, 2013 for U.S. Appl. No. 13/276,673.
U.S. Office Action, Final, dated Mar. 21, 2014 for U.S. Appl. No. 13/276,673.
U.S. Office Action, Non/Final, dated Aug. 14, 2014 for U.S. Appl. No. 13/276,673.
U.S. Office Action, Final, dated Mar. 13, 2015 for U.S. Appl. No. 13/276,673.
U.S. Office Action, Restriction Requirement, dated Feb. 6, 2013 for U.S. Appl. No. 13/276,687.
U.S. Office Action, Non/Final, dated Jun. 12, 2013 for U.S. Appl. No. 13/276,687.
U.S. Office Action, Notice of Allowance, dated Nov. 12, 2013 for U.S. Appl. No. 13/276,687.
U.S. Office Action, Notice of Allowance, dated Jun. 2, 2014 for U.S. Appl. No. 13/276,687.
U.S. Office Action, Notice of Allowance, dated Sep. 12, 2014 for U.S. Appl. No. 13/276,687.
U.S. Office Action, Notice of Allowance, dated Dec. 23, 2014 for U.S. Appl. No. 13/276,687.
U.S. Office Action, Restriction Requirement, dated Feb. 21, 2013 for U.S. Appl. No. 13/276,707.
U.S. Office Action, Non/Final, dated May 6, 2013 for U.S. Appl. No. 13/276,707.
U.S. Office Action, Final, dated Sep. 27, 2013 for U.S. Appl. No. 13/276,707.
U.S. Office Action, Non/Final, dated Jan. 29, 2015 for U.S. Appl. No. 13/276,707.
U.S. Office Action, Restriction Requirement, dated Feb. 6, 2013 for U.S. Appl. No. 13/276,725.
U.S. Office Action, Non/Final, dated Aug. 20, 2014 for U.S. Appl. No. 13/276,725.
U.S. Office Action, Restriction Requirement, dated Dec. 21, 2012 for U.S. Appl. No. 13/276,745.
U.S. Office Action, Non/Final, dated Apr. 30, 2013 for U.S. Appl. No. 13/276,745.
U.S. Office Action, Final, dated Nov. 8, 2013 for U.S. Appl. No. 13/276,745.
U.S. Office Action, Non/Final, dated Feb. 28, 2014 for U.S. Appl. No. 13/276,745.
U.S. Office Action, Notice of Allowance, dated Oct. 7, 2014 for U.S. Appl. No. 13/276,745.
U.S. Office Action, Notice of Allowance, dated Dec. 19, 2014 for U.S. Appl. No. 13/276,745.
U.S. Office Action, Restriction Requirement, dated Sep. 24, 2014 for U.S. Appl. No. 13/277,328.
U.S. Office Action, Non/Final, dated Dec. 8, 2014 for U.S. Appl. No. 13/277,328.
U.S. Office Action, Final, dated Mar. 24, 2015 for U.S. Appl. No. 13/277,328.
U.S. Office Action, Notice of Allowance, dated Jun. 1, 2015 for U.S. Appl. No. 13/277,328.
U.S. Office Action, Notice of Allowance, dated Jun. 17, 2016 for U.S. Appl. No. 13/277,328.
International Search Report and Written Opinion dated Feb. 24, 2016 for Application No. PCT/US2015/053935, 16 pgs.

\* cited by examiner

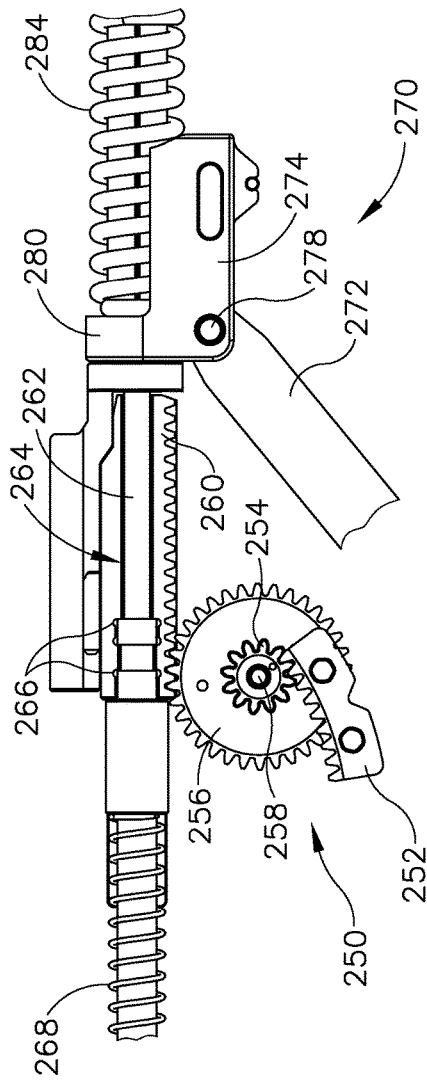
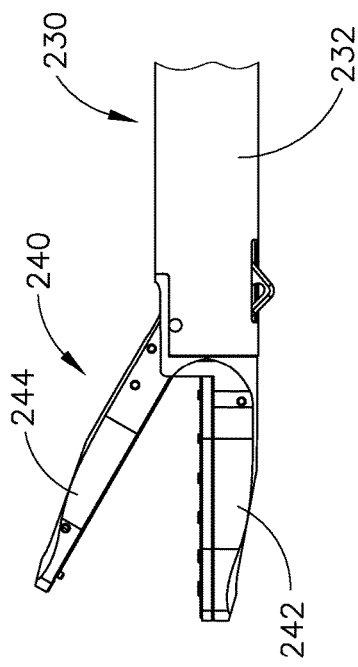
Fig.11
Fig.12

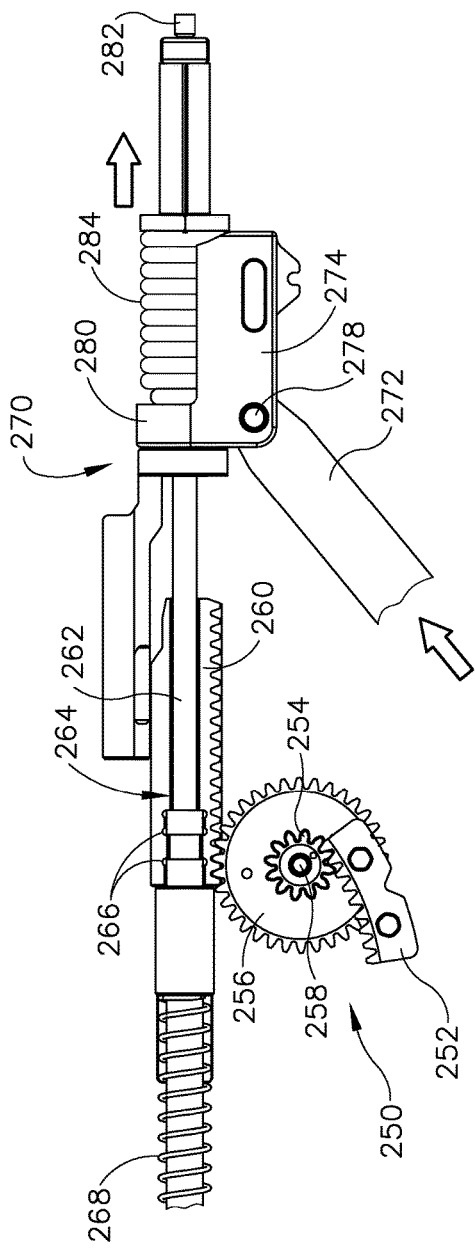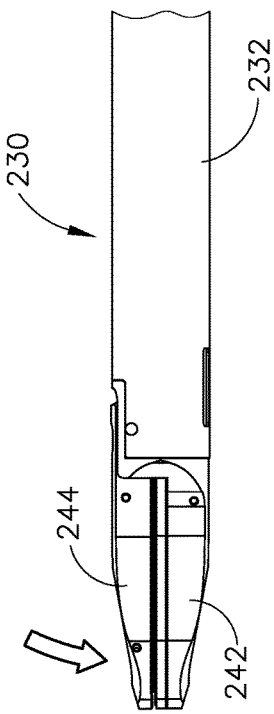
Fig.13
Fig.14

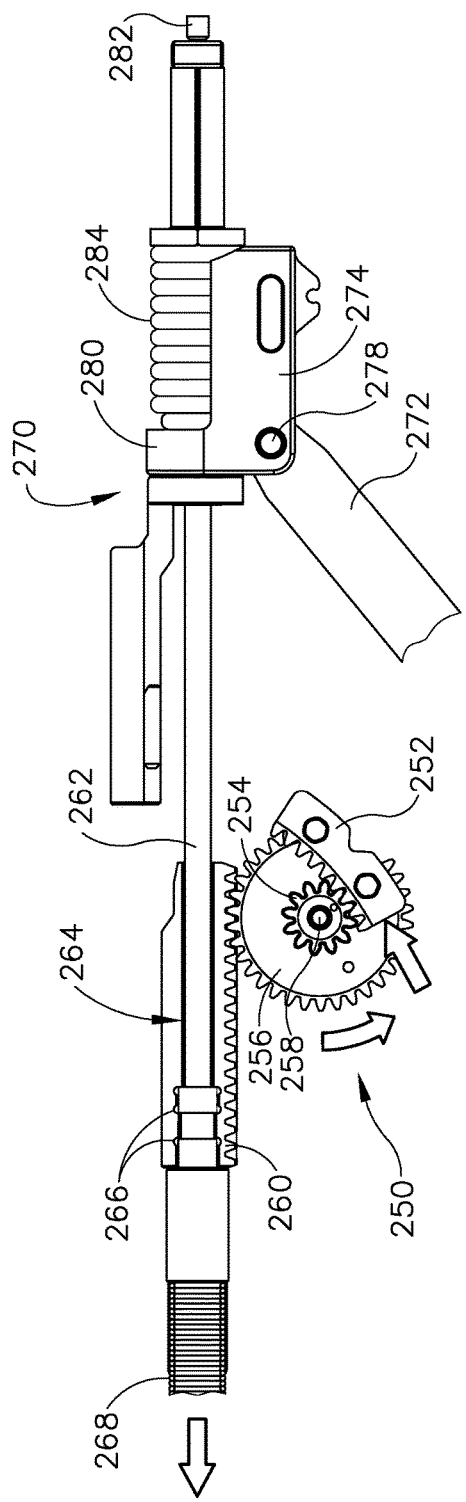
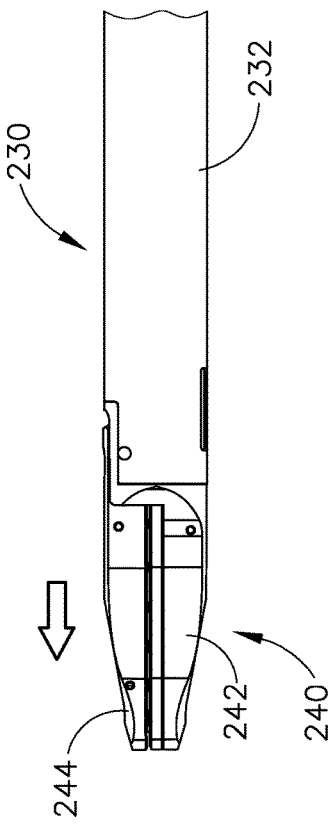

ELECTROSURGICAL INSTRUMENT WITH SENSOR

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; U.S. Pub. No. 2012/0083783, entitled "Surgical Instrument with Jaw Member," published Apr. 5, 2012, now U.S. Pat. No. 8,888,809, issued Nov. 18, 2014, the disclosure of which is incorporated by reference herein; U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein; U.S. Pub. No. 2012/0078243, entitled "Control Features for Articulating Surgical Device," published Mar. 29, 2012, now U.S. Pat. No. 9,877,720, issued Jan. 30, 2018, the disclosure of which is incorporated by reference herein; U.S. Pub. No. 2012/0078247, entitled "Articulation Joint Features for Articulating Surgical Device," published Mar. 29, 2012, now U.S. Pat. No. 9,402,682, issued Aug. 2, 2016, the disclosure of which is incorporated by reference herein; U.S. Pub. No. 2013/0030428, entitled "Surgical Instrument with Multi-Phase Trigger Bias," published Jan. 31, 2013, now U.S. Pat. No. 9,089,327, issued Jul. 28, 2015, the disclosure of which is incorporated by reference herein; and U.S. Pub. No. 2013/0023868, entitled "Surgical Instrument with Contained Dual Helix Actuator Assembly," published Jan. 31, 2013, now U.S. Pat. No. 9,545,253, issued Jan. 17, 2017, the disclosure of which is incorporated by reference herein.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 11 depicts a detailed side elevational view of the jaw actuation assembly and the firing beam actuation assembly of FIG. 10, both in an unactuated configuration;

FIG. 12 depicts a detailed side elevational view of an end effector of the instrument of FIG. 9, in an open configuration;

FIG. 13 depicts a detailed side elevational view of the firing beam actuation assembly and jaw actuation assembly of FIG. 10, the jaw actuation assembly in an actuated position and the firing beam actuation assembly in an unactuated position;

FIG. 14 depicts a detailed side elevational view of the end effector of FIG. 12, in a closed configuration;

FIG. 15 depicts a detailed side elevational view of the firing beam actuation assembly and jaw actuation assembly of FIG. 10, both in an actuated configuration;

FIG. 16 depicts a detailed side elevational view of the end effector of the instrument of FIG. 12, in a closed configuration with a firing beam advanced to a distal position;

Figure 1:
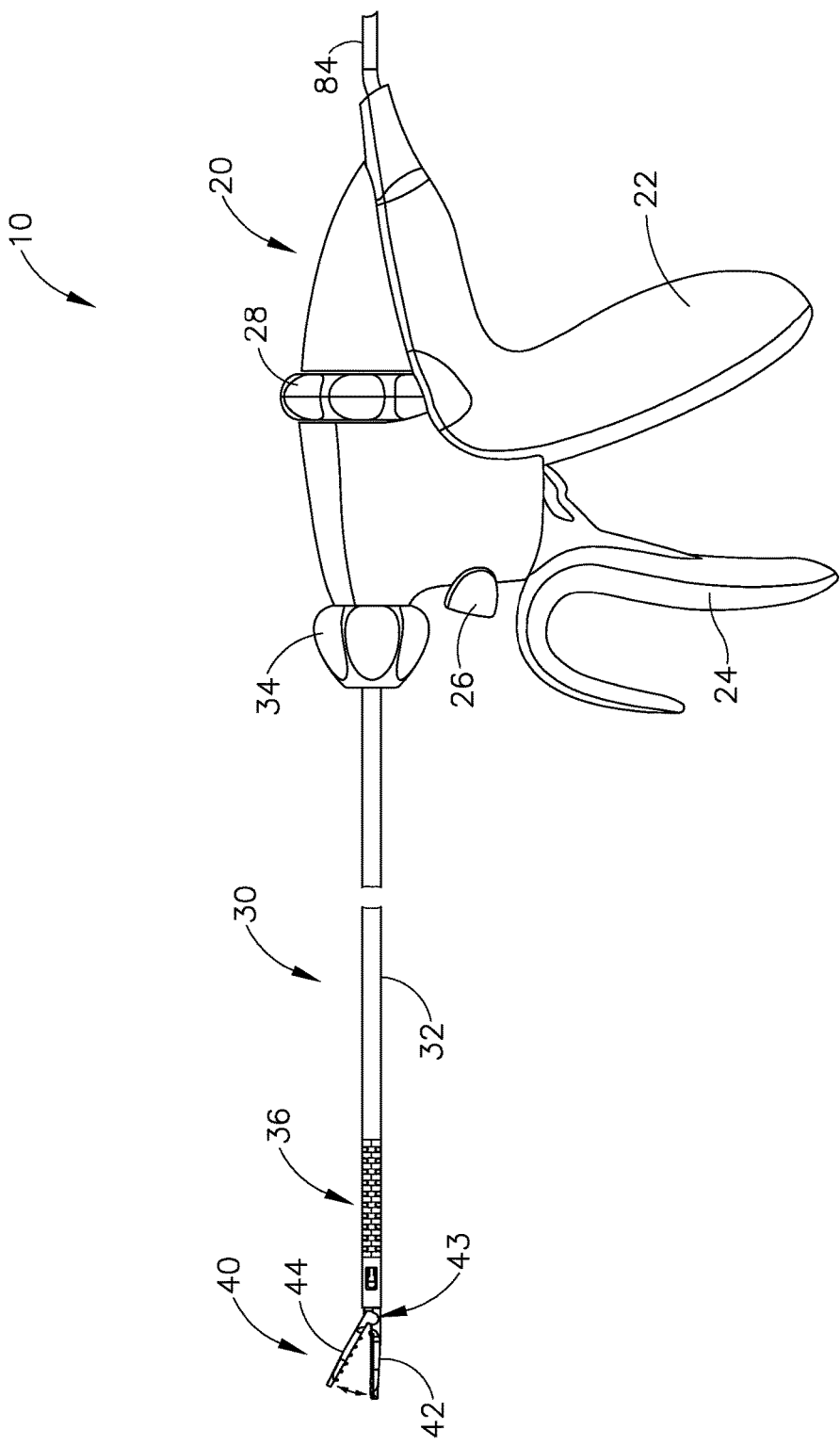
FIG. 1 depicts a side elevational view of an exemplary electrosurgical medical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Electrosurgical Device with Articulation Feature

FIGS. 1-4 show an exemplary electrosurgical instrument (10) that is constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218, now U.S. Pat. No. 8,939,974; U.S. Pub. No. 2012/0083783, now U.S. Pat. No. 8,888,809; U.S. Pub. No. 2012/0116379, now U.S. Pat. No. 9,161,803; U.S. Pub. No. 2012/0078243, now U.S. Pat. No. 9,877,720, issued Jan. 30, 2018; U.S. Pub. No. 2012/0078247, now U.S. Pat. No. 9,402,682; U.S. Pub. No. 2013/0030428, now U.S. Pat. No. 9,089,327; and/or U.S. Pub. No. 2013/0023868, now U.S. Pat. No. 9,545,253. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes a rigid outer sheath (32) and an articulation section (36). Articulation section (36) is operable to selectively laterally deflect end effector (40) at various angles relative to the longitudinal axis defined by sheath (32). In some versions, articulation section (36) and/or some other portion of outer sheath (32) includes a flexible outer sheath (e.g., a heat shrink tube, etc.) disposed about its exterior. Articulation section (36) of shaft (30) may take a variety of forms. By way of example only, articulation section (36) may be configured in accordance with one or more teachings of U.S. Pub. No. 2012/0078247, now U.S. Pat. No. 9,402,682, the disclosure of which is incorporated by reference herein. As another merely illustrative example, articulation section (36) may be configured in accordance with one or more teachings of U.S. Pub. No. 2012/0078248, entitled "Articulation Joint Features for Articulating Surgical Device," published Mar. 29, 2012, now U.S. Pat. No. 9,220,559, issued Dec. 29, 2015, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating articulation section (36) or any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating articulation section (36) or any portion of shaft (30) that is proximal of articulation section (36). Other suitable rotation schemes will be apparent to those of ordinary skill in the art in view of the teachings herein. Of course, rotatable features may simply be omitted if desired.

Articulation control (28) of the present example is operable to selectively control articulation section (36) of shaft (30), to thereby selectively laterally deflect end effector (40) at various angles relative to the longitudinal axis defined by shaft (30). While articulation control (28) is in the form of a rotary dial in the present example, it should be understood that articulation control (28) may take numerous other forms. By way of example only, some merely illustrative forms that articulation control (28) and other components of handpiece (20) may take are disclosed in U.S. Pub. No. 2012/0078243, now U.S. Pat. No. 9,877,720, issued Jan. 30, 2018, the disclosure of which is incorporated by reference herein; in U.S. Pub. No. 2012/0078244, entitled "Control Features for Articulating Surgical Device," published Mar. 29, 2012, the disclosure of which is incorporated by reference herein; and in U.S. Pub. No. 2013/0023868, now U.S. Pat. No. 9,545,253, the disclosure of which is incorporated by reference herein. Still other suitable forms that articulation control (28) may take will be apparent to those of ordinary skill in the art in view of the teachings herein. It should also be understood that some versions of instrument (10) may simply lack an articulation control (28).

B. Exemplary End Effector

End effector (40) of the present example comprises a first jaw (42) and a second jaw (44). In the present example, first jaw (42) is substantially fixed relative to shaft (30); while second jaw (44) pivots relative to shaft (30), toward and away from first jaw (42). Use of the term "pivot" should not be read as necessarily requiring pivotal movement about a fixed axis. In some versions, second jaw (44) pivots about an axis that is defined by a pin (or similar feature) that slides along an elongate slot or channel as second jaw (44) moves toward first jaw (42). In such versions, the pivot axis translates along the path defined by the slot or channel while second jaw (44) simultaneously pivots about that axis. It should be understood that such sliding/translating pivotal movement is encompassed within terms such as "pivot," "pivots," "pivotal," "pivotable," "pivoting," and the like. Of course, some versions may provide pivotal movement of second jaw (44) about an axis that remains fixed and does not translate within a slot or channel, etc.

In some versions, actuators such as rods or cables, etc., may extend through sheath (32) and be joined with second jaw (44) at a pivotal coupling (43), such that longitudinal movement of the actuator rods/cables/etc. through shaft (30) provides pivoting of second jaw (44) relative to shaft (30) and relative to first jaw (42). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
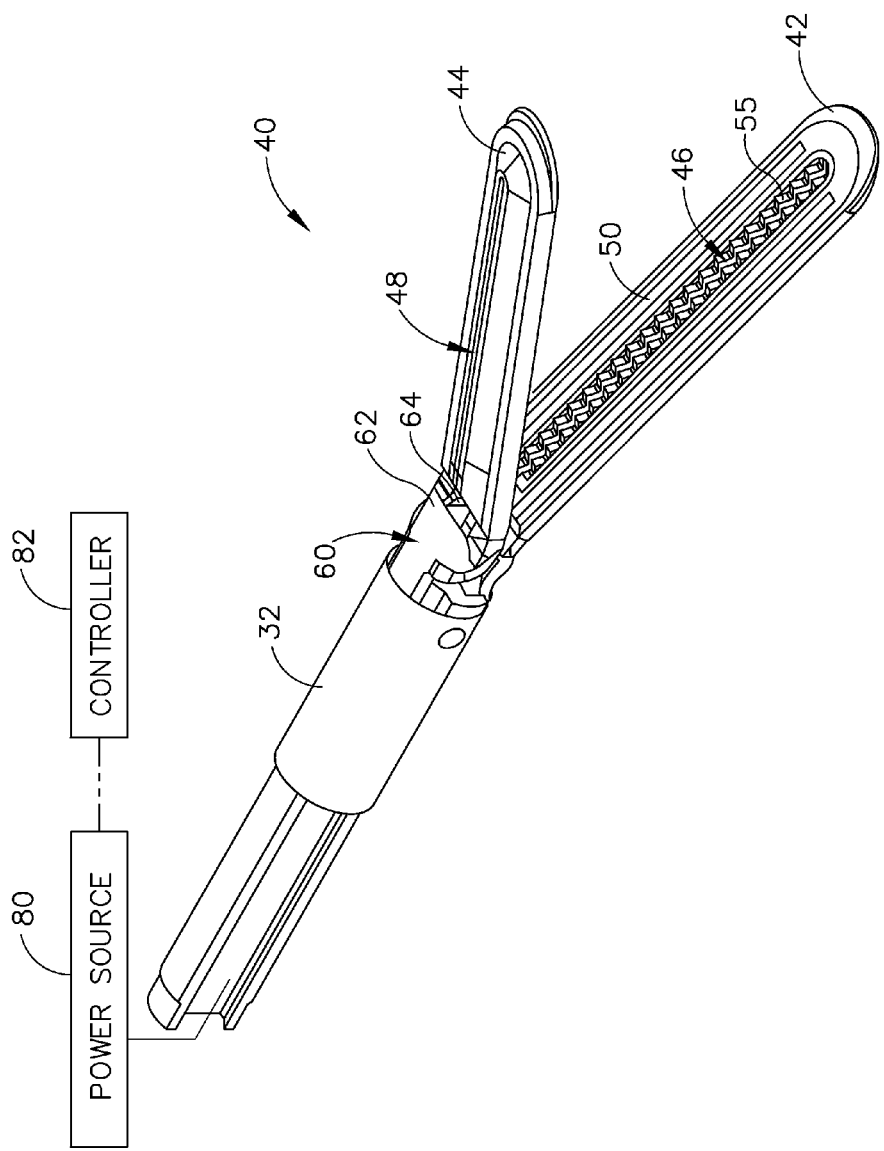
FIG. 2 depicts a perspective view of the end effector of the instrument of FIG. 1, in an open configuration.
Figure 3:
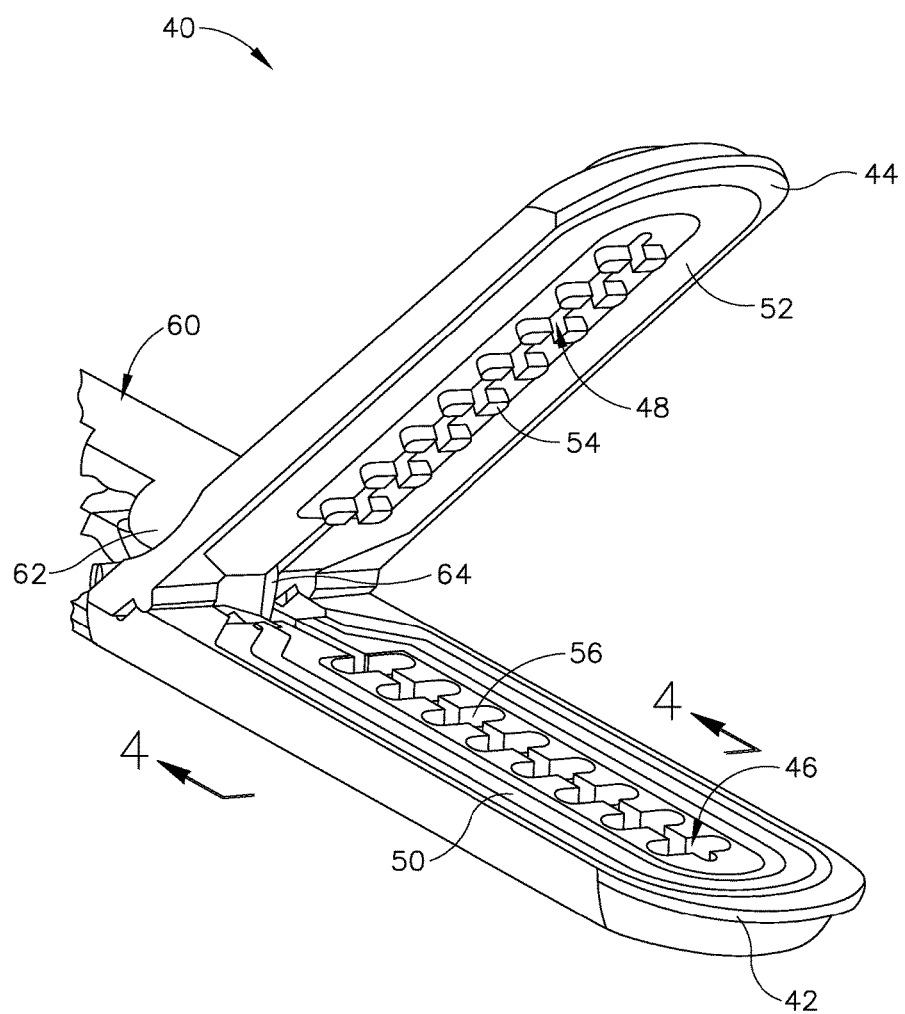
FIG. 3 depicts another perspective view of the end effector of FIG. 2, in an open configuration.
Figure 4:
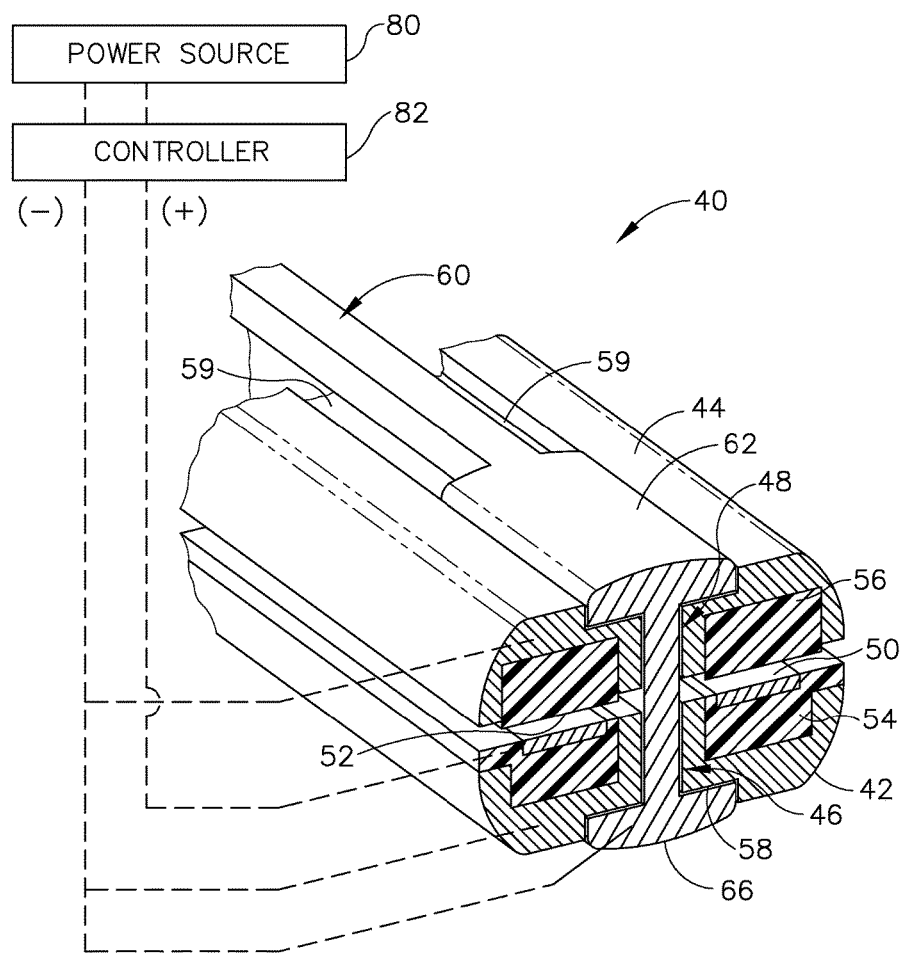
FIG. 4 depicts a cross-sectional end view of the end effector of FIG. 2, taken along line 4-4 of FIG. 3, in a closed configuration and with the blade in a distal position.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw

(44) presents a second electrode surface (52). Electrode surfaces (50, 52) are in communication with an electrical source (80) via one or more conductors (not shown) that extend along the length of shaft (30). These conductors are coupled with electrical source (80) and a controller (82) via a cable (84), which extends proximally from handpiece (20). Electrical source (80) is operable to deliver RF energy to first electrode surface (50) at a first polarity and to second electrode surface (52) at a second (opposite) polarity, such that RF current flows between electrode surfaces (50, 52) and thereby through tissue captured between jaws (42, 44). In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

By way of example only, power source (80) and/or controller (82) may be configured in accordance with at least some of the teachings of U.S. Provisional Pat. App. No. 61/550,768, entitled "Medical Instrument," filed Oct. 24, 2011, the disclosure of which is incorporated by reference herein; U.S. Pub. No. 2011/0082486, entitled "Devices and Techniques for Cutting and Coagulating Tissue," published Apr. 7, 2011, now U.S. Pat. No. 9,089,360, issued Jul. 28, 2015, the disclosure of which is incorporated by reference herein; U.S. Pub. No. 2011/0087212, entitled "Surgical Generator for Ultrasonic and Electrosurgical Devices," published Apr. 14, 2011 now U.S. Pat. No. 8,986,302, issued Mar. 24, 2015, the disclosure of which is incorporated by reference herein; U.S. Pub. No. 2011/0087213, entitled "Surgical Generator for Ultrasonic and Electrosurgical Devices," published Apr. 14, 2011, now U.S. Pat. No. 8,951,248, issued Feb. 10, 2015, the disclosure of which is incorporated by reference herein; U.S. Pub. No. 2011/0087214, entitled "Surgical Generator for Ultrasonic and Electrosurgical Devices," published Apr. 14, 2011, now U.S. Pat. No. 9,039,695, issued May 26, 2015, the disclosure of which is incorporated by reference herein; U.S. Pub. No. 2011/0087215, entitled "Surgical Generator for Ultrasonic and Electrosurgical Devices," published Apr. 14, 2011, now U.S. Pat. No. 9,050,093, issued Jun. 9, 2015, the disclosure of which is incorporated by reference herein; U.S. Pub. No. 2011/0087216, entitled "Surgical Generator for Ultrasonic and Electrosurgical Devices," published Apr. 14, 2011, now U.S. Pat. No. 8,956,349, issued Feb. 17, 2015, the disclosure of which is incorporated by reference herein; and/or U.S. Pub. No. 2011/0087217, entitled "Surgical Generator for Ultrasonic and Electrosurgical Devices," published Apr. 14, 2011, now U.S. Pat. No. 9,060,776, issued Jun. 23, 2015, the disclosure of which is incorporated by reference herein. Other suitable configurations for power source (80) and controller (82) will be apparent to those of ordinary skill in the art in view of the teachings herein.

As best seen in FIG. 4, the lower side of first jaw (42) includes a longitudinally extending recess (58) adjacent to slot (46); while the upper side of second jaw (44) includes a longitudinally extending recess (59) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. In other words, it should be understood that serrations may be generally blunt or otherwise atraumatic. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44).

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56)

at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. In some versions, a proximal end of firing beam (60) is secured to a firing tube or other structure within shaft (30); and the firing tube or other structure extends through the remainder of shaft (30) to handpiece (20) where it is driven by movement of trigger (24). Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode. In addition or in the alternative, distal blade (64) may be selectively energized with ultrasonic energy (e.g., harmonic vibrations at approximately 55.5 kHz, etc.).

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze trigger (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (44) when firing beam (60) is retracted to a proximal position and to hold jaw (44) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

Figure 5:
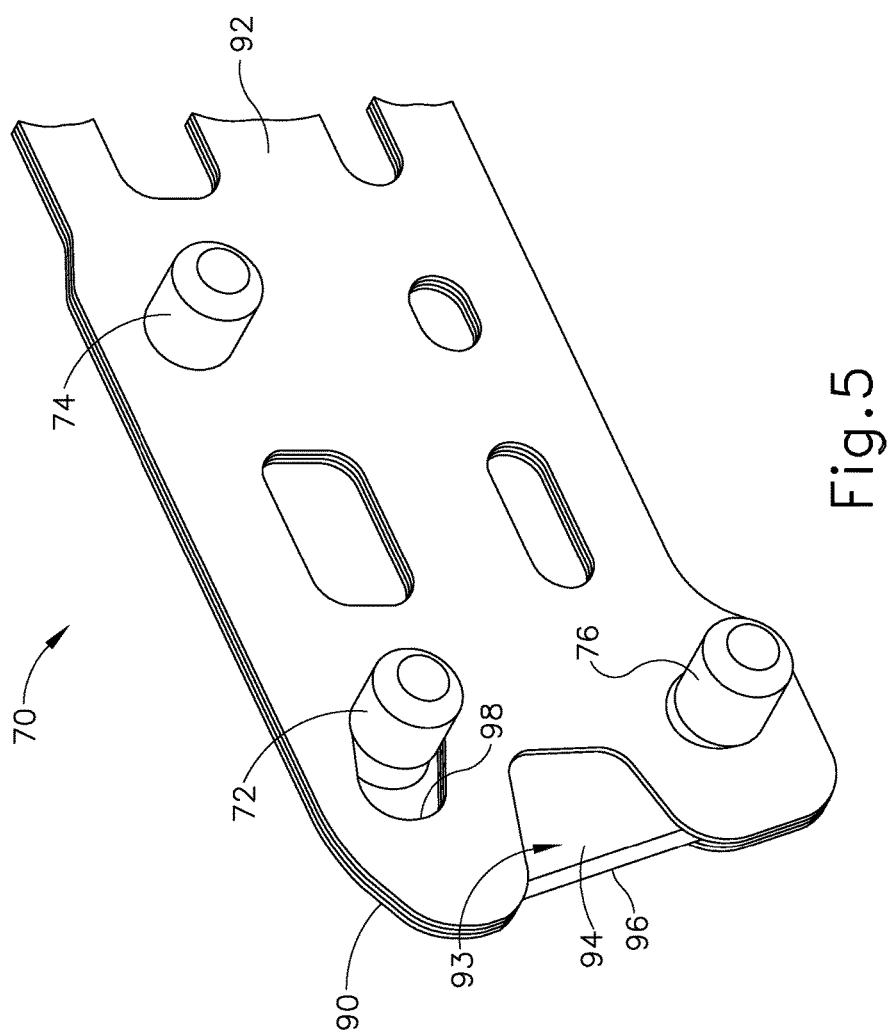
FIG. 5 depicts a partial perspective view of the distal end of an exemplary alternative firing beam suitable for incorporation in the instrument of FIG. 1.

FIG. 5 shows an exemplary alternative firing beam (70), which may be readily substituted for firing beam (60). In this example, firing beam (70) comprises a blade insert (94) that is interposed between two beam plates (90, 92). Blade insert (94) includes a sharp distal edge (96), such that blade insert (94) will readily sever tissue that is captured between jaws (42, 44). Sharp distal edge (96) is exposed by a proximally extending recess (93) formed in plates (90, 92). A set of pins (72, 74, 76) are transversely disposed in plates (90, 92). Pins (72, 74) together effectively serve as substitutes for upper flange (62); while pin (76) effectively serves as a substitute for lower flange (66). Thus, pins (72, 74) bear against channel (59) of jaw (44), and pin (76) bears against channel (58) of jaw (42), as firing beam (70) is translated distally through slots (46, 48). Pins (72, 74, 76) of the present example are further configured to rotate within plates (90, 92), about the axes respectively defined by pins (72, 74, 76). It should be understood that such rotatability of pins (72, 74, 76) may provide reduced friction with jaws (42, 44), thereby reducing the force required to translate firing beam (70) distally and proximally in jaws (42, 44). Pin (72) is disposed in an angled elongate slot (98) formed through plates (90, 92), such that pin (72) is translatable along slot (98). In particular, pin (72) is disposed in the proximal portion of slot (98) as firing beam (70) is being translated distally. When firing beam (70) is translated proximally, pin (72) slides distally and upwardly in slot (98), increasing the vertical separation between pins (72, 76), which in turn reduces the compressive forces applied by jaws (42, 44) and thereby reduces the force required to retract firing beam (70). Of course, firing beam (70) may have any other suitable configuration. By way of example only, firing beam (70) may be configured in accordance with at least some of the teachings of U.S. Pub. No. 2012/0083783, now U.S. Pat. No. 8,888, 809, the disclosure of which is incorporated by reference herein.

D. Exemplary Operation

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (42) toward jaw (44) when firing beam (60) is actuated distally by squeezing trigger (24) toward pistol grip (22). Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, may help keep jaws (42, 44) in a closed and tightly clamping position. In particular, flanges (62, 66) may help maintain a significantly compressive force between jaws (42, 44). With severed tissue layer portions being compressed between jaws (42, 44), electrode surfaces (50, 52) are activated with bipolar RF energy by the user depressing activation button (26). In some versions, electrodes (50, 52) are selectively coupled with power source (80) (e.g., by the user depressing button (26), etc.) such that electrode surfaces (50, 52) of jaws (42, 44) are activated with a common first polarity while firing beam (60) is activated at a second polarity that is opposite to the first polarity. Thus, a bipolar RF current flows between firing beam (60) and electrode surfaces (50, 52) of jaws (42, 44), through the compressed regions of severed tissue layer portions. In some other versions, electrode surface (50) has one polarity while electrode surface (52) and firing beam (60) both have the other polarity. In either version (among at least some others), bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52). Other suitable ways in which instrument (10) may be operable and operated will be apparent to those of ordinary skill in the art in view of the teachings herein.

II. Exemplary Alternative Electrosurgical Instrument with Jaw Sensor in End Effector In some instances, it may be desirable to provide one or more sensors that are operable to sense the gap between first jaw (42) and second jaw (44), and/or to sense the angle of second jaw (44) relative to first jaw (42). Such a sensor may be used to ensure that tissue captured between jaws (42, 44) is sealed to a desired degree when using electrosurgical instrument (10) in the procedure described above. In particular, such sensors may provide a signal to controller (82) that may cause controller (82) to modify certain sealing algorithm parameters. For instance, if the jaw gap or angle is over a certain value—indicating a larger tissue bundle—such sensors may communicate such a condition to controller (82). Controller (82) may then increase the RF power output to electrode surfaces (50, 52) to increase the sealing power of jaws (42, 44). Similarly, if the jaw gap or angle is under a certain value—indicating a relatively small tissue bundle such sensors may communicate such a condition to controller (82) so that controller (82) may decrease the sealing RF power of jaws (42, 44) or completely stop the delivery of RF power to the jaws (42, 44).

Additionally, such sensors may include certain adjustment features that may be used to calibrate or adjust the sensors. Such adjustment features may be used in the manufacturing environment to calibrate or adjust the sensors to compensate for tolerance variation of various parts of electrosurgical instrument (10). In addition or in alternative, such adjustment features may be used in the field to adjust or calibrate the sensors in response to various conditions encountered by an operator during a surgical procedure. Of course, sensors may include any other features or variations of features described herein, as will be apparent to those of ordinary skill in the art in view of the teachings herein. It should be understood that the examples discussed below may be used with any of the electrosurgical instruments discussed above or disclosed herein.

Figure 6:
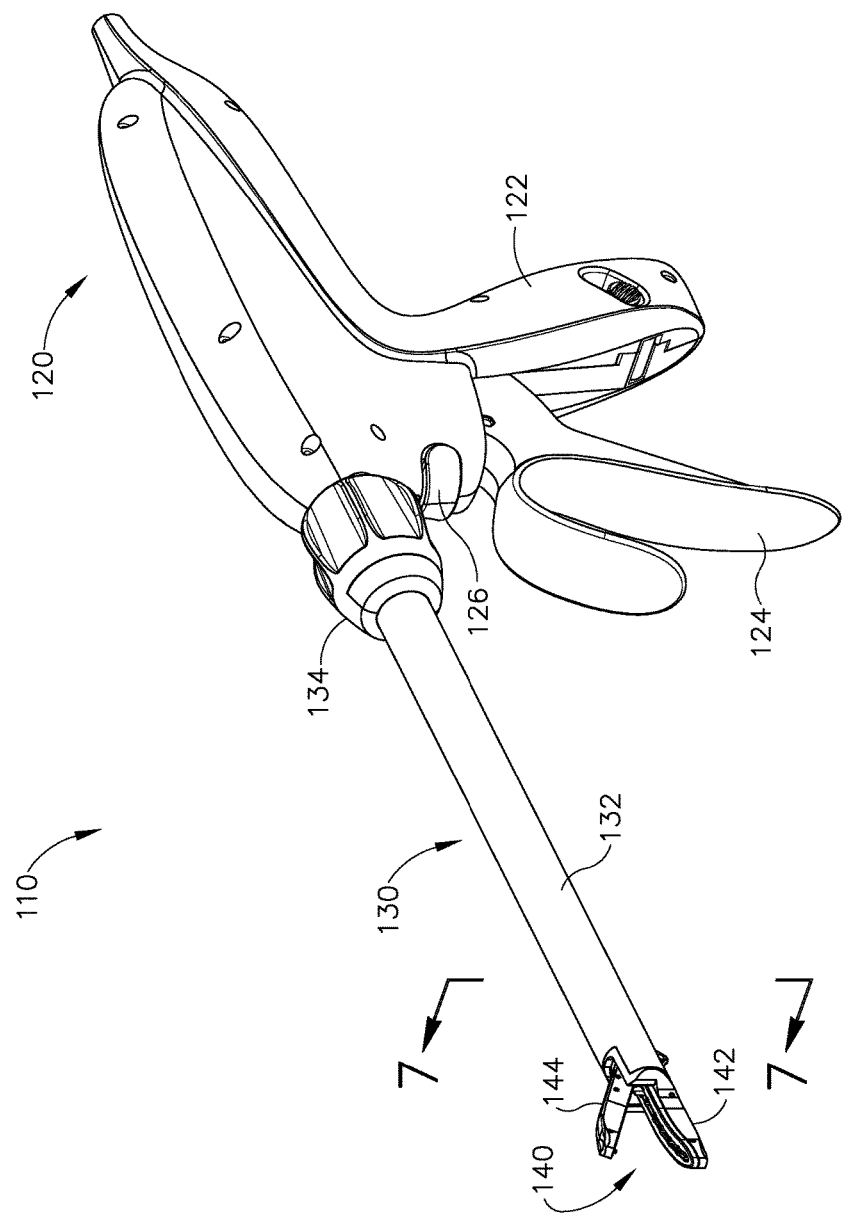
FIG. 6 depicts a perspective view of an exemplary alternative electrosurgical instrument.
Figure 7:
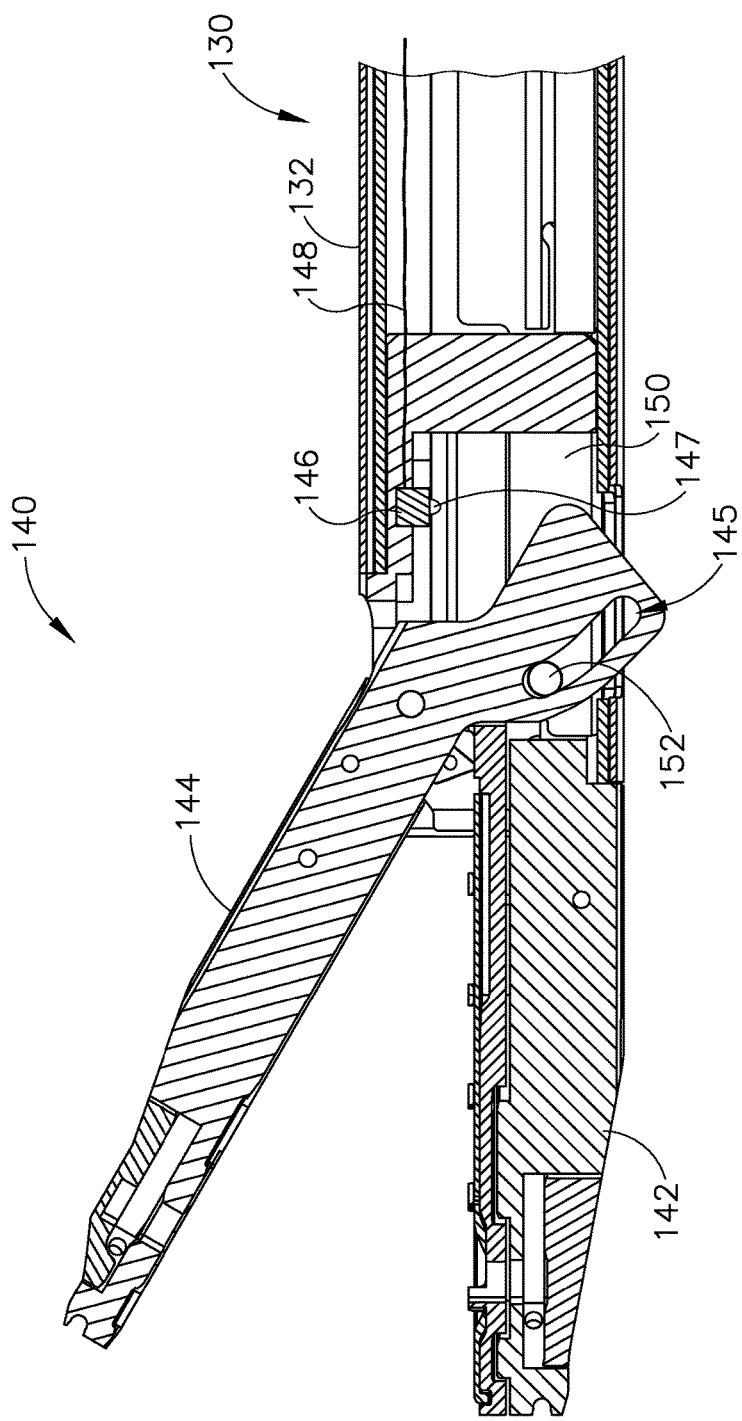
FIG. 7 depicts a cross-sectional side view of an end effector of the electrosurgical instrument of FIG. 6 with an end effector in an open configuration, the cross-section taken along line 7-7 of FIG. 6.
Figure 8:
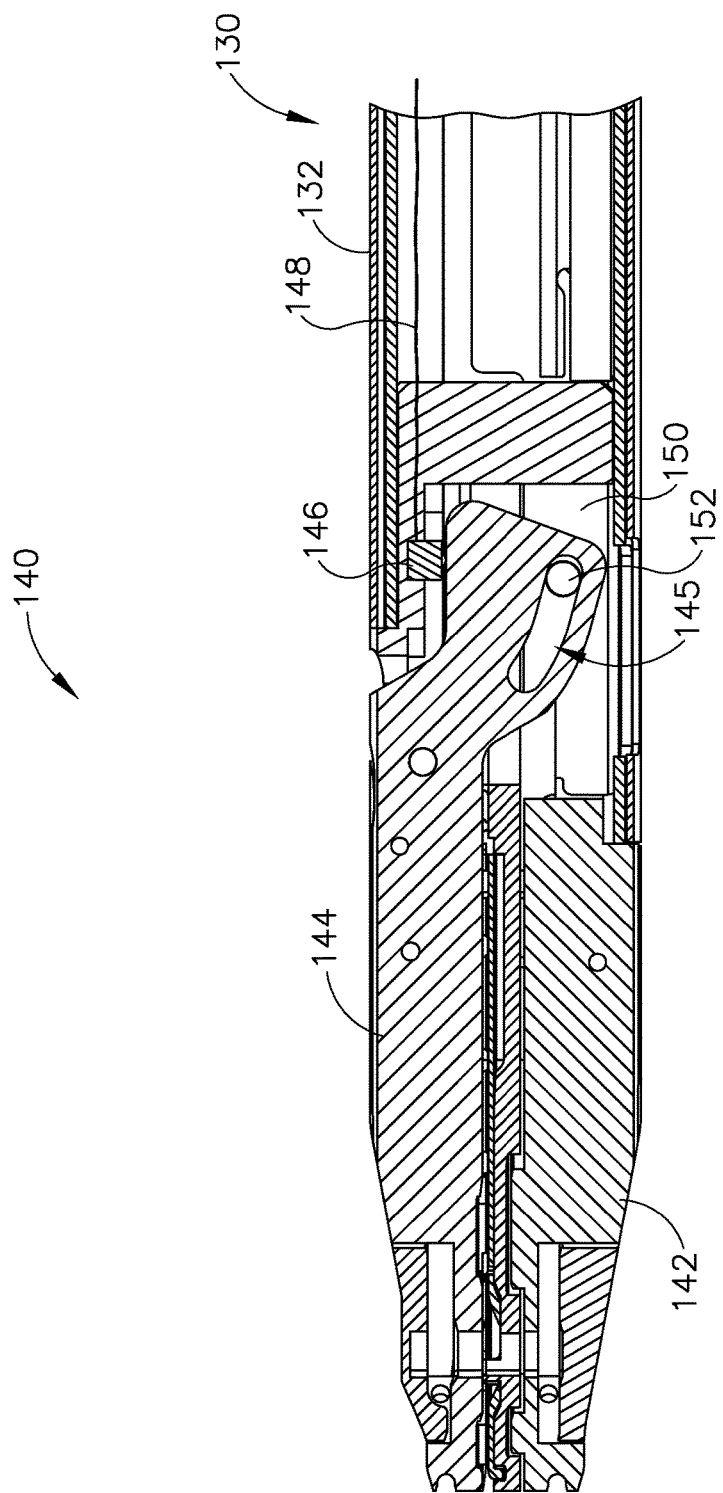
FIG. 8 depicts a cross-sectional side view of the end effector of FIG. 7 with the end effector in a closed configuration, the cross-section taken along line 7-7 of FIG. 6.
Figure 9:
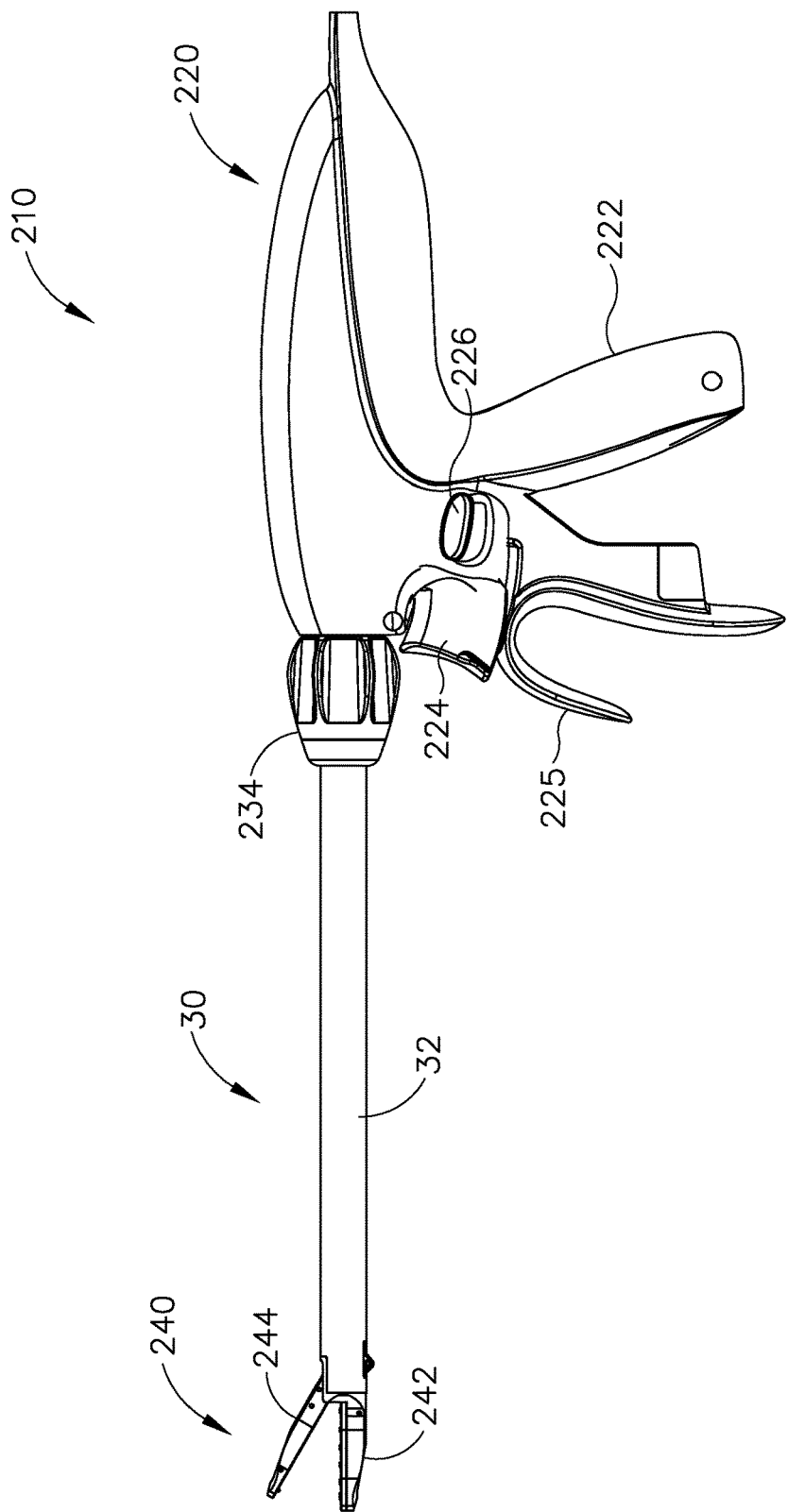
FIG. 9 depicts a side elevational view of an exemplary alternative electrosurgical medical instrument.

FIGS. 6-8 show an exemplary electrosurgical instrument (110) that includes a jaw sensor (146) associated with an end effector (140). Except as otherwise described below, electrosurgical instrument (110) is substantially the same as electrosurgical instrument (10) described above. Electrosurgical instrument (110) of the present example includes a handpiece (120), a shaft (130) extending distally from handpiece (120), and end effector (140) disposed at a distal end of shaft (130). Handpiece (120) of the present example includes a pistol grip (122), a pivoting trigger (124), and an activation button (126). Trigger (124) is pivotable toward and away from pistol grip (122) to selectively actuate end effector (140) similarly to trigger (24) described above. Activation button (126) is operable to selectively activate RF circuitry that is in communication with end effector (140). Shaft (130) of the present example includes a rigid outer sheath (132) without an articulation section, though it should be understood that some variations may include an articulation section. Shaft (130) is rotatable about the longitudinal axis defined by sheath (132), relative to handpiece (120), via a knob (134). Such rotation may provide rotation of end effector (140) and shaft (130) unitarily.

FIGS. 7-8 show a cross-section of end effector (140). As can be seen, end effector (140) comprises a first jaw (142), a second jaw (144), an actuation rod (150), and a jaw sensor (146). First jaw (142) is substantially fixed relative to shaft (130); while second jaw (144) pivots relative to shaft (130), toward and away from first jaw (142). Actuation rod (150) is slidable within shaft (130) and is actuated proximally and distally by trigger (124). Actuation rod (150) includes a pin (152), which is configured to engage second jaw (144). End effector (140) of the present example is actuated between an open and closed position via actuation rod (150), instead of a firing beam similar to firing beam (60) of end effector (40). In particular, second jaw (144) is pivotally pulled to a closed position by pin (152), which slides along an elongate slot (145) in second jaw (144) as second jaw (144) moves toward first jaw (142). Of course, second jaw (144) may be pivoted relative to first jaw (142) in any other suitable way as will be apparent to those of ordinary skill in the art in view of the teachings herein.

While instrument (110) of this example does not rely on distal advancement of a firing beam like firing beams (60, 70) in order to close jaw (144) toward jaw (142), instrument (110) may nevertheless still include a reciprocating firing beam like firing beam (60) that is operable to cut through tissue that is captured between jaws (142, 144). Such a firing beam may be configured similar to firing beam (60), similar to firing beam (70), or in any other suitable fashion. By way of example only, features in handpiece (120) may provide proximal retraction of actuation rod (150) to close jaws (142, 144) as trigger (124) is pivoted through a first range of motion toward pistol grip (122); followed by distal advancement of a firing beam as trigger (124) is pivoted through a second range of motion toward pistol grip (122). Various suitable components and configurations that may be used to provide such multi-stage operability of trigger (124) will be apparent to those of ordinary skill in the art in view of the teachings herein. It should also be understood that handpiece (120) may include separate actuation features (e.g., separate triggers, etc.) to provide separate actuation of actuation rod (150) and the firing beam.

Jaw sensor (146) includes a moveable protrusion (147) and an electrical wire (148). Moveable protrusion (147) protrudes from jaw sensor (146) toward the longitudinal axis of shaft (130) and may be pushed by second jaw (144) away from the longitudinal axis of shaft (130) as will be described in greater detail below. In the present example, movable protrusion (147) is resiliently biased toward the longitudinal axis of shaft (130) such that it may return to the position shown in FIG. 7 when not engaged with second jaw (144). Wire (148) extends through electrosurgical instrument so that jaw sensor (146) may be placed in communication with a controller (82) or other similar device.

As can best be seen in FIG. 8, jaw sensor (146) is positioned within end effector (140) such that when second jaw (144) closes to a desired distance from first jaw (142), the proximal end of second jaw (144) engages movable protrusion (147), thereby activating or deactivating jaw sensor (146). Although jaw sensor (146) is shown as being in a particular position within end effector (140), it should be understood that jaw sensor (146) may be positioned in any suitable location within end effector (140). In the present example, other suitable locations may include any location within end effector (140) corresponding to the location of a portion of second jaw (144) when second jaw (144) closes to a desired distance. In other examples, second jaw (144) may be of a different shape and/or may be actuated by a different mechanism. Of course, in such other examples the positioning of jaw sensor (146) may be altered as will be apparent to those of ordinary skill in the art in view of the teachings herein.

In the present example, jaw sensor (146) is a binary switch. In other words, jaw sensor (146) is configured to have two states—open or closed. For instance, in some versions, jaw sensor (146) may be in the opened state when second jaw (144) is in the open position and movable protrusion (147) is fully protruding from jaw sensor (146). Correspondingly, jaw sensor (146) will be in the closed state when second jaw (144) is in the closed position and movable protrusion (147) is fully engaged by second jaw (144). Of course, in other configurations jaw sensor (146) may be configured oppositely with the open state corresponding to the jaw being in the closed position and the closed state corresponding to the jaw being in the open position. Those of ordinary skill in the art will immediately recognize the various kinds of form that jaw sensor (146) may take, including but not limited to a contact switch, a reed switch, a hall effect sensor, capacitive sensor, etc.

In an exemplary mode of operation, second jaw (144) may be closed by actuation rod (150). As second jaw (144) is closed by actuation rod (144), the proximal end of second jaw (144) may engage movable protrusion (147) of jaw sensor (146). Further closure of second jaw (144) by actuation rod (144) will cause jaw sensor (144) to switch states (e.g., from open to closed, or closed to open). It should be understood that when such a switch in state occurs, second jaw (144) will be closed to a certain degree corresponding to a desired closure gap between first jaw (142) and second jaw (144).

Controller (82) may be configured to respond to changes in state of jaw sensor (146) communicated to controller (82) by wire (148). In particular, when controller (82) receives a signal from jaw sensor (146) corresponding to the closed position of second jaw (144), controller (82) may be converted into a ready state where subsequent activation of button (126) provides RF energy to jaws (142, 144). Conversely, if button (126) is activated before jaw sensor (146) indicates a sufficiently closed position of jaw (144), controller (82) may be prevented from providing RF energy to jaws (142, 144). In addition or in the alternative, controller (82) may activate a user feedback feature (e.g., audible tone, visible light, etc.) to alert the operator that jaw (144) is insufficiently closed if the operator activates button (126) before jaw sensor (146) indicates a sufficiently closed position of jaw (144). In addition to or as an alternative to the foregoing, jaw sensor (146) may be configured to detect closure of jaws (142, 144) in the absence of tissue between jaws (142, 144). In other words, sensor (146) and controller

(82) may be operable to determine that jaws (142, 144) have been closed without tissue being positioned between jaws (142, 144). In such instances, controller (82) may prevent the delivery of RF energy to jaws (142, 144). In addition or in the alternative, controller (82) may activate a user feedback feature (e.g., audible tone, visible light, etc.) to alert the operator that end effector (140) needs to be repositioned in order to position tissue between jaws (142, 144) before jaws (142, 144) may deliver RF energy.

Although jaw sensor (146) is described herein as being binary in nature, it should be understood that in other examples jaw sensor (146) may be non-binary having a plurality of outputs to communicate different amount of closure of second jaw (144). In such examples, controller (82) may be responsive to varying degrees of input from jaw sensor (146) indicating differing amounts of closure of second jaw (144) such that RF power may be altered depending on different amounts of closure of second jaw (144). For instance, if jaw sensor (146) indicates a relatively wide separation of jaw (144) from jaw (142) when button (126) is activated (e.g., indicating a relatively thick bundle of tissue), controller (82) may provide a relatively high level of RF energy to jaws (142, 144). If jaw sensor (146) indicates a relatively small separation of jaw (144) from jaw (142) when button (126) is activated (e.g., indicating a relatively thin bundle of tissue), controller (82) may provide a relatively low level of RF energy to jaws (142, 144). It should also be understood that controller may (82) provide a control algorithm that factors in feedback from jaw sensor (146) and feedback indicating an electrical resistance of tissue in jaws (142, 144). Various suitable ways in which the electrical resistance of tissue may be sensed will be apparent to those of ordinary skill in the art in view of the teachings herein. Of course, controller (82) may be responsive to jaw sensor (146) and/or other sources of feedback in any other suitable way as will be apparent to those of ordinary skill in the art in view of the teachings herein.

III. Exemplary Jaw Sensors Positioned in Handle Assembly

In some instances it may be desirable to place a jaw sensor similar to jaw sensor (146) described above in a handpiece of an electrosurgical instrument, instead of in an end effector. In such examples, positioning of the jaw sensor in the handpiece may provide additional space for placement of various components which that be used with the jaw sensor. For instance, additional space may be required for adjustment mechanisms, electronic circuitry, and/or drive mechanisms that are configured to amplify the movement of the end effector and more precisely detect the position of a jaw in end effector. By way of example only, the mechanisms described below may be operable to amplify motion of approximately 0.01 inches to approximately 0.05 inches or greater. It should be understood that the electrosurgical instruments described below are merely exemplary and various features of each electrosurgical instrument may be combined with other electrosurgical instruments described herein.

A. Exemplary Electrosurgical Instrument with Jaw Sensor Activated by Upwardly Pivoting Arm FIGS. 9-22 show an exemplary electrosurgical instrument (210) with a jaw sensor (308) integrated into a jaw actuation assembly (290). Except as otherwise described below, electrosurgical instrument (210) is substantially the same as electrosurgical instrument (10) described above. Electrosurgical instrument (210) of the present example includes a handpiece (220), a shaft (230) extending distally from handpiece (220), and end effector (240) disposed at a distal end of shaft (230). Handpiece (220) of the present example includes a pistol grip (222), pivoting blade and jaw triggers (224, 225), and an activation button (226). As will be described in greater detail below, blade and jaw triggers (224, 225) are separately pivotable toward and away from pistol grip (222) to selectively actuate a firing beam (not shown) and jaws (242, 244) of end effector (240), respectively. Activation button (226) is operable to selectively activate RF circuitry that is in communication with end effector (240).

Shaft (230) of the present example includes a rigid outer sheath (232) without an articulation section, though it should be understood that some variations may include an articulation section. Shaft (230) is rotatable about the longitudinal axis defined by sheath (232), relative to handpiece (220), via a knob (234). Such rotation may provide rotation of end effector (240) and shaft (230) unitarily.

End effector (240) is similar to end effector (40) described above. Like end effector (40), end effector (240) comprises a first jaw (242) and a second jaw (244). First jaw (242) is fixed relative to shaft (230) such that first jaw (242) remains stationary as end effector (240) actuates. Second jaw (244) is pivotable relative to first jaw (244) such that second jaw (244) transitions between an open and closed position as end effector (240) is actuated. Second jaw (244) may be pivoted in any suitable way as will be apparent to those of ordinary skill in the art in view of the teachings herein. Instrument (210) further includes a firing beam (not shown) that is operable to translate through end effector (240) to thereby sever tissue captured between jaws (242, 244). By way of example only, such a firing beam may be configured similar to firing beam (60), similar to firing beam (70), or in any other suitable fashion.

Figure 10:
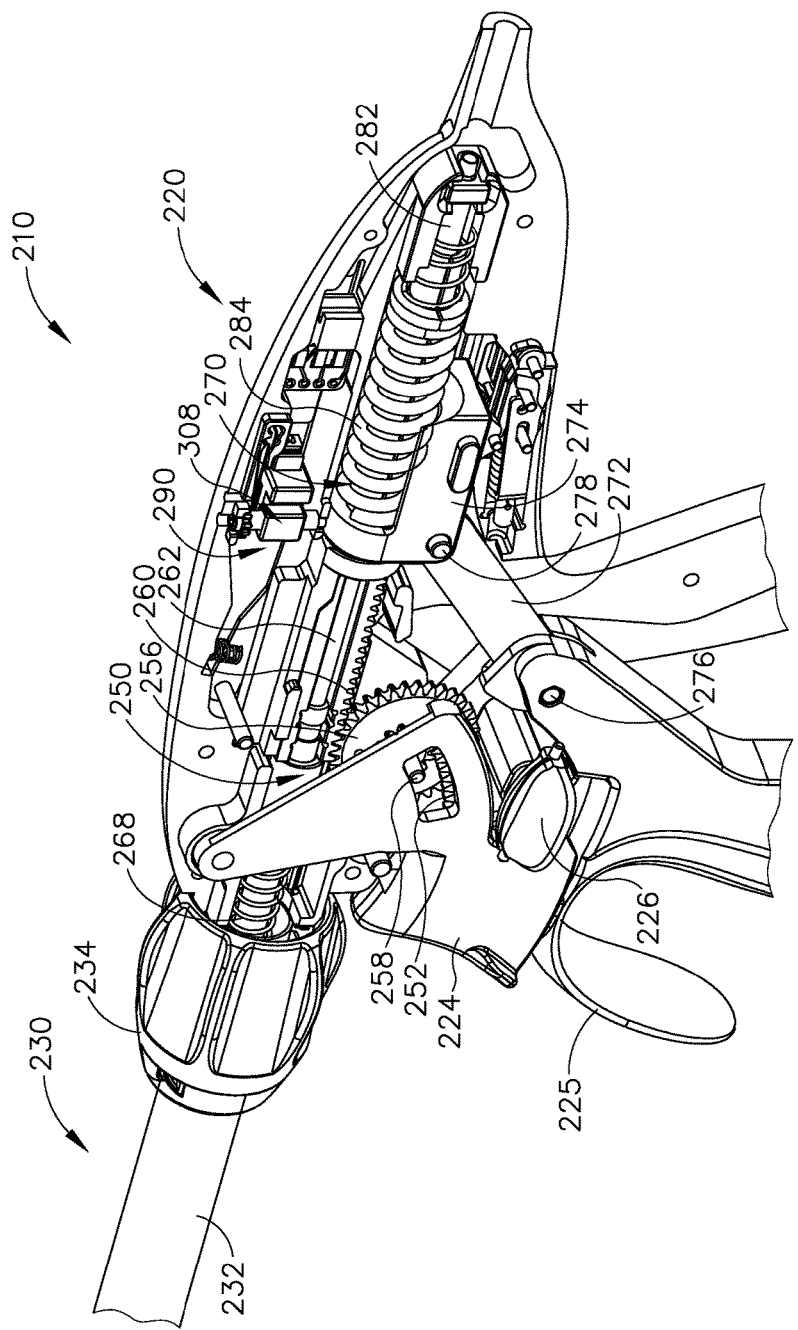
FIG. 10 depicts a detailed perspective view of the instrument of FIG. 9 with one side of a handpiece removed showing a firing beam actuation assembly and a jaw actuation assembly.

FIG. 10 shows a perspective view of electrosurgical instrument (210) with half of handpiece (220) removed. As can be seen, the inside of handpiece (220) comprises a firing beam actuation assembly (250), a jaw actuation assembly (270), and a jaw sensor assembly (290). Generally, firing beam actuation assembly (250) is operable to actuate firing beam (not shown) proximally and distally to cut and/or sever tissue. As will be understood, firing beam actuation assembly (250) is resiliently biased toward the position shown in FIG. 10 such that the firing beam is in a retracted, proximal state. Jaw actuation assembly (270) is operable to actuate end effector (240) to selectively open and close end effector (240). Similarly to firing beam actuation assembly (250), jaw actuation assembly (270) is resiliently biased toward the position shown in FIG. 10 such that end effector (240) is in the open configuration. Although firing beam actuation assembly (250) and jaw actuation assembly (270) are shown as being separately actuatable by blade trigger (224) and jaw trigger (225), respectively, it should be understood that in other examples actuation assemblies (250, 270) may be configured to be actuated by a single trigger. For instance, a single trigger may move through a first range of motion to actuate jaw actuation assembly (270); then through a second range of motion to actuate firing beam actuation assembly (250).

As can best be seen in FIGS. 11-16, firing beam actuation assembly (250) comprises a two rack and pinion mechanism to convert the pivoting motion of blade trigger (224) into linear motion of a firing shaft (262), which ultimately drives the firing beam. In particular, a first rack (252) is attached to blade trigger (224) such that first rack (252) extends proximally and unitarily from blade trigger (224). First rack (252)

is a generally linear gear with a slight curve corresponding to the range of motion of blade trigger (224). First rack (252) meshes with a corresponding first pinion (254). First pinion (254) is coupled to a second pinion (256) by a shaft (258), which may be rotatably fixed within handpiece (220). Pinions (254, 256) rotate together unitarily about the axis of shaft (258), which is rotatably supported in handpiece (220). Second pinion (256) is larger than first pinion (254) such that a mechanical advantage is created to assist in driving the firing beam.

To drive firing shaft (262), which ultimately drives the firing beam, second pinion (256) meshes with a second rack (260). Second rack (260) includes a longitudinally extending channel (264), which has an inner geometry that corresponds to coupling features (266) overmolded to firing shaft (262). Thus, second rack (260) is coupled to firing shaft (262) such that translation of second rack (260) correspondingly translates firing shaft (262). Second rack (260) is resiliently biased to the proximal position shown in FIGS. 11 and 13 by a spring (268) that is oriented coaxially around firing shaft (262).

Jaw actuation assembly (270) comprises rigid link (272) and an actuation block (274). As best seen in FIG. 10, a distal end of rigid link (272) is rotatably secured to jaw trigger (225) by a first pin (276). Similarly, a proximal end of rigid link (272) is rotatably secured to a distal end of actuation block (274) by a second pin (278). Actuation block (274) comprises a distal attachment feature (280), which couples actuation block (274) to a jaw shaft (282). Jaw shaft (282) slidably extends coaxially through firing shaft (262) such that both firing shaft (262) and jaw shaft (282) extend through shaft (230) to end effector (240). Actuation block (274) is resiliently biased toward the distal position shown in FIG. 11 by a spring (284), which is oriented coaxially about jaw shaft (280).

In an exemplary mode of operation, jaw actuation assembly (270) and firing beam actuation assembly (250) begin in the positions shown in FIG. 11. In the positions shown, end effector (240) is in the open position (FIG. 12) and the firing beam is in the retracted proximal position. As can be seen in FIG. 11, second rack (260) is positioned in a proximal most position, while actuation block (274) is positioned in a distal most position.

The firing sequence is initiated when an operator squeezes jaw trigger (225), which pivots jaw trigger (225) relative to handpiece (220) toward pistol grip (222). As can be seen in FIG. 13, actuation of jaw trigger (225) forces rigid link (272) generally proximally, thereby driving actuation block (274) proximally. Proximal translation of actuation block (274) correspondingly causes proximal translation of jaw shaft (282), which ultimately drives end effector (240) to the closed position (FIG. 14) by pivoting second jaw (244) toward first jaw (242). At this stage, jaws (242, 244) may firmly grasp and compress tissue.

With end effector (240) in the closed position, it may next be desirable to advance the firing beam distally. To advance the firing beam distally, the operator may squeeze blade trigger (224) to pivot blade trigger (224) proximally relative to handpiece (220). Pivoting of blade trigger (224) drives first rack (252) proximally. As can be seen in FIG. 15, the proximal movement of first rack (252) correspondingly causes first pinion (254) and second pinion (256) to rotate in the counter clockwise direction. The counter clockwise rotation of first and second pinion (254, 256) drives second rack (260) distally due to engagement between second rack (260) and second pinion (256). Distally advancing second rack (260) drives firing shaft (262) distally to advance the firing beam as illustrated by the arrow in FIG. 16. The distally advancing firing beam will sever the tissue that is compressed between jaws (242, 244).

At any suitable stage during the above described process, the operator may press activation button (226). In certain circumstances, this may provide delivery of RF energy to tissue grasped between jaws (242, 244). By way of example only, the operator may press activation button (226) after jaws (242, 244) are clamping on the tissue but before the firing beam is advanced through the tissue. Controller (82) and/or other features of instrument (210) may be configured such that pressing of activation button (226) does not provide delivery of RF energy unless jaws (242, 244) are already sufficiently clamped on the tissue. Similarly, controller (82) and/or other features of instrument (210) may be configured such that the firing beam may not be advanced distally until the tissue captured by jaws (242, 244) has been sufficiently sealed by application of RF energy.

Figure 17:
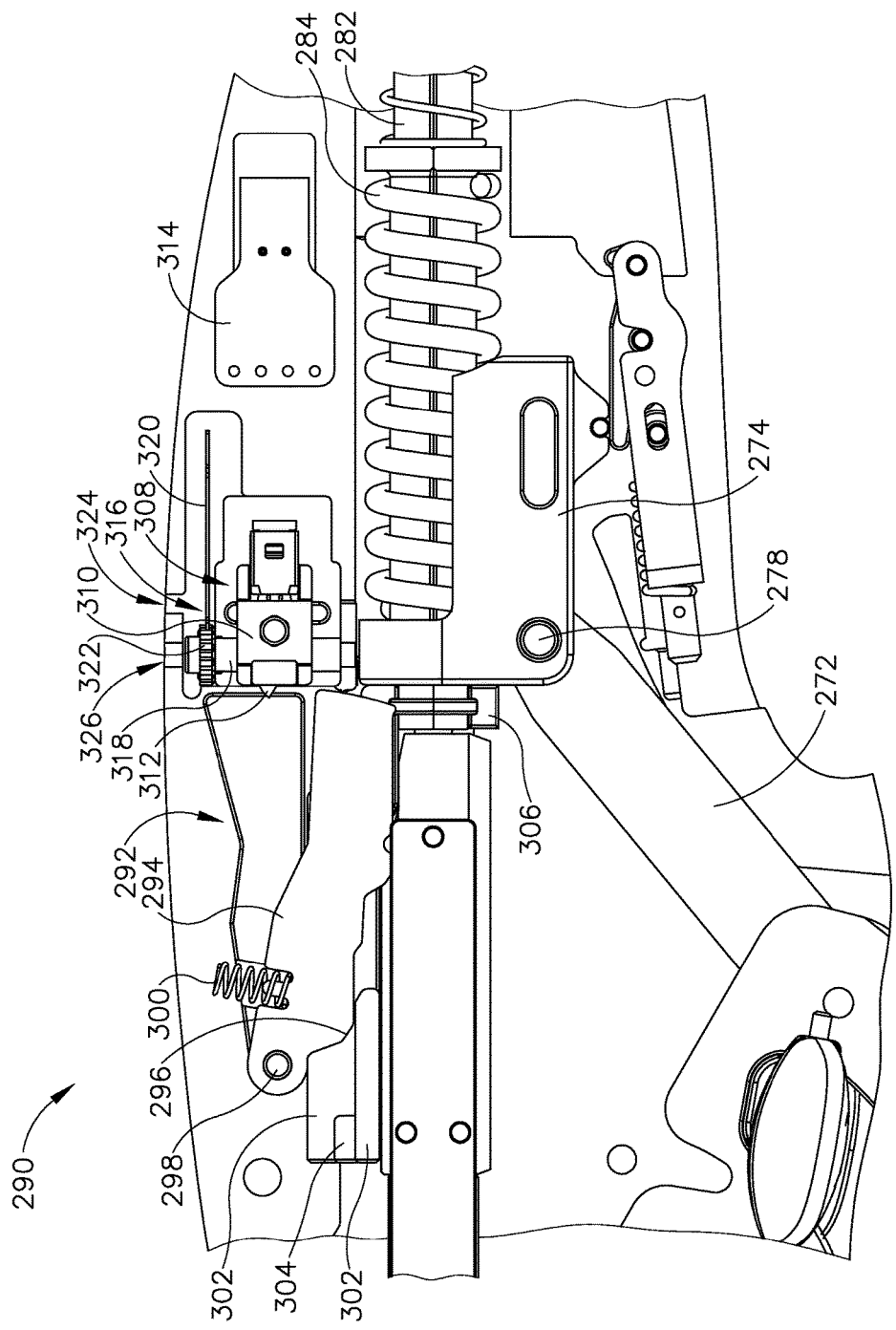
FIG. 17 depicts a detailed side elevational view of the jaw actuation assembly of FIG. 10 with a sensor assembly.
Figure 18:
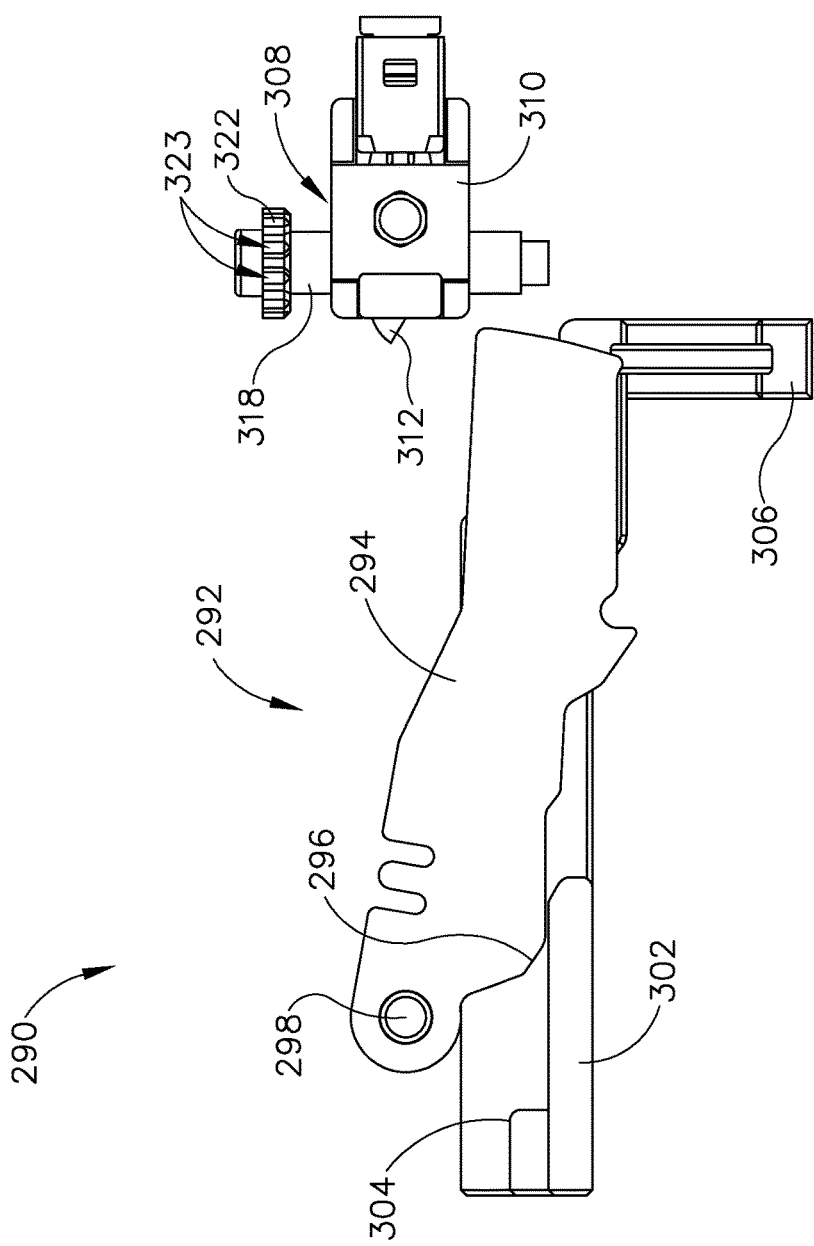
FIG. 18 depicts a side elevational view of the sensor assembly of FIG. 17, in an open circuit configuration.
Figure 19:
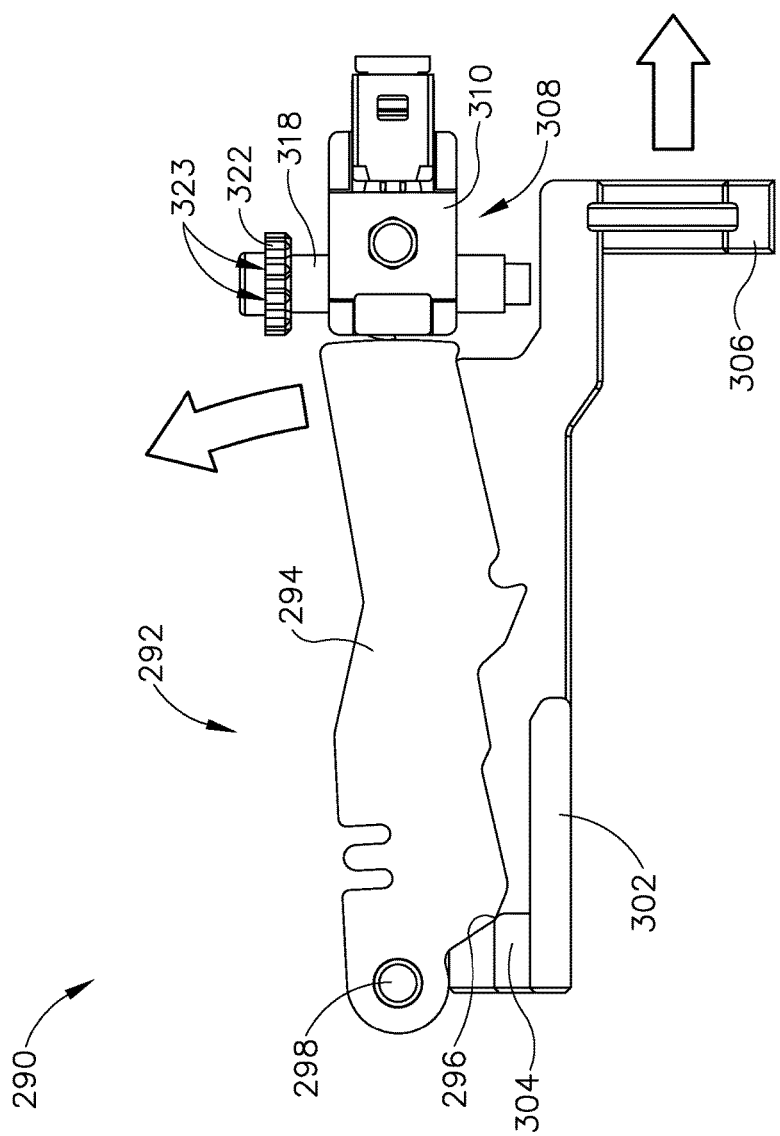
FIG. 19 depicts a side elevational view of the sensor assembly of FIG. 17, in a closed circuit configuration.

FIGS. 17-19 shows a detailed view of jaw sensor assembly (290) positioned within handpiece (220). Generally, jaw sensor assembly (290) is operable to actuate a jaw sensor (308) in response to movement of jaw actuation assembly (270). Jaw sensor assembly (290) comprises a jaw sensor actuation mechanism (292), jaw sensor (308), and an adjustment assembly (316). Jaw sensor actuation mechanism (292) is operable to convert longitudinal translation of jaw actuation assembly (270) into pivotal motion of an arm (294), which ultimately actuates jaw sensor (308). In particular, jaw sensor actuation mechanism (292) comprises an actuator (302), and arm (294). Actuator (302) is attached to jaw shaft (282) via coupling (306) such that actuator (302) translates unitarily with jaw shaft (282). Arm (294) pivots about a pivot pin (298) such that arm (294) is operable to pivot into and out of contact with jaw sensor (308) as will be described in greater detail below. In the present example, arm (294) may function as a lever to create a certain amount of mechanical advantage such that a relatively small movement of jaw shaft (282) results in relatively large movement of arm (294). Arm (294) includes a spring (300), which resiliently biases arm (294) downwardly away from jaw sensor (308). Both actuator (302) and arm (294) comprise complementary pivot features (296, 304). As will be described in greater detail below, pivot feature (304) of actuator (302) is configured to engage pivot feature (296) of arm (294) as actuator (302) is driven proximally by jaw shaft (282).

Jaw sensor (308) is similar to jaw sensor (146) described above. In particular, jaw sensor (308) comprises a sensor body (310) and a movable protrusion (312). Movable protrusion (312) is resiliently biased to protrude outwardly from sensor body (310), as shown in FIG. 17. In the present example, jaw sensor (308) is a binary sensor such that actuation of movable protrusion (312) by arm (294) results in jaw sensor (308) opening or closing an electronic circuit. In other examples, jaw sensor (308) may be configured as a bypass switch or any other suitable switch as will be apparent to those of ordinary skill in the art in view of the teachings herein. Jaw sensor (308) may be in communication with sensor circuitry (314), which may communicate the state of jaw sensor (308) to a controller (not shown) such as controller (82). Such operation of jaw sensor (308) will be described in greater detail below. Those of ordinary skill in the art will immediately recognize the various kinds of form that jaw sensor (308) may take, including but not limited to a contact switch, a reed switch, a hall effect sensor, capacitive sensor, etc.

Sensor body (310) is secured to adjustment assembly (316). In particular and as will be described in greater detail below, adjustment assembly (316) may permit vertical adjustment of sensor body (310) to thereby adjust the vertical positioning of movable protrusion (312), which may in turn adjust the effective sensitivity of sensor (308). Adjustment assembly (316) comprises an adjustment mechanism (318) a lock plate (320), and a lock gear (322). In some examples, adjustment mechanism (318) comprises a threaded cylinder similar to a lead screw or worm gear such that adjustment mechanism (318) may engage corresponding threading inside a bore (not shown) extending vertically through sensor body (310). Thus, with adjustment mechanism (318) serving as a lead screw and sensor body (310) serving as a nut, rotation of adjustment mechanism (318) provides vertical movement of sensor body (310). Of course, adjustment mechanism (318) may comprise any other mechanism suitable to adjust the vertical height of sensor body (310) as will be apparent to those of ordinary skill in the art in view of the teachings herein.

Lock plate (320) comprises a thin plate that is formed like a leaf spring. A proximal end of lock plate (320) is secured to handpiece (220) such that the proximal end of lock plate (320) is fixed relative to handpiece (220). The distal end of lock plate (320) is free to move relative to handpiece (220). The distal end of lock plate (320) comprises a plurality of teeth (321), which are configured to engage lock gear (322) as will be described in greater detail below. Lock plate (320) is resiliently biased to assume a straight configuration (FIGS. 17 and 20); yet may be deflected to assume a non-straight configuration (FIG. 21). In the straight configuration, lock plate (320) engages lock gear (322). In the deflected or non-straight configuration, lock plate (320) is not engaged with lock gear (322).

Lock gear (322) is secured coaxially around adjustment mechanism (318). Lock gear (322) and adjustment mechanism (318) are secured together such that lock gear (322) and adjustment mechanism (318) rotate together unitarily about the longitudinal axis shared by lock gear (322) and adjustment mechanism (318). Although lock gear (322) and adjustment mechanism (318) are described separately, it should be understood that lock gear (322) and adjustment mechanism (318) may either be separate parts coupled together or a unitary part. Lock gear (322) comprises several protrusions (323) that extend outwardly from lock gear (322) like an angularly spaced array of teeth. As will be described in greater detail below, protrusions (323) may be engaged by teeth (321) of lock plate (320) to lock rotational motion of adjustment mechanism (318), thereby preventing adjustment of the vertical position of sensor body (310).

FIGS. 18-19 show an exemplary mode of operation of jaw sensor assembly (290). In particular, jaw sensor assembly (290) may begin in the position as shown in FIG. 18, which shows jaw sensor assembly (290) isolated from the rest of electrosurgical instrument (210). As can be seen in FIG. 18, actuator (302) of jaw sensor actuation mechanism (292) is distal relative to arm (294) of jaw sensor actuation mechanism (292). It should be understood that in this position, jaw actuation assembly (270) corresponds to the distal most position such that end effector (240) is in the open position. In other words, jaw (244) is pivoted away from jaw (242) as shown in FIG. 12. As jaw actuation assembly (270) closed (as described above), pivoting jaw (244) toward jaw (242), actuator (302) of jaw sensor actuation mechanism (292) is advanced proximally via jaw shaft (282). As can be seen in FIG. 19, advancement of actuator (302) causes pivot feature (304) of actuator (302) to cam against pivot feature (296) of arm (294). Pivot features (304, 296) work cooperatively to drive arm (294) pivotally about pivot pin (298) such that arm (294) pivots into engagement with movable protrusion (312) of jaw sensor (308).

Once arm (294) engages moveable protrusion (312) of jaw sensor (308), jaw sensor (308) may switch an electronic circuit to an open or closed state, communicating such a change to sensor circuitry (314). It should be understood that such a change in state may correspond to a specific pivotal position of second jaw (244) relative to first jaw (242). In some examples, such a positioning of second jaw (244) may correspond to a 0.01 inch gap between second jaw (244) and first jaw (242). In other words, jaw sensor assembly (290) may be configured such that jaw sensor (308) is activated when second jaw (244) reaches a state of closure where jaws (242, 244) are separated by a gap of approximately 0.01 inches. Of course, any other gap value may be utilized as will be apparent to those of ordinary skill in the art in view of the teachings herein. In addition or in the alternative, jaw sensor assembly (290) may be configured such that jaw sensor (308) is activated when second jaw (244) reaches a state of closure where jaws (242, 244) define an angle of approximately 10 degrees or less. Of course, any other degree of separation may be utilized as will be apparent to those of ordinary skill in the art in view of the teachings herein. The controller (82) may adjust RF energy supplied to end effector (240) to facilitate proper sealing of tissue based on activation of jaw sensor (308) as described above with respect to electrosurgical instrument (110).

Controller (82) may be configured to respond to changes in state of jaw sensor (308) communicated to controller (82). In particular, when controller (82) receives a signal from jaw sensor (308) corresponding to the closed position of second jaw (244), controller (82) may be converted into a ready state where subsequent activation of button (226) provides RF energy to jaws (242, 244). Conversely, if button (226) is activated before jaw sensor (308) indicates a sufficiently closed position of jaw (244), controller (82) may be prevented from providing RF energy to jaws (242, 244). In addition or in the alternative, controller (82) may activate a user feedback feature (e.g., audible tone, visible light, etc.) to alert the operator that jaw (244) is insufficiently closed if the operator activates button (226) before jaw sensor (308) indicates a sufficiently closed position of jaw (244). In addition to or as an alternative to the foregoing, jaw sensor (308) may be configured to detect closure of jaws (242, 244) in the absence of tissue between jaws (242, 244). In other words, sensor (308) and controller (82) may be operable to determine that jaws (242, 244) have been closed without tissue being positioned between jaws (242, 244). In such instances, controller (82) may prevent the delivery of RF energy to jaws (242, 244). In addition or in the alternative, controller (82) may activate a user feedback feature (e.g., audible tone, visible light, etc.) to alert the operator that end effector (240) needs to be repositioned in order to position tissue between jaws (242, 244) before jaws (242, 244) may deliver RF energy.

It should be understood that the pivotal movement of lever arm (294) is proportional to the pivotal movement of jaw (244). Although jaw sensor (308) is described herein as being binary in nature, it should be understood that in other examples jaw sensor (308) may be non-binary having a plurality of outputs to communicate different amount of closure of second jaw (244). In such examples, controller (82) may be responsive to varying degrees of input from jaw sensor (308) indicating differing amounts of closure of second jaw (244) such that RF power may be altered depending on different amounts of closure of second jaw (244). For instance, if jaw sensor (308) indicates a relatively wide separation of jaw (244) from jaw (242) when button (226) is activated (e.g., indicating a relatively thick bundle of tissue), controller (82) may provide a relatively high level of RF energy to jaws (242, 244). If jaw sensor (308) indicates a relatively small separation of jaw (244) from jaw (242) when button (226) is activated (e.g., indicating a relatively thin bundle of tissue), controller (82) may provide a relatively low level of RF energy to jaws (242, 244). It should also be understood that controller may (82) provide a control algorithm that factors in feedback from jaw sensor (308) and feedback indicating an electrical resistance of tissue in jaws (242, 244). Various suitable ways in which the electrical resistance of tissue may be sensed will be apparent to those of ordinary skill in the art in view of the teachings herein. Of course, controller (82) may be responsive to jaw sensor (308) and/or other sources of feedback in any other suitable way as will be apparent to those of ordinary skill in the art in view of the teachings herein.

In some instances, it may be desirable to adjust the vertical positioning of jaw sensor (308). For instance, it is desirable for arm (294) of jaw sensor actuation mechanism (292) to engage movable protrusion (312) of jaw sensor (308) as second jaw (244) of end effector (240) reaches a predetermined pivotal point. However, due to variations in the manufacturing process, such a relationship may not initially exist. In addition or in alternative, it may also be desirable to adjust the vertical positioning of jaw sensor (308) in the field to modify the tissue sealing properties of electrosurgical instrument (210).

Figure 20:
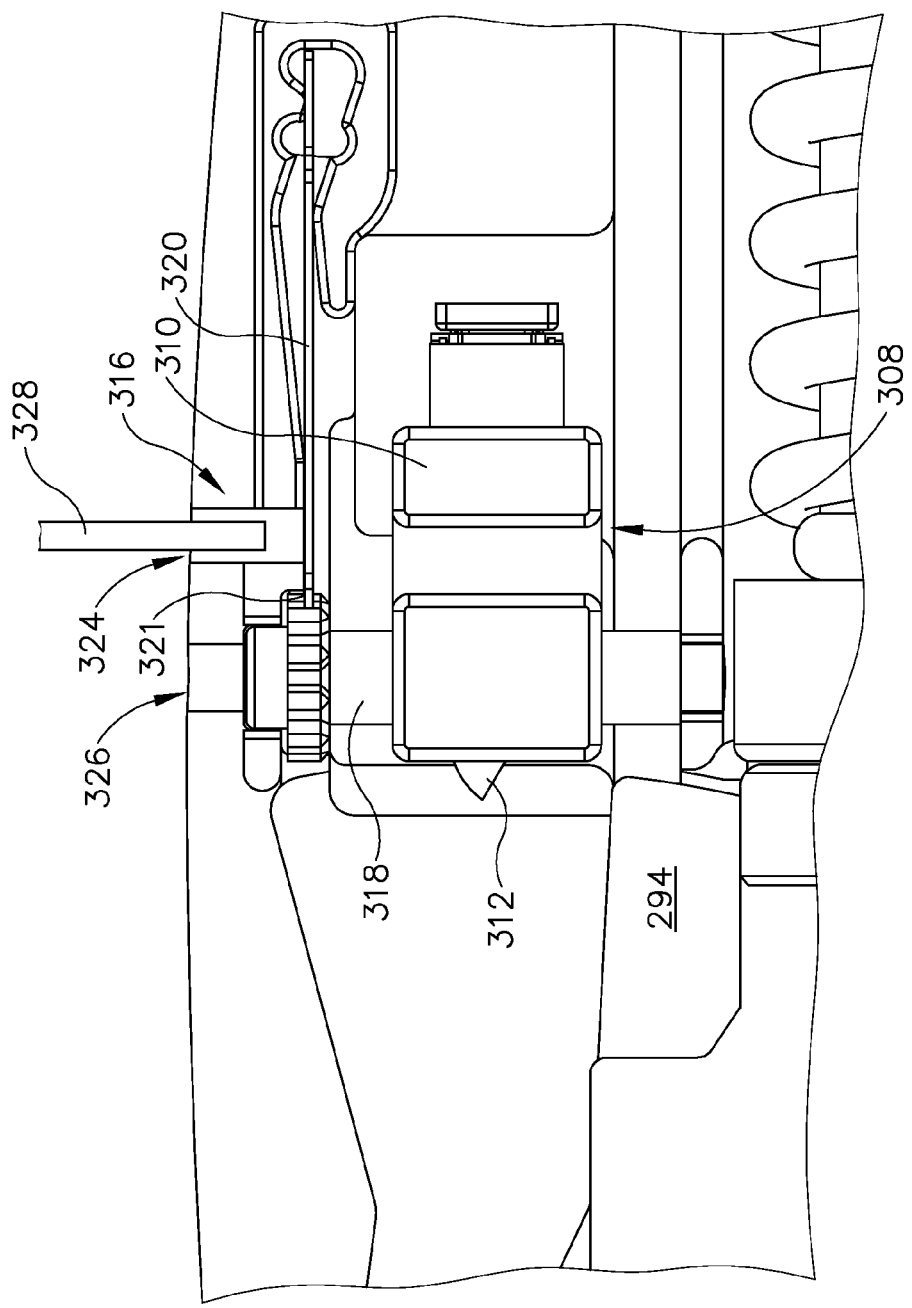
FIG. 20 depicts a detailed side elevational view of the sensor assembly of FIG. 17 with an adjustment assembly in a locked position.
Figure 21:
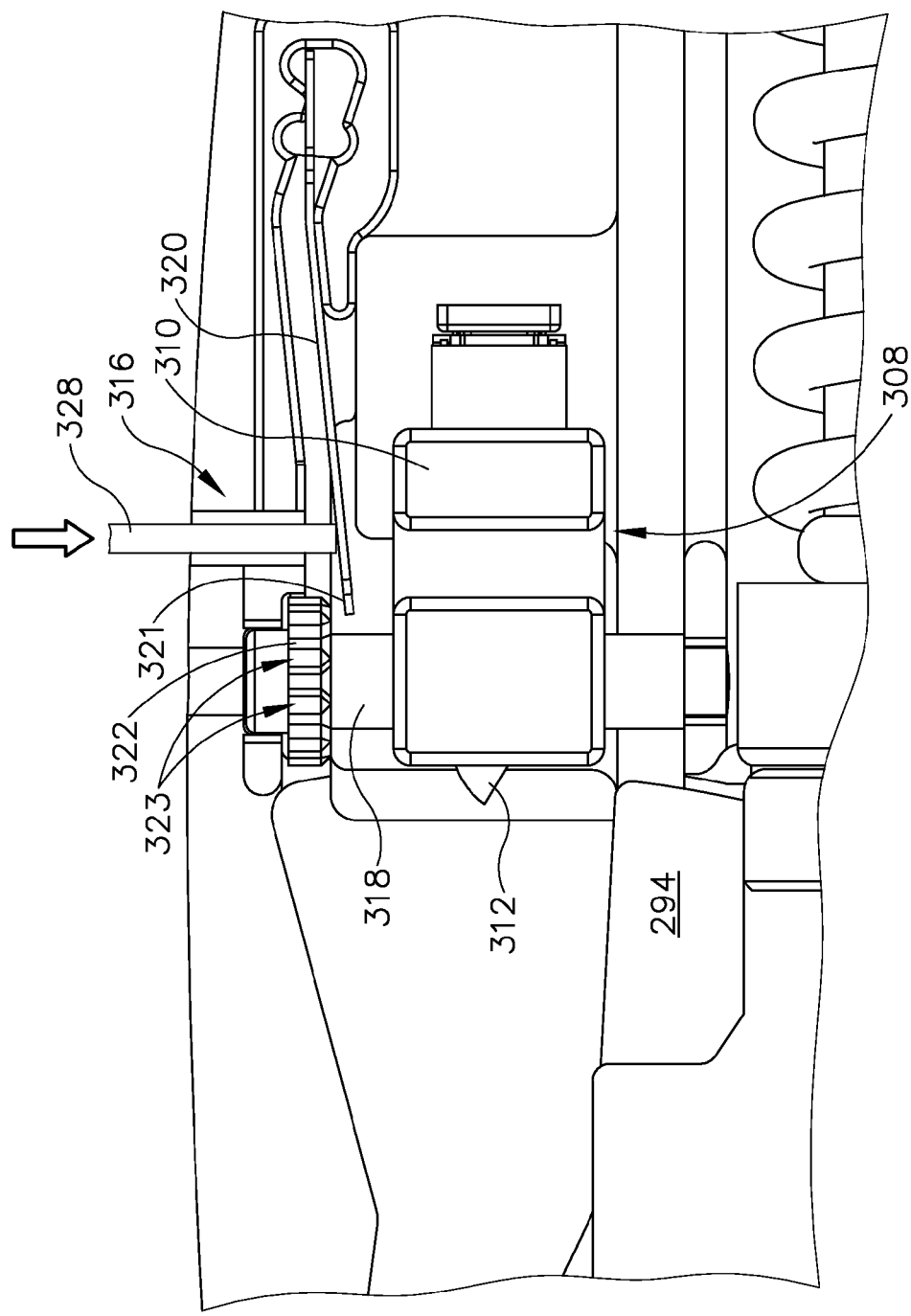
FIG. 21 depicts a detailed side elevational view of the adjustment assembly of FIG. 20 with the adjustment assembly in an unlocked position.
Figure 22:
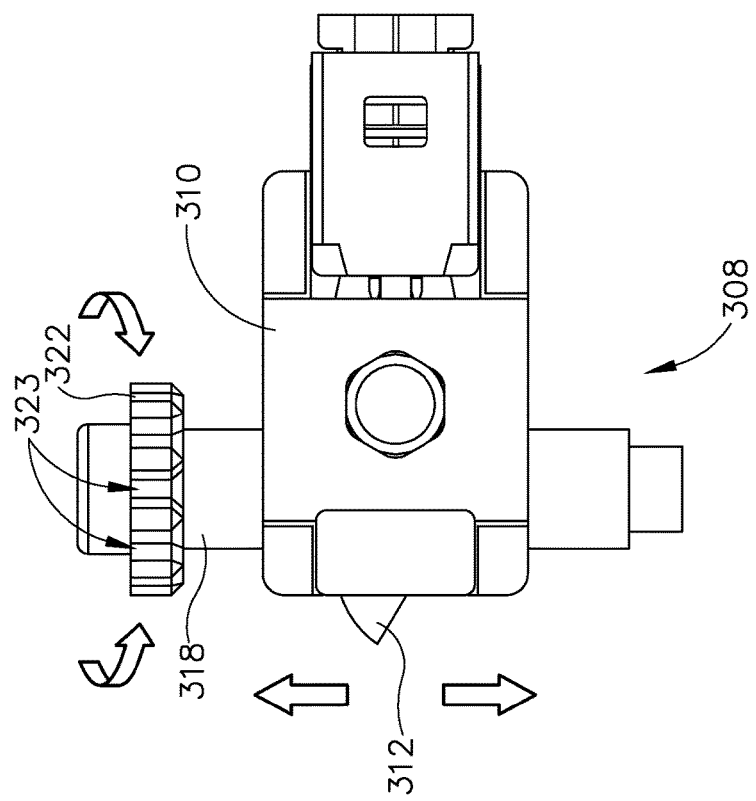
FIG. 22 depicts a side elevational view of an adjustable sensor of the sensor assembly of FIG. 17.

FIGS. 20-22 show an exemplary procedure for adjusting the vertical positioning of jaw sensor (308). In particular, FIG. 20 shows jaw sensor assembly (290) prior to being adjusted. As can be seen, lock plate (320) of adjustment assembly (316) is initially in engagement with lock gear (322) of adjustment assembly (316). In such a position, adjustment assembly (316) is locked such that adjustment mechanism (318) of adjustment assembly (316) is prevented from rotating. As can be seen in FIG. 21, a rod (328) or other similarly shaped device may be inserted through a first hole (324) in handpiece (220). Rod (328) engages lock plate (320) and pushes lock plate (320) out of engagement with lock gear (322). With lock plate (320) out of engagement with lock gear (322), adjustment mechanism (318) may be rotated (FIG. 22). As described above, adjustment mechanism (318) may include threading that will cause sensor body (310) to translate vertically as adjustment mechanism (318) is rotated. In such an example, adjustment mechanism (318) may include a feature on the upper surface such as a hex bore so that a tool may be inserted through a second hole (326) in handpiece (220) to rotate adjustment mechanism (318). Once the operator has achieved a desired vertical positioning of sensor body (310), the operator may release lock plate (320). The resilient bias of lock plate (320) will then urge lock plate (320) back to the position shown in FIG. 20, whereby the vertical position of sensor body (310) is locked. Other suitable adjustment mechanisms (318) that may be utilized will be apparent to those of ordinary skill in the art in view of the teachings herein. It should also be understood that, in versions of adjustment mechanism (318) having a threaded feature, the threading on such a threaded feature may have a relatively fine pitch in order to provide fine adjustments of sensitivity.

B. Exemplary Electrosurgical Instrument with Jaw Sensor Activated by Downwardly Pivoting Arm FIGS. 23-30 show another exemplary electrosurgical instrument (410) with a jaw sensor (506) integrated into a jaw actuation assembly (490). Except as otherwise described below, electrosurgical instrument (410) is substantially the same as electrosurgical instrument (10) described above. Electrosurgical instrument (410) of the present example includes a handpiece (420), a shaft (430) extending distally from handpiece (420), and end effector (440) disposed at a distal end of shaft (430). Handpiece (420) of the present example includes a pistol grip (422), pivoting trigger (424), and an activation button (426). Trigger (424) is pivotable toward and away from pistol grip (422) to selectively actuate end effector (440). Activation button (426) is operable to selectively activate RF circuitry that is in communication with end effector (440).

Shaft (430) of the present example includes a rigid outer sheath (432) without an articulation section, though it should be understood that some variations may include an articulation section. Shaft (430) is rotatable about the longitudinal axis defined by sheath (432), relative to handpiece (420), via a knob (434). Such rotation may provide rotation of end effector (440) and shaft (430) unitarily.

End effector (440) is similar to end effector (40) described above Like end effector (40), end effector (440) comprises a first jaw (442) and a second jaw (444). First jaw (442) is fixed relative to shaft (430) such that first jaw (442) remains stationary as end effector (440) actuates. Second jaw (444) is pivotable relative to first jaw (442) such that second jaw (444) transitions between an open and closed position as end effector (440) is actuated. Second jaw (444) may be pivoted in any suitable way as will be apparent to those of ordinary skill in the art in view of the teachings herein. Instrument (410) further includes a firing beam (not shown) that is operable to translate through end effector (440) to thereby sever tissue captured between jaws (442, 444). By way of example only, such a firing beam may be configured similar to firing beam (60), similar to firing beam (70), or in any other suitable fashion.

Figure 23:
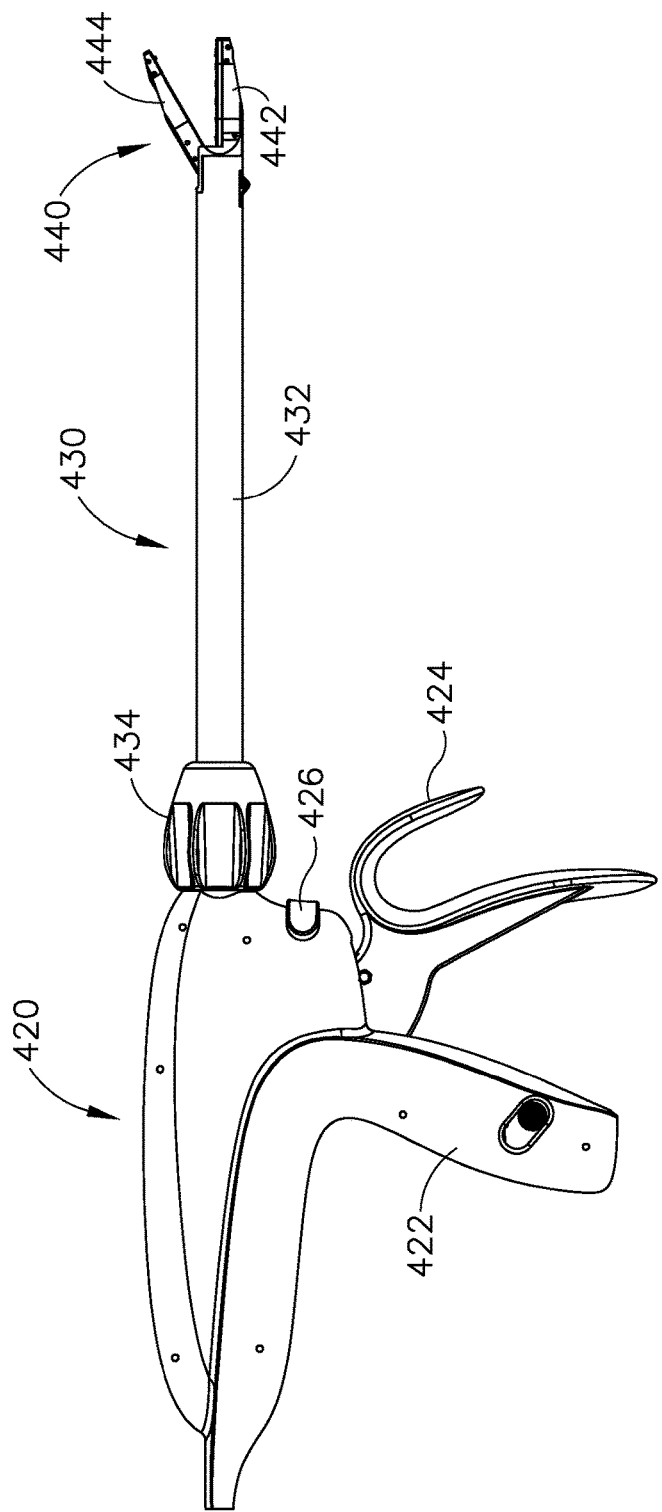
FIG. 23 depicts a side elevational view of another exemplary alternative electrosurgical medical instrument.
Figure 24A:
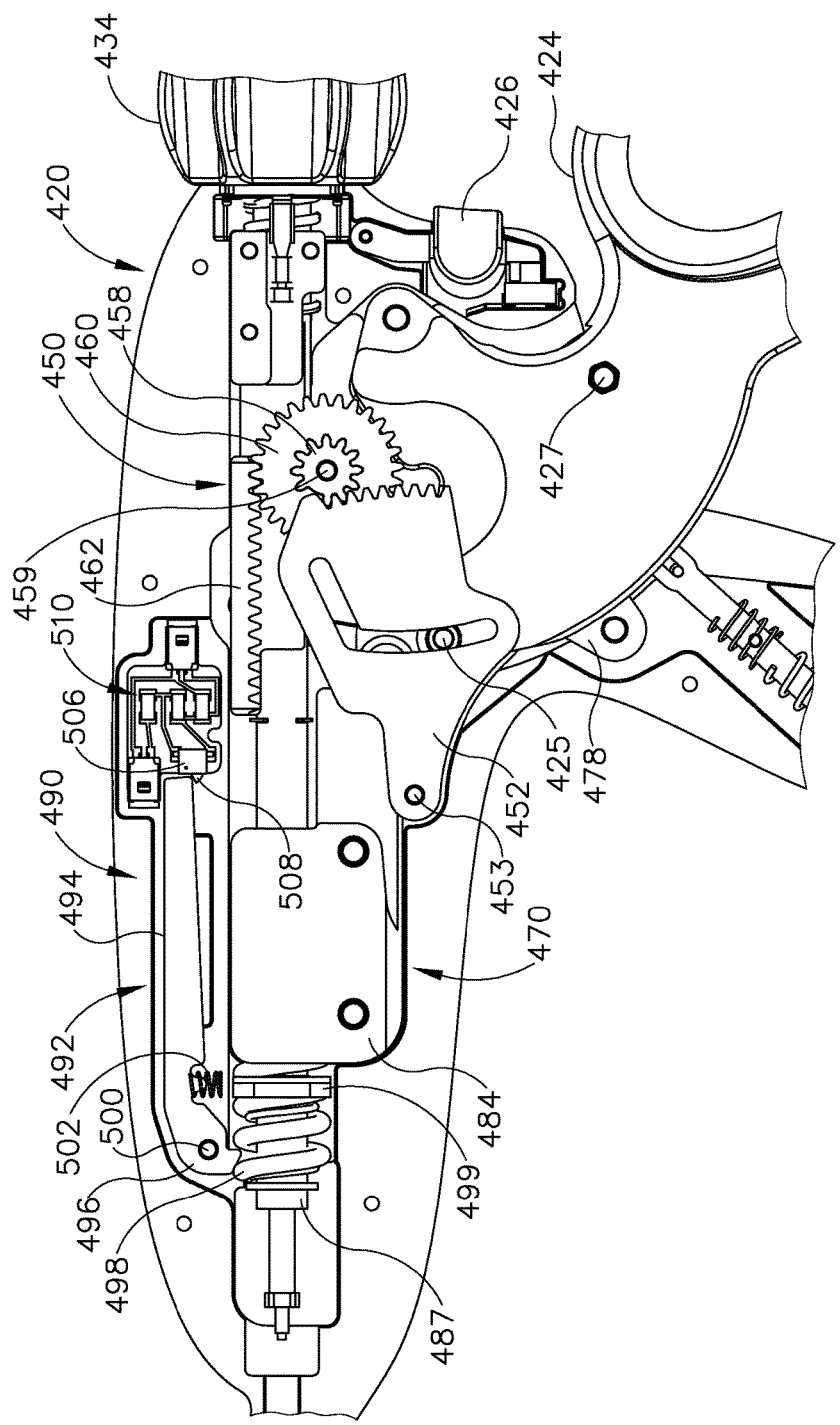
FIG. 24A depicts a detailed side elevational view of the instrument of FIG. 23 with one side of a handpiece removed showing a firing beam actuation assembly, a jaw actuation assembly, and a sensor assembly.
Figure 24B:
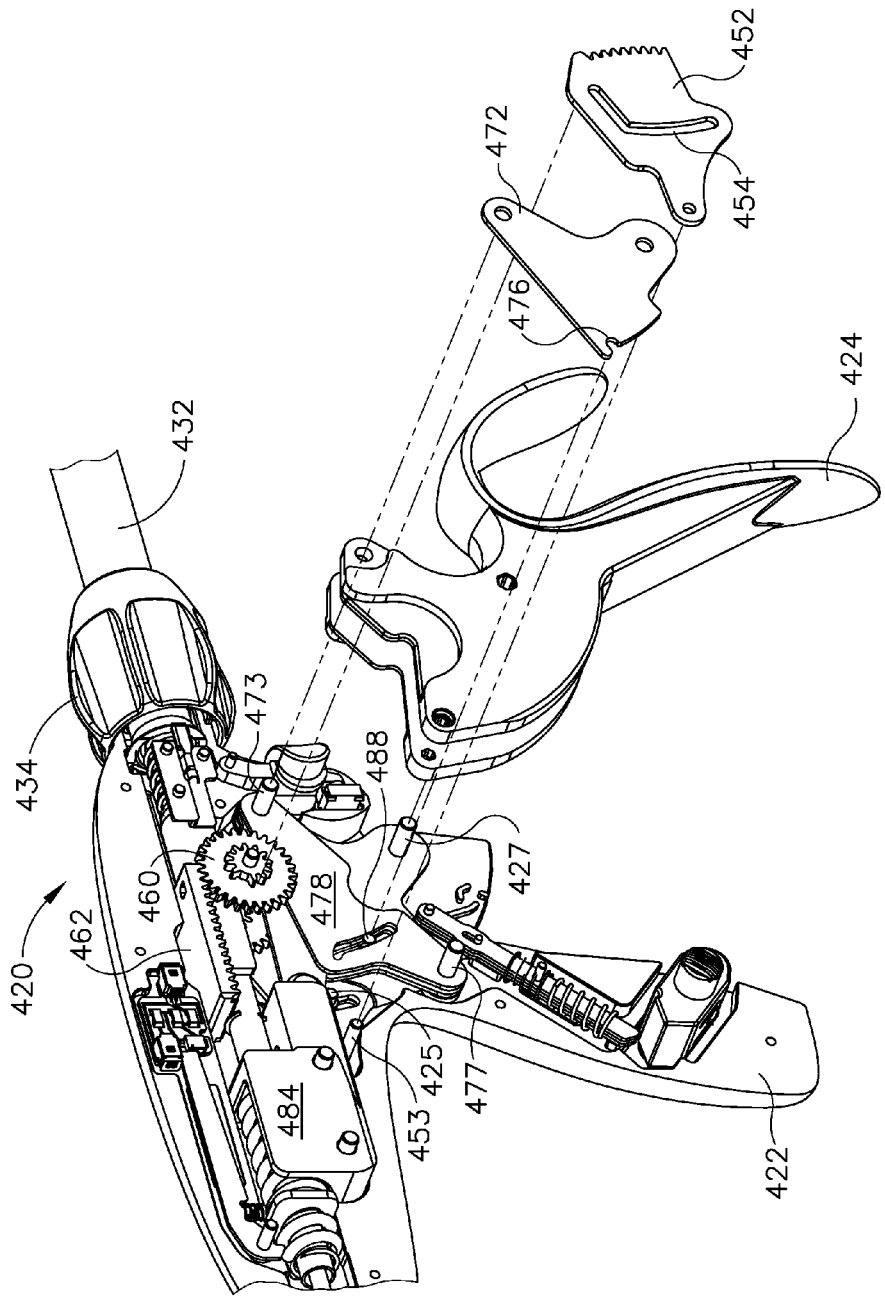
FIG. 24B depicts a partially exploded perspective view of the instrument of FIG. 23.

FIG. 24A shows a side view of electrosurgical instrument (410) with half of handpiece (420) removed. FIG. 24B shows a partially exploded view of the same components, with an upper/proximal portion of trigger (424) broken away to reveal additional internal components of handpiece (420). As can be seen, the inside of handpiece (420) comprises a firing beam actuation assembly (450), a jaw actuation assembly (470), and a jaw sensor assembly (490). Jaw actuation assembly (470) is operable to actuate end effector (440) to selectively drive jaw (444) toward and away from jaw (442). Jaw actuation assembly (470) is resiliently biased toward the distal position shown in FIG. 24 such that jaw (444) is resiliently biased toward the open position shown in FIG. 23. Firing beam actuation assembly (450) is operable to actuate firing beam (not shown) proximally and distally to cut and/or sever tissue that is captured between jaws (442, 444). Firing beam actuation assembly (450) is resiliently biased toward the position shown in FIG. 24 such that the firing beam resiliently biased toward a retracted, proximal state. It should be understood that firing beam actuation assembly (450) and jaw actuation assembly (470) are actuatable by a single trigger (424) in this example. As will be understood from further teachings below, trigger (424) is a two stage mechanism, such that movement of trigger (424) through a first range of motion causes closure of jaws (442, 444); while further movement of trigger (424) through a second range of motion causes distal advancement of the firing beam.

Figure 25:
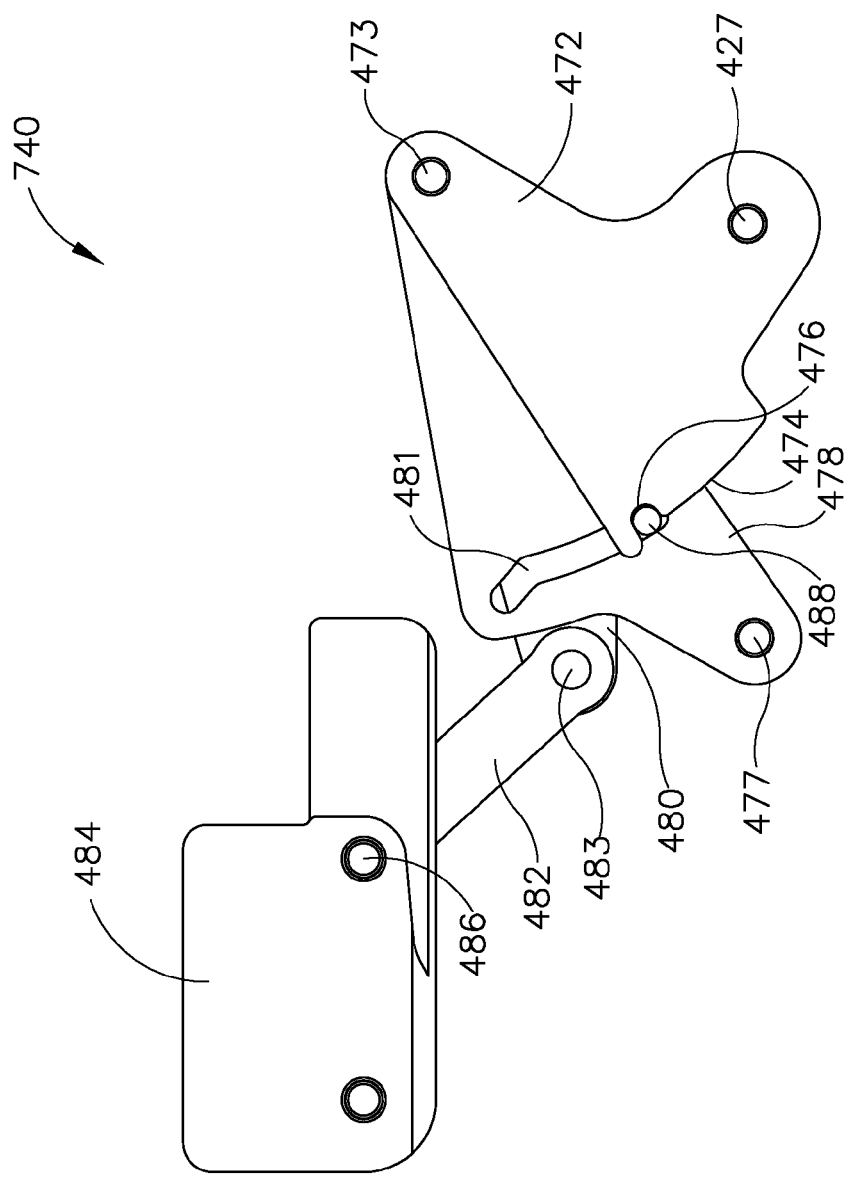
FIG. 25 depicts a side elevational view of the jaw actuation assembly of FIG. 24A with the jaw actuation assembly in an initial position.
Figure 26:
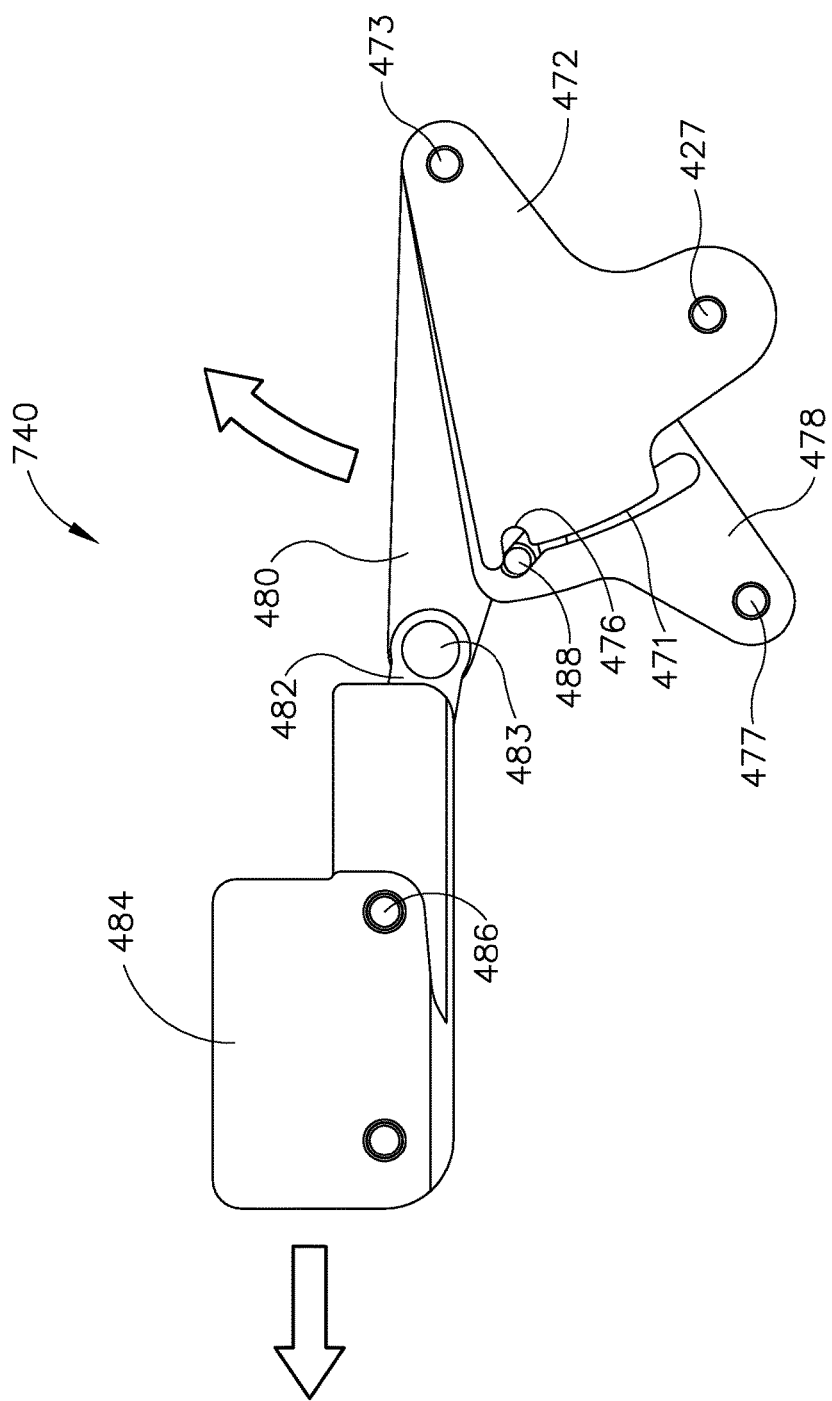
FIG. 26 depicts a side elevational view of the jaw actuation assembly of FIG. 24A with the jaw actuation assembly in an actuated position.

FIGS. 25 and 26 show jaw actuation assembly (470) isolated from the rest of electrosurgical instrument (410). In the present example, jaw actuation assembly (470) comprises two drive plates (472), two guide plates (478), a first linkage (480), and a second linkage (482). Although jaw actuation assembly (470) is described as having two drive plates (472) and two guide plates (478), it should be understood that drive plates (472) and guide plates (478) are stacked symmetrically such that only a single drive plate (472) and a single guide plate (478) is visible. In other words, plates (472, 478) are arranged such that first linkage (480) is positioned between two guide plates (478); and the combination of guide plates (478) and first linkage (480) is positioned between two drive plates (472).

Drive plate (472) is rotatable about drive plate pin (473), which is fixedly secured within handpiece (420). Drive plate (472) comprises a curved portion (474) and a notch (476). Drive plate (472) is connected to trigger (424) via second trigger pin (427). Thus, trigger (424) is operable to pivot drive plate (472) about drive plate pin (473) as trigger (424) is pivoted toward and away from pistol grip (422). As will be described in greater detail below, curved portion (474) and notch (476) work cooperatively to permit the two stage actuation of trigger (424) as drive plate (472) pivots about drive plate pin (473).

Guide plate (478) is substantially fixed within handpiece (420) by drive plate pin (473) and guide plate pin (477). Pins (473, 477) are fixedly secured within handpiece (420). Guide plate (478) comprises a guide plate channel (481), which receives a drive pin (488). As will be described in greater detail below, guide plate (476) and drive plate (472) work cooperatively to actuate drive pin (488) upwardly along guide plate channel (481) when trigger (424) is pivoted toward pistol grip (422).

First linkage (480) extends proximally from drive plate pin (473) and includes a notch (not shown) similar to notch (476). First linkage (480) is pivotable about drive plate pin (473). The proximal end of first linkage (480) is pivotally attached to second linkage (482) via a connector pin (483). As will be described in greater detail below, first linkage (480) works cooperatively with drive plate (472) and guide plate (476) to actuate drive block (484) proximally in response to pivotal movement of trigger (424) toward pistol grip (422).

Second linkage (482) extends between first linkage (480) and drive block (484). As described above, second linkage (482) is pivotally coupled with first linkage (480) via connector pin (483). Second linkage (482) is also pivotally coupled with drive block (484) via pin (486). Drive block (484) is secured to a fixed track within handpiece (420) such that drive block (484) is only free to translate distally and proximally. Accordingly, and as will be described in greater detail below, second linkage (482) is operable to translate drive block (484) proximally as first linkage (480) is driven upwardly by drive pin (488).

Figure 29:
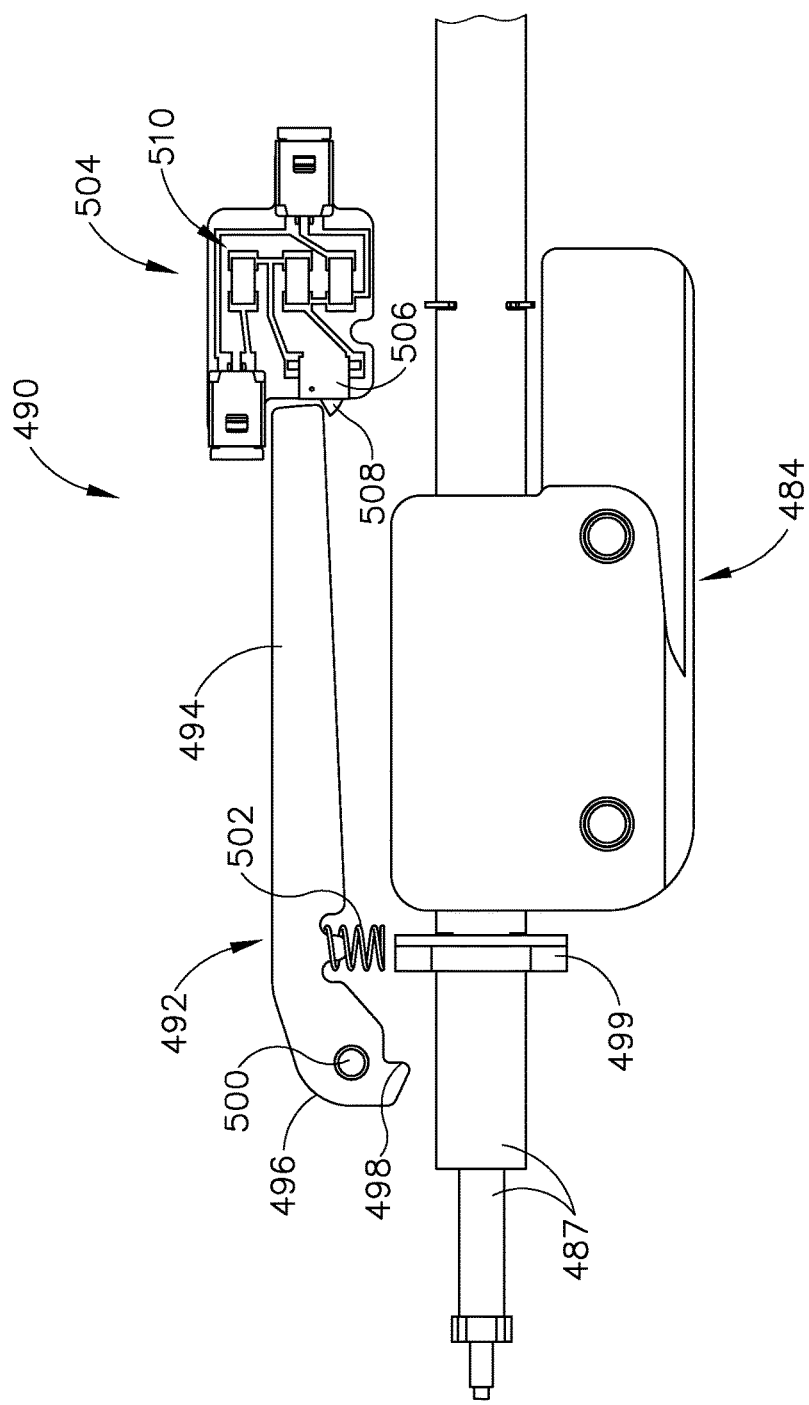
FIG. 29 depicts a side elevational view of the jaw actuation assembly and sensor assembly of FIG. 24A, the sensor assembly in an open circuit configuration with the jaw actuation assembly in the initial position.
Figure 30:
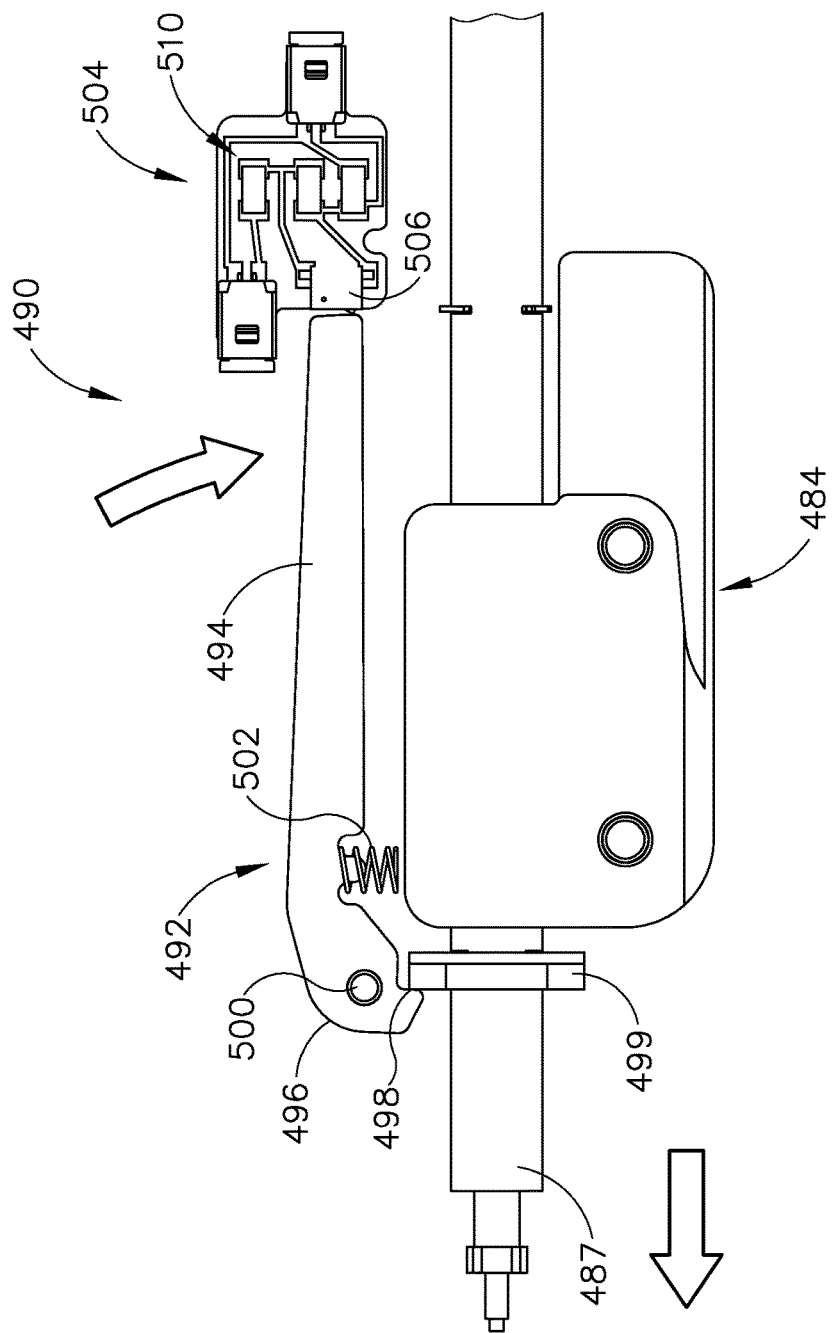
FIG. 30 depicts a side elevational view of the jaw actuation assembly and the sensor assembly of FIG. 24A, the sensor assembly in a closed circuit configuration with the jaw actuation assembly in the actuated position.
Figure 31:
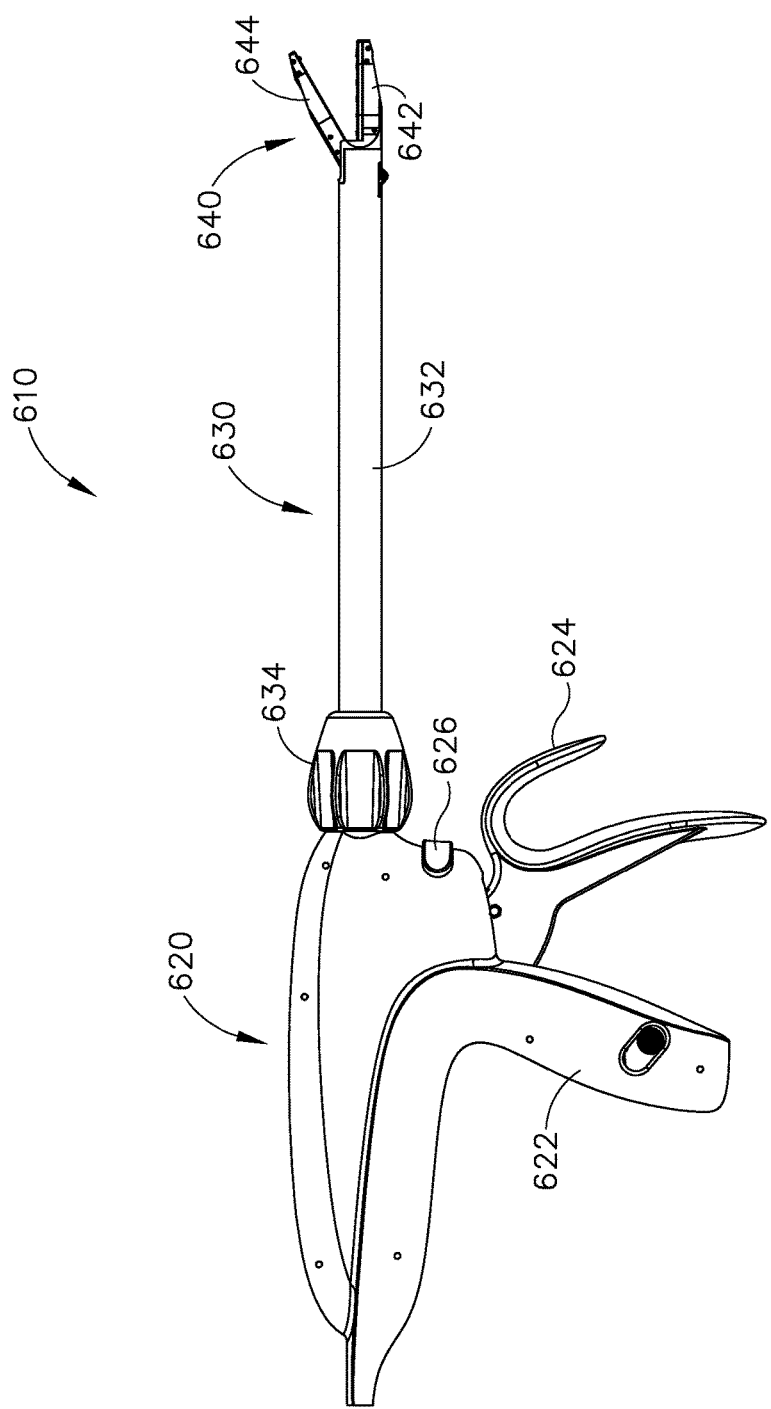
FIG. 31 depicts a side elevational view of another exemplary alternative electrosurgical medical instrument.

As best seen in FIGS. 24A and 29-30, drive block (484) is fixedly secured to a jaw shaft (487). Jaw shaft (487) is configured to drive jaw (444) toward jaw (442) in response to proximal movement of jaw shaft (487); and to drive jaw (444) away from jaw (442) in response to distal movement of jaw shaft (487). Various suitable ways in which jaw shaft (487) may be coupled with jaw (444) will be apparent to those of ordinary skill in the art in view of the teachings herein.

An exemplary mode of operation of jaw actuation assembly (470) can be seen by comparing FIGS. 25 and 26. In particular, the initial position of jaw actuation assembly (470) is shown in FIG. 25. In the initial position, drive block (484) is in its distal most position. It should be understood that the distal most position of drive block (484) corresponds to trigger (424) being in an initial un-actuated state (as shown in FIG. 23) jaw (444) being in an open position (as also shown in FIG. 23). The operator may close jaw (444) by squeezing trigger (424) toward pistol grip (422). This pivotal actuation of trigger (424) causes drive plate (472) to immediately begin pivoting about drive plate pin (473); due to trigger pin (427) coupling trigger (424) with drive plate (472). As drive plate (472) pivots about pin (473), drive pin (488) is held within notch (476) of drive plate (472) by guide plate (478), such that drive plate (472) drives drive pin (488) upwardly through guide plate channel (481). Drive pin (488) drives first linkage (480) upwardly as drive pin (488) is driven upwardly by drive plate (472), such that first linkage (480) pivots about pin (473). As first linkage (480) is driven upwardly by drive pin (488), second linkage (482) rotates away from first linkage (480) to actuate drive block (484) proximally.

As trigger (424) completes pivotal movement toward pistol grip (422) through a first range of motion, drive block (484) reaches its proximal most position as shown in FIG. 26. To permit continued actuation of trigger (424) the upper portion of guide channel (481) shifts proximally from its initial path. This portion of guide channel (481) permits drive pin (488) to move proximally out of notch (476) such that drive pin (488) rides along curved portion (474) of drive plate (472) instead of being driven by notch (476) of drive plate (472). With drive pin (488) riding along curved portion (474) of drive plate (472), drive plate (472) can continue pivoting relative to drive plate pin (473) without moving other components of jaw actuation assembly (470). Further actuation of trigger (424) through a second range of motion toward pistol grip (422) may then be used to advance firing beam as described below. It should be understood that engagement between drive pin (488) and curved portion (474) of drive plate (472) will positively hold jaw (444) in a closed position as trigger (424) moves through the second range of motion and/or as trigger (424) is held in place after moving through the second range of motion. It should also be understood that, as trigger (424) is subsequently pivoted back toward the initial position shown in FIG. 23, drive pin (488) will eventually re-engage notch (476) and thereby drive jaw (444) back to the open position.

Figure 27:
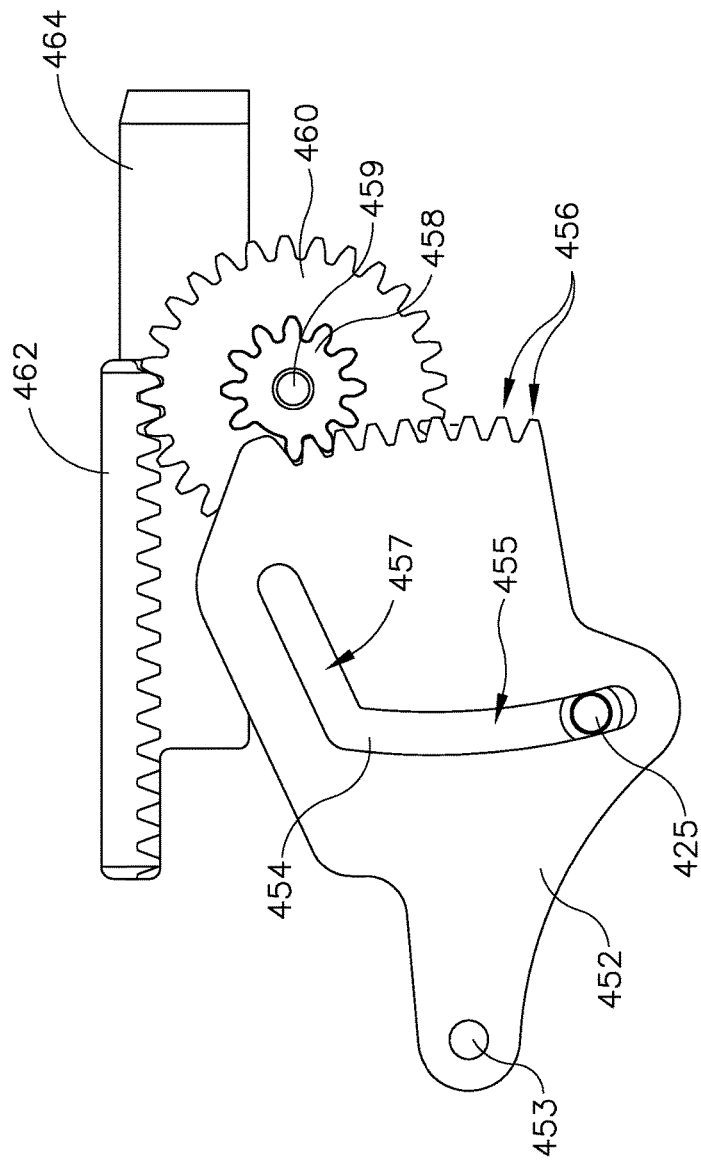
FIG. 27 depicts a side elevational view of the firing beam actuation assembly of FIG. 24A with the firing beam actuation assembly in an initial position.
Figure 28:
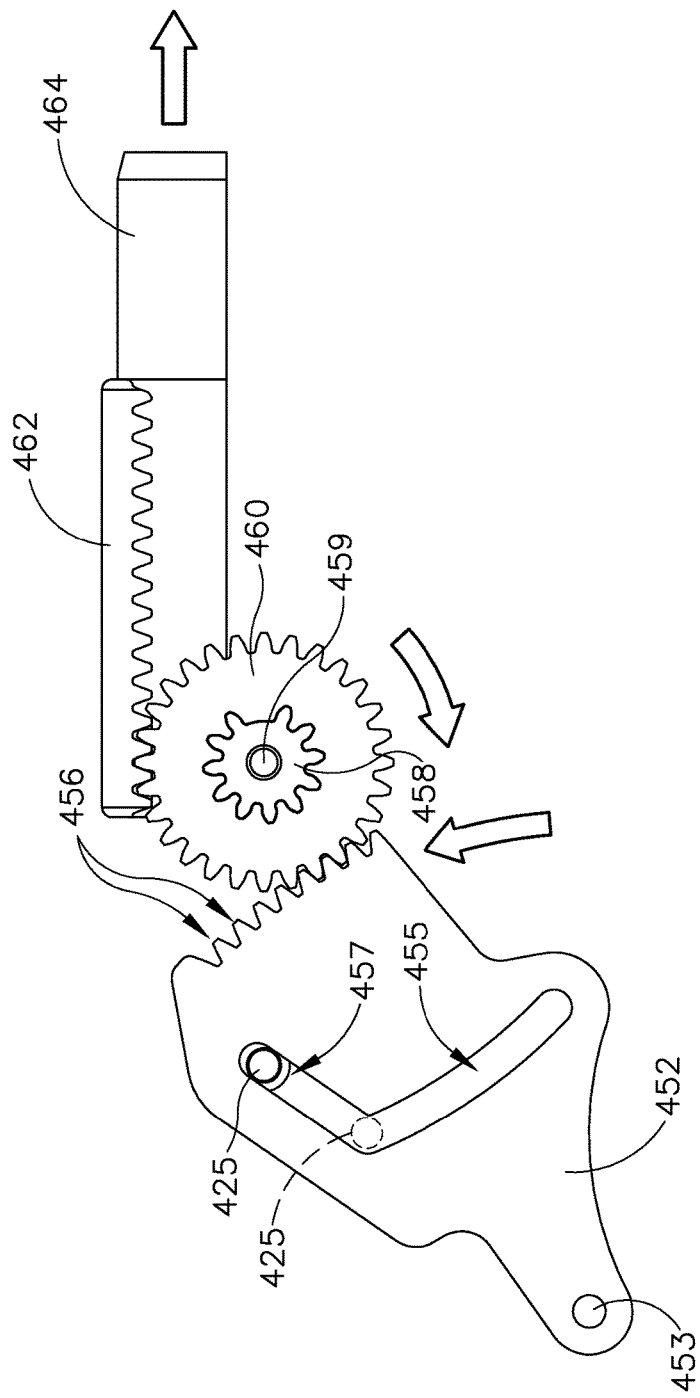
FIG. 28 depicts a side elevational view of the firing beam actuation assembly of FIG. 24A with the firing beam actuation assembly in an actuated position.

FIGS. 27 and 28 show firing beam actuation assembly (450) isolated from the rest of electrosurgical instrument (410). As can be seen, firing beam actuation assembly (450) is similar to firing beam actuation assembly (250) described above. Firing beam actuation assembly (450) comprises a pivotable drive plate (452), a sector gear (458), a pinion (460), and a rack (462). Drive plate (452) pivots about pivot pin (453), which is secured at a fixed location within handpiece (420). Drive plate (452) comprises a drive channel (454) and a plurality of teeth (456). Teeth (456) of drive plate (452) mesh with sector gear (458) such that as drive plate (452) pivots about pivot pin (453) in response to movement of trigger pin (425) as described below, sector gear (458) is driven in a clockwise rotational direction. Sector gear (458) is secured to pinion (460) by pin (459). Sector gear (458) and pinion (460) are secured such that rotation of sector gear (458) correspondingly rotates pinion (460). In other words, clockwise movement of sector gear (458) in turn rotates pinion (460) through a corresponding angular distance in the clockwise direction.

Pinion (460) meshes with rack (462) such that rotational movement of pinion (460) is converted into translation of rack (462). In particular, clockwise motion of pinion (460) then correspondingly drives rack (462) in the distal direction. Rack (462) includes an attachment portion (464), which attaches to a firing shaft (not shown). A firing beam is secured to the firing shaft, such that translation of firing shaft provides translation of the firing beam. The firing beam and the firing shaft translate unitarily with rack (462). It should therefore be understood that pivotal motion of drive plate (452) provides longitudinal translation of the firing beam. The firing beam may thus be operable to cut through tissue that is captured between jaws (442, 444).

Drive channel (454) of drive plate (452) has a first leg (455) and a second leg (457), which together define an "L" shape. A first trigger pin (425) is slidably disposed in drive channel (454). Trigger pin (425) is fixedly secured to trigger (424) such that trigger pin (425) rotates unitarily with trigger (424) through the first and second ranges of motion described herein. It should be understood that trigger pin (425) is positioned laterally outboard of the components of jaw actuation assembly (470) such that trigger pin (425) does not contact any components of jaw actuation assembly (470) during the movement of trigger pin (425). The "L" shape of drive channel (454) is configured such that trigger pin (425) moves through first leg (455) of channel (454) as trigger (424) is pivoted toward pistol grip (422) through the first range of motion (i.e., the range of motion that provides actuation of jaw actuation assembly (470)); and such that trigger pin (425) moves through second leg (457) of channel (454) as trigger (424) is pivoted toward pistol grip (422) through a second range of motion.

FIG. 28 shows the position of first trigger pin (425) in phantom upon completion of the first range of pivotal motion by trigger (424). FIG. 28 shows the position of first trigger pin (425) in solid lines upon completion of the second range of pivotal motion by trigger (424). It should be understood that the first range of motion of trigger (424) provides closure of jaws (442, 444) as described above. It should also be understood that drive plate (452) remains stationary as trigger pin (425) moves through first leg (455) of channel (454); and drive plate (452) pivots about pivot pin (453) as trigger pin (425) moves through second leg (457) of channel (454).

An exemplary mode of operation of firing beam actuation assembly (450) can be seen by comparing FIGS. 27 and 28. In particular, firing beam actuation assembly (450) is initially in the position shown in FIG. 27. An operator may actuate trigger (424) through the first range of motion as described above to actuate jaw actuation assembly (470), thereby capturing and compressing tissue between jaws (442, 444). The operator may continue to actuate trigger (424) through a second range of motion toward pistol grip (422) to actuate firing beam actuation assembly (450). It should be understood that because trigger (424) is a two stage trigger, the operator may stop short in the pivotal movement of trigger (424) at the completion of the first range of motion, such that the operator does not distally advance the firing beam. As can be seen by the phantom representation of trigger pin (425) in FIG. 28, trigger pin (425) has just traversed the first leg (455) of the L-shaped drive channel (454), such that drive plate (452) has not yet pivoted about pin (453). The firing beam has thus remained longitudinally stationary as trigger (424) pivots through the first range of motion toward pistol grip (422).

In some exemplary modes of operation, an operator may grasp tissue by pivoting trigger (424) toward pistol grip (422) through the first range of motion to grasp tissue between jaws (442, 444), actuate button (426) to activate RF energy to seal the tissue grasped between jaws (442, 444), and then pivot trigger (424) toward pistol grip (422) through a second range of motion to cut the tissue with the firing beam. FIG. 28 shows the position of first trigger pin (425) in solid lines in L-shaped drive channel (454) upon completion of the second range of motion. In some other exemplary modes of operation, an operator may pivot trigger (424) through the first and second ranges of motion to grasp and cut tissue between jaws (442, 444); then actuate button (426) to activate RF energy to seal the tissue. In still other exemplary modes of operation, the operator may simply pivot trigger (424) through the first range of motion toward pistol grip (422) to simply grasp tissue by transitioning driving jaw (444) to the closed position; then release trigger (424) to return trigger (424) back to the position shown in FIG. 23, thereby driving jaw (444) back to the open position to release the tissue from end effector (440).

It should be understood that although not discussed herein, firing beam actuation assembly (450) and/or jaw actuation assembly (470) may include other features discussed above such as springs to resiliently bias said assemblies (450, 470). Of course, in other examples, the various components of firing beam actuation assembly (450) and/or jaw actuation assembly (470) may incorporate other elements of similar assemblies discussed above as will be apparent to those of ordinary skill in the art in view of the teachings herein.

FIGS. 29 and 30 show jaw sensor assembly (490) and a portion of jaw actuation assembly (470) in isolation from the rest of electrosurgical instrument (410). Jaw sensor assembly (490) comprises a lever arm (492) and a sensor assembly (504). Lever arm (492) includes an elongate distal portion (494) and a pivot feature (496). Elongate distal portion (494) is configured to actuate jaw sensor (506) as will be described in further detail below. Elongate distal portion (494) extends proximally from sensor assembly (504) for a certain distance to create a mechanical advantage such that relatively small movements of jaw shaft (487) are converted into relatively large movements of elongate distal portion (494). Of course, elongate distal portion (494) may be of any suitable length as will be apparent to those of ordinary skill in the art in view of the teachings herein.

Pivot feature (496) pivots elongate distal portion (494) up and down in response to movements of jaw shaft (487). In particular, pivot feature (496) includes an engagement tooth (498), which is configured to engage with an annular flange (499) of jaw shaft (487). As will be described in greater detail below, annular flange (499) is fixedly secured to jaw shaft (487) such that proximal translation of jaw shaft (487) correspondingly translates annular flange (499) toward engagement tooth (498). Pivot feature (496) pivots about a lever arm pin (500), which is rotatably secured to handpiece (420) such that pivot feature (496) is operable to pivot lever arm (492) relative to handpiece (420). Pivot feature (496) is also shown as being equipped with a spring (502) to resiliently bias elongate distal portion (494) upwardly relative to jaw sensor (506). Of course, in other examples, any other suitable structure may be used to resiliently bias elongate distal portion (494) upwardly as will be apparent to those of ordinary skill in the art in view of the teachings herein.

Sensor assembly (504) comprises a jaw sensor (506) and jaw sensor circuitry (510). Jaw sensor (506) is similar to jaw sensors (146, 308) described above insofar as jaw sensor (506) is a binary switch that includes a resiliently biased movable protrusion (508). Of course, in other examples jaw sensor (506) may comprise any other suitable kind of sensor such as a reed switch, hall effect sensor, capacitive sensor, rheostat, or any other suitable sensor as will be apparent to those of ordinary skill in the art in view of the teachings herein.

Jaw sensor circuitry (510) is operable to convert electronic changes in the state of jaw sensor (506) into signals that may be received by a controller (not shown) such as controller (82). By way of example only, jaw sensor circuitry (510) may comprise resistors, transistors, integrated circuits and/or other electronic circuitry. As will be described in greater detail below, jaw sensor circuitry (510) may communicate a signal to controller (82) that may allow controller (82) to identify whether end effector (440) is open or closed. Moreover, jaw sensor circuitry (510) may communicate a signal to controller (82) that may allow controller (82) to determine the degree to which end effector (440) is closed.

An exemplary mode of operation of jaw sensor assembly (490) can be seen by comparing FIGS. 29 and 30. In particular, jaw sensor assembly (490) may initially be in the position shown in FIG. 29. In this position, jaw shaft (487) and drive block (484) of jaw actuation assembly (470) are in their distal most position such that jaw (444) is in the open position. Likewise, lever arm (492) is resiliently biased upwardly such that jaw sensor (506) is in a state that similarly corresponds to the open position of jaw (444). When the sequence to close end effector (440) is initiated, jaw shaft (487) and drive block (484) of jaw actuation assembly (470) translate proximally relative to handpiece (420) as described above. As jaw (444) approaches the closed position, annular flange (499) engages engagement tooth (498) of pivot feature (496) such that lever arm (492) begins to pivot about pin (500) relative to handpiece (420). Lever arm (492) will continue to pivot about pin (500) until jaw (444) reaches the closed position. As similarly described above, the closed position of jaw (444) corresponds to a certain predetermined gap (or angular separation) between jaws (442, 444). Elongate distal portion (494) is configured to actuate movable protrusion (508) of jaw sensor (506) when the predetermined gap (or angular separation) between first jaw (442) and second jaw (444) is reached. Accordingly, jaw sensor (506) is configured to communicate when end effector (440) is closed to controller (82) via jaw sensor circuitry (510). Controller (82) may then be responsive to the signal from jaw sensor circuitry (510) to adjust the RF energy delivered to end effector (440) to effectively seal tissue grasped by end effector (440).

Controller (82) may be configured to respond to changes in state of jaw sensor (504) communicated to controller (82) by jaw sensor circuitry (510). In particular, when controller (82) receives a signal from jaw sensor (504) corresponding to the closed position of second jaw (444), controller (82) may be converted into a ready state where subsequent activation of button (426) provides RF energy to jaws (442, 444). Conversely, if button (426) is activated before jaw sensor (504) indicates a sufficiently closed position of jaw (444), controller (82) may be prevented from providing RF energy to jaws (442, 444). In addition or in the alternative, controller (82) may activate a user feedback feature (e.g., audible tone, visible light, etc.) to alert the operator that jaw (444) is insufficiently closed if the operator activates button (426) before jaw sensor (504) indicates a sufficiently closed position of jaw (444). In addition to or as an alternative to the foregoing, jaw sensor (504) may be configured to detect closure of jaws (442, 444) in the absence of tissue between jaws (442, 444). In other words, sensor (446) and controller (82) may be operable to determine that jaws (442, 444) have been closed without tissue being positioned between jaws (442, 444). In such instances, controller (82) may prevent the delivery of RF energy to jaws (442, 444). In addition or in the alternative, controller (82) may activate a user feedback feature (e.g., audible tone, visible light, etc.) to alert the operator that end effector (440) needs to be repositioned in order to position tissue between jaws (442, 444) before jaws (442, 444) may deliver RF energy.

It should be understood that the pivotal movement of lever arm (492) is proportional to the pivotal movement of jaw (444). Although jaw sensor (504) is described herein as being binary in nature, it should be understood that in other examples jaw sensor (504) may be non-binary having a plurality of outputs to communicate different amount of closure of second jaw (444). In such examples, controller (82) may be responsive to varying degrees of input from jaw sensor (504) indicating differing amounts of closure of second jaw (444) such that RF power may be altered depending on different amounts of closure of second jaw (444). For instance, if jaw sensor (504) indicates a relatively wide separation of jaw (444) from jaw (442) when button (426) is activated (e.g., indicating a relatively thick bundle of tissue), controller (82) may provide a relatively high level of RF energy to jaws (442, 444). If jaw sensor (504) indicates a relatively small separation of jaw (444) from jaw (442) when button (426) is activated (e.g., indicating a relatively thin bundle of tissue), controller (82) may provide a relatively low level of RF energy to jaws (442, 444). It should also be understood that controller may (82) provide a control algorithm that factors in feedback from jaw sensor (504) and feedback indicating an electrical resistance of tissue in jaws (442, 444). Various suitable ways in which the electrical resistance of tissue may be sensed will be apparent to those of ordinary skill in the art in view of the teachings herein. Of course, controller (82) may be responsive to jaw sensor (504) and/or other sources of feedback in any other suitable way as will be apparent to those of ordinary skill in the art in view of the teachings herein.

It should also be understood that jaw sensor (504) may be adjustable like jaw sensor (308) described above, such that the sensitivity of sensor (504) may be adjusted to select a desired predetermined gap (or angular separation) between jaws (442, 444).

C. Exemplary Electrosurgical Instrument with Jaw Sensor Activated by Rotary Member FIG. 31-34 show an exemplary electrosurgical instrument (610) with a rotational rheostat (692) integrated into a jaw actuation assembly (690). Except as otherwise described below, electrosurgical instrument (610) is substantially the same as electrosurgical instrument (410) described above. Electrosurgical instrument (610) of the present example includes a handpiece (620), a shaft (630) extending distally from handpiece (620), and end effector (640) disposed at a distal end of shaft (630). Handpiece (620) of the present example includes a pistol grip (622), pivoting trigger (624), and an activation button (626). Trigger (624) is pivotable toward and away from pistol grip (622) to selectively actuate end effector (640). Activation button (626) is operable to selectively activate RF circuitry that is in communication with end effector (640).

Shaft (630) of the present example includes a rigid outer sheath (632) without an articulation section, though it should be understood that some variations may include an articulation section. Shaft (630) is rotatable about the longitudinal axis defined by sheath (632), relative to handpiece (620), via a knob (634). Such rotation may provide rotation of end effector (640) and shaft (630) unitarily.

End effector (640) is similar to end effector (440) described above. Like end effector (440), end effector (640)

comprises a first jaw (642) and a second jaw (644). First jaw (642) is fixed relative to shaft (630) such that first jaw (642) remains stationary as end effector (640) actuates. Second jaw (644) is pivotable relative to first jaw (642) such that second jaw (644) transitions between an open and closed position as end effector (640) is actuated. Second jaw (644) may be pivoted in any suitable way as will be apparent to those of ordinary skill in the art in view of the teachings herein. Instrument (610) further includes a firing beam (not shown) that is operable to translate through end effector (640) to thereby sever tissue captured between jaws (642, 644). By way of example only, such a firing beam may be configured similar to firing beam (60), similar to firing beam (70), or in any other suitable fashion.

Figure 32:
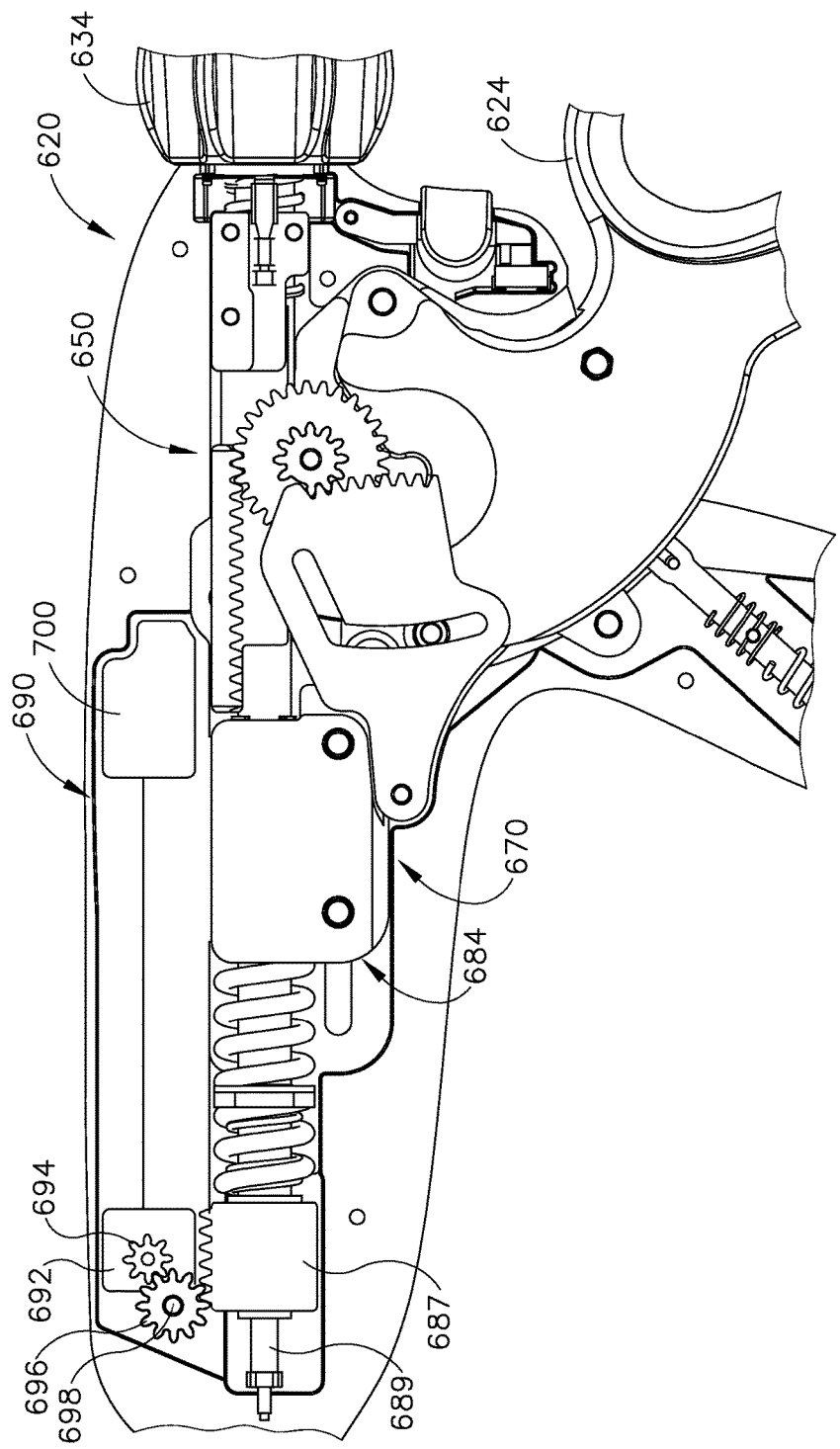
FIG. 32 depicts a detailed side elevational view of the instrument of FIG. 31 with one side of a handpiece removed showing a jaw actuation assembly, a firing beam actuation assembly, and a sensor assembly.

FIG. 32 shows a side view of electrosurgical instrument (610) with half of handpiece (620) removed. As can be seen, the inside of handpiece (620) comprises a firing beam actuation assembly (650), a jaw actuation assembly (670), and a jaw sensor assembly (690). Generally, firing beam actuation assembly (650) and jaw actuation assembly (670) are substantially the same as firing beam actuation assembly (450) and jaw actuation assembly (470). For instance, jaw actuation assembly (670) of the present example comprises a drive block (684) that is coupled with trigger (624). As trigger (624) is pivoted, drive block (684) will immediately or eventually translate jaw a shaft (689). Jaw shaft (689) of this example is analogous to jaw shafts (282, 487) described above. Due to the overlap in similarities between assemblies (650, 670) and assemblies (450, 470), the remaining particulars of each assembly (650, 670) will not be discussed herein. However, specific instances where assemblies (650, 670) depart from assemblies (450, 470) will be noted specifically below.

Figure 33:
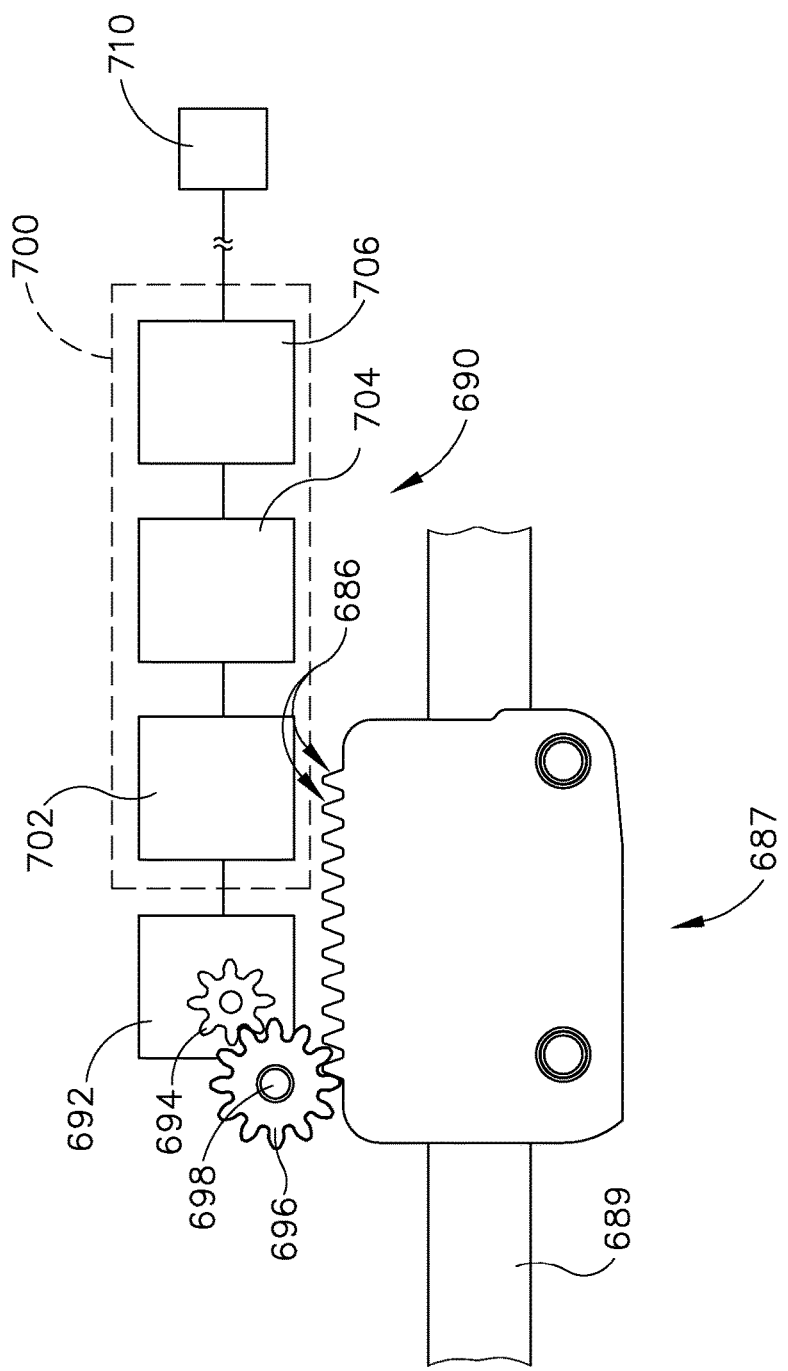
FIG. 33 depicts a side elevational view of the sensor assembly of FIG. 32, the sensor assembly providing a first resistance with the jaw actuation assembly in an initial position.
Figure 34:
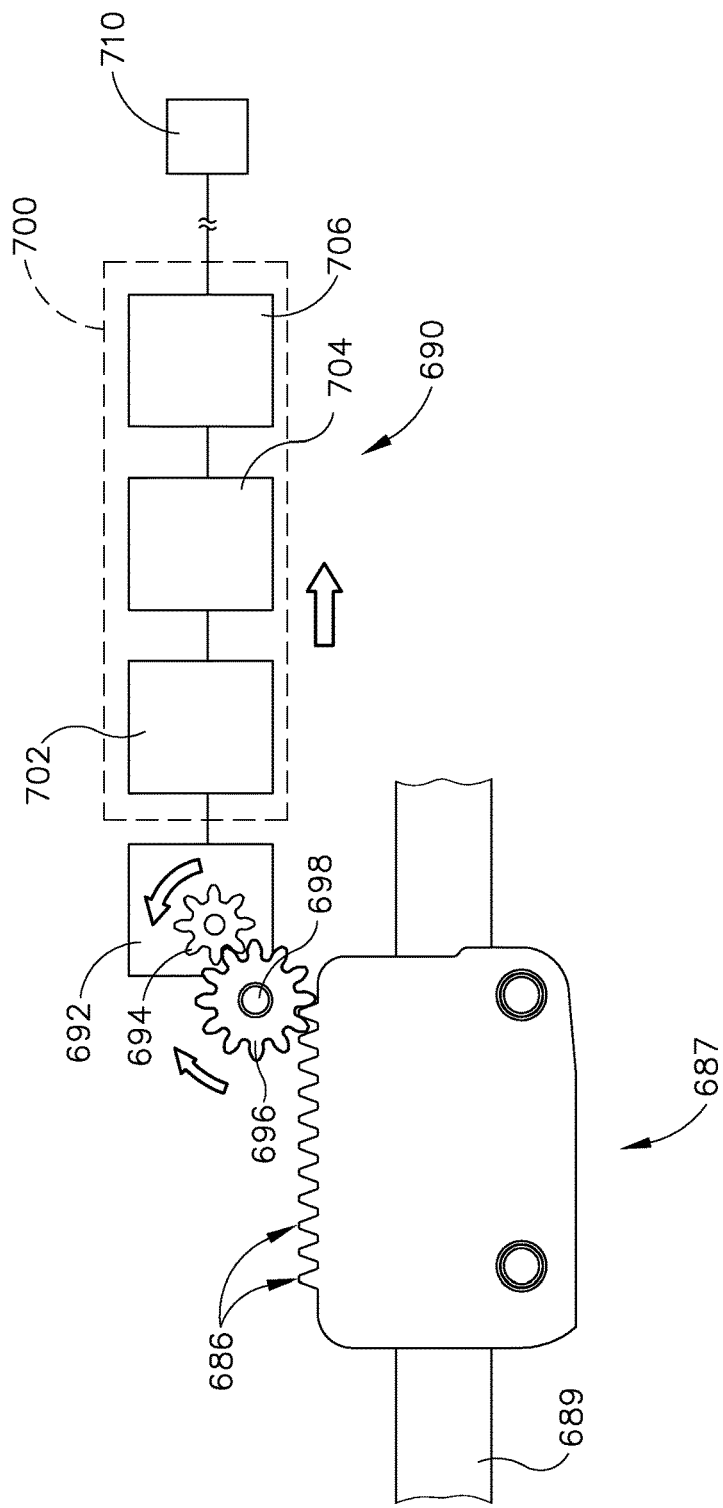
FIG. 34 depicts a side elevational view of the sensor assembly of FIG. 32, the sensor assembly providing a second resistance with the jaw actuation assembly in an actuated position.

FIGS. 33-34 show jaw sensor assembly (690) and a portion of jaw actuation assembly (670) in isolation from the rest of electrosurgical instrument (610). It should be understood that at least a portion of jaw sensor assembly (690) is shown schematically in FIGS. 33-34. As can be seen in FIG. 33, jaw sensor assembly (690) comprises a rotational rheostat (692), and jaw sensor circuitry (700). Rotational rheostat (692) is used in electrosurgical instrument (610) like jaw sensors (146, 308, 506) described above. However, unlike jaw sensors (146, 308, 506), rotational rheostat (692) does not have a binary signal output. Similar to rheostats that are known in the art, rotational rheostat (692) acts as a variable resistor such that as rotational rheostat (692) rotates, the resistance of rotational rheostat (692) is changed. Rotational rheostat (692) comprises a rheostat gear (694) which is configured to mesh with a drive gear (696). Drive gear (696) is attached to a rotatably secured gear pin (698), which permits drive gear (696) to rotate relative to handpiece (620). Rheostat gear (694) is smaller relative to drive gear (696) such that a mechanical advantage is created to convert relatively small movements of drive gear (696) into relatively large movements of rheostat gear (694).

A sensor rack (687) is unitarily secured to jaw shaft (689) in this example, such that sensor rack (687) translates longitudinally as jaws (642, 644) transition between open and closed positions. Sensor rack (687) includes a set of integral rack teeth (686). Drive gear (696) meshes with rack teeth (686) of sensor rack (687). Thus, it should be understood that longitudinal motion of sensor rack (687) provides concomitant rotation of drive gear (696).

Jaw sensor circuitry (700) is configured to convert electrical energy from rotational rheostat (692) into a signal that may be received by a controller (710). The individual components of jaw sensor circuitry (700) are shown schematically in FIGS. 33-34. In the present example, jaw sensor circuitry (700) includes an integrated circuit (IC) chip (702), a transistor (704), and a resistor (706). IC chip (702) is in communication with rotational rheostat (692) and transistor (704). IC chip (702) is configured to activate transistor (704) when IC chip (702) detects that rotational rheostat (692) reaches a certain predetermined resistance as will be described in greater detail below. Transistor (704) is in communication with IC chip (702), resistor (706), and controller (710). Transistor (704) is configured to pass a signal through resistor (706) to controller (710) when transistor (704) is activated by IC chip (702). Such a signal may indicate to controller (710) whether end effector (640) is in an open or closed state as will be described in further detail below. Other suitable components and arrangements that may be provided in jaw sensor circuitry (700) will be apparent to those of ordinary skill in the art in view of the teachings herein.

An exemplary mode of operation of jaw sensor assembly (690) can be seen by comparing FIGS. 33 and 34. In particular, FIG. 33 shows jaw sensor assembly (690) in an initial position. In the initial position, sensor rack (687) is positioned distally relative to jaw sensor assembly (690). It should be understood that the distal position of sensor rack (687) corresponds to jaw (644) in the open position, such that end effector (640) is in an open state. As end effector (640) is closed via trigger (624), sensor rack (687) will translate proximally. Proximal translation of sensor rack (687) will be converted into rotational motion of drive gear (696), which is communicated to rheostat gear (694) by engagement between drive gear (696) and rheostat gear (694). As rheostat gear (694) rotates, the resistance level of rotational rheostat (692) will change. Thus, the resistance of rotational rheostat (692) is proportional to the position of second jaw (644) of end effector (640) as end effector (640) transitions from the open state to the closed state.

Once end effector (640) is in the closed state, a certain gap (or angular separation) will be formed between first jaw (642) and second jaw (644). Because the resistance of rotational rheostat (692) is proportional to the position of second jaw (644), a certain resistance value of rotational rheostat (692) can be determined. This resistance value corresponds to the gap (or angular separation) formed between first jaw (642) and second jaw (644). This resistance value of rotational rheostat (692) may be programmed into IC chip (702) such that IC chip (702) may activate transistor (704) once the predetermined resistance value is reached. Activated transistor (704) may then communicate a signal to controller (710) to indicate that end effector (640) is closed. When controller (710) identifies that end effector (640) is in the closed state, controller (710) may modify the RF energy delivered to end effector (640) to ensure adequate sealing of tissue grasped by end effector (640).

Controller (710) may be configured to respond to changes in state of jaw sensor assembly (690) communicated to controller (710). In particular, when controller (710) receives a signal from jaw sensor assembly (690) corresponding to the closed position of second jaw (644), controller (710) may be converted into a ready state where subsequent activation of button (626) provides RF energy to jaws (642, 644). Conversely, if button (626) is activated before jaw sensor assembly (690) indicates a sufficiently closed position of jaw (644), controller (710) may be prevented from providing RF energy to jaws (642, 644). In addition or in the alternative, controller (710) may activate a user feedback feature (e.g., audible tone, visible light, etc.) to alert the operator that jaw (644) is insufficiently closed if the operator activates button (626) before jaw sensor assembly (690) indicates a sufficiently closed position of jaw (644). In addition to or as an alternative to the foregoing, jaw sensor assembly (690) may be configured to detect closure of jaws (642, 644) in the absence of tissue between jaws (642, 644) (or closure where jaws (642, 644) are otherwise separated by a gap that is less than a threshold thickness). In other words, jaw sensor assembly (690) and controller (710) may be operable to determine that jaws (642, 644) have been closed without tissue being positioned between jaws (642, 644) (or closure where jaws (642, 644) are otherwise separated by a gap that is less than a threshold thickness). In such instances, controller (710) may prevent the delivery of RF energy to jaws (642, 644) to prevent a short circuit from occurring between electrodes of jaws (642, 644). In addition or in the alternative, controller (710) may activate a user feedback feature (e.g., audible tone, visible light, etc.) to alert the operator that end effector (640) needs to be repositioned in order to position tissue between jaws (642, 644) before jaws (642, 644) may deliver RF energy.

Since rheostat (692) is operable to provide variable resistance throughout a particular range, such resistance may vary in direct proportion to the degree of closure of second jaw (644). Thus, controller (710) may be responsive to varying degrees of input from jaw sensor assembly (690) indicating differing amounts of closure of second jaw (644) such that RF power may be altered depending on different amounts of closure of second jaw (644). For instance, if jaw sensor assembly (690) indicates a relatively wide separation of jaw (644) from jaw (642) when button (626) is activated (e.g., indicating a relatively thick bundle of tissue), controller (710) may provide a relatively high level of RF energy to jaws (642, 644). If jaw sensor assembly (690) indicates a relatively small separation of jaw (644) from jaw (642) when button (626) is activated (e.g., indicating a relatively thin bundle of tissue), controller (710) may provide a relatively low level of RF energy to jaws (642, 644). If jaw sensor assembly (690) indicates a jaw separation that is below a minimum threshold, controller (710) may terminate or prevent energy application to prevent a short circuit from occurring between electrodes of jaws (642, 644). It should also be understood that controller may (710) provide a control algorithm that factors in feedback from jaw sensor assembly (690) and feedback indicating an electrical resistance of tissue in jaws (642, 644). Various suitable ways in which the electrical resistance of tissue may be sensed will be apparent to those of ordinary skill in the art in view of the teachings herein. Of course, controller (710) may be responsive to jaw sensor assembly (690) and/or other sources of feedback in any other suitable way as will be apparent to those of ordinary skill in the art in view of the teachings herein.

Similarly, IC chip (702) may include additional functionality to identify different resistances of rotational rheostat (692). For instance, it may be desirable to different gaps between first jaw (642) and second jaw (644) such as for procedures where end effector (640) is used for sealing tissue of varying thicknesses. In such circumstances, an operator may select different modes (e.g., modes for thick or thin tissue) that may correspond to different jaw (642, 644) gap sizes, and IC chip (702) may accordingly identify different resistance levels that correspond to such different jaw (642, 644) gap sizes. In other examples, electrosurgical instrument (610) may change over time such that a resistance that once corresponded to a certain gap between jaws (642, 644), no longer corresponds to the certain gap. In such examples, IC chip (702) may be reprogrammed to essentially recalibrate electrosurgical instrument (610). In addition or in the alternative, IC chip (702) may be reprogrammed such that the specific resistance identified by IC chip (702) is altered to change sealing characteristics to suit user preferences. Still in other examples, IC chip (702) may be reprogrammed in any suitable way as will be apparent to those of ordinary skill in the art in view of the teachings herein.

IV. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source and/or controller instead of requiring the device to be plugged into an external power source and/or controller by a cable. Various examples of how medical devices may be adapted to include a portable power source and/or controller are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

In versions where the teachings herein are applied to a surgical stapling instrument, it should be understood that the teachings herein may be combined with the teachings of one or more of the following, the disclosures of all of which are incorporated by reference herein: U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, now U.S. Pat. No. 8,408,439, issued Apr. 2, 2013; and U.S. Pub. No. 2012/0239012, entitled "Motor-Driven Surgical Cutting Instrument with Electric Actuator Directional Control Assembly," published Sep. 20, 2012, now U.S. Pat. No. 8,453,914, issued Jun. 4, 2013. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, now abandoned, the disclosure of which is incorporated by reference herein; U.S. Pat. Pub. No. 2007/0191713, entitled "Ultrasonic Device for Cutting and Coagulating," published Aug. 16, 2007, now abandoned, the disclosure of which is incorporated by reference herein; U.S. Pat. Pub. No. 2007/0282333, entitled "Ultrasonic Waveguide and Blade," published Dec. 6, 2007, now abandoned, the disclosure of which is incorporated by reference herein; U.S. Pat. Pub. No. 2008/0200940, entitled "Ultrasonic Device for Cutting and Coagulating," published Aug. 21, 2008, now abandoned, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) a body;
   (b) a shaft extending distally from the body;
   (c) an end effector configured to receive energy from an energy source, wherein the end effector comprises:
      (i) a first jaw, and
      (ii) a second jaw, wherein the second jaw is pivotable relative to the first jaw to transition the end effector from an open configuration to a closed configuration, wherein the first jaw and second jaw define a closure gap between each other when the end effector is in the closed configuration;
   (d) a first movable member operatively coupled with the second jaw, wherein the first movable member is configured to move in response to pivoting of the second jaw relative to the first jaw; and
   (e) a sensor, wherein the sensor includes a second movable member configured to be engaged by the first movable member, wherein the second movable member is moveable from a first position to a second position in response to movement of the first moveable member when the end effector transitions from the open configuration to the closed configuration, wherein the sensor is operable to detect that the end effector is in the closed configuration when the second movable member moves to the second position, wherein the sensor is in communication with the energy source, wherein the sensor is operable to communicate a signal to the energy source when the sensor detects the end effector in the closed configuration.

2. The apparatus of claim 1, wherein the sensor is positioned within the body.

3. The apparatus of claim 2, wherein the sensor is associated with an end effector actuation assembly, wherein the sensor is positioned to be actuated by motion of the end effector actuation assembly.

4. The apparatus of claim 1, wherein the sensor is positioned within the end effector.

5. The apparatus of claim 4, wherein the sensor is positioned within the end effector adjacent to at least a portion of the second jaw such that the sensor is positioned to be actuated when the second jaw is pivoted to a position corresponding to the closed configuration of the end effector.

6. The apparatus of claim 1, further comprising:
   (a) a sensor actuation assembly, wherein the sensor actuation assembly includes the first movable member and is operable to activate the sensor; and
   (b) an end effector actuation assembly, wherein the end effector actuation assembly is operable to transition the end effector between the open configuration and the closed configuration,
   wherein the sensor actuation assembly is in communication with both the sensor and the end effector actuation assembly.

7. The apparatus of claim 6, wherein the first moveable member is configured to mechanically amplify motion of the end effector actuation assembly.

8. The apparatus of claim 7, wherein the first moveable member comprises at least one of a lever arm or a gear.

9. The apparatus of claim 1, wherein the sensor comprises a switch operable to transition between an open state and a closed state.

10. The apparatus of claim 1, wherein the sensor comprises a hall effect sensor.

11. The apparatus of claim 1, wherein the sensor comprises a rheostat.

12. The apparatus of claim 11, wherein the rheostat comprises a rotatable rheostat driven by a rack and pinion assembly.

13. The apparatus of claim 11, further comprising an integrated circuit, wherein the rheostat is in communication with the end effector such that the resistance of the rheostat is proportional to an angular position of the second jaw, wherein the integrated circuit is configured to identify a position of the second jaw relative to the first jaw based on the resistance of the rheostat.

14. The apparatus of claim 1, wherein the sensor is operable to communicate a signal to the energy source indicating one of the following:
   (i) a ready state enabling delivery of RF energy to the first and second jaws, or
   (ii) a non-ready state preventing delivery of RF energy to the first and second jaws.

15. The apparatus of claim 1, wherein the sensor is operable to communicate a signal to the energy source that is operable to alter delivery of RF energy to the first and second jaws in response to a change of position of the second jaw relative to the first jaw.

16. An apparatus for operating on tissue, the apparatus comprising:
   (a) a body;
   (b) a shaft extending distally from the body;
   (c) an end effector configured to receive energy from an energy source, wherein the end effector comprises:
      (i) a first jaw, and (ii) a second jaw, wherein the second jaw is pivotable relative to the first jaw to transition the end effector from an open configuration to a closed configuration, wherein the first jaw and second jaw define a closure gap between each other when the end effector is in the closed configuration; and (d) a sensor assembly, wherein the sensor assembly comprises:
  (i) a sensor having a first moveable member, and
  (ii) a sensor actuator associated with the second jaw, wherein the sensor actuator includes a second movable member, wherein the second moveable member is operatively coupled with the second jaw and is positioned to engage the first moveable member, wherein the second moveable member is configured to actuate the first moveable member when the end effector transitions from the open configuration to the closed configuration, wherein the sensor is operable to detect that the end effector is in the closed configuration when the first movable member is actuated by the second moveable member, wherein the second movable member is configured to mechanically amplify motion associated with a transition of the end effector from the open configuration to the closed configuration, wherein the second movable member is configured to actuate the first moveable member through the mechanically amplified motion.

17. The apparatus of claim 16, wherein the sensor assembly further comprises an adjustment assembly, wherein the adjustment assembly is configured to adjust the point at which the second moveable member of the sensor actuator actuates the sensor.

18. The apparatus of claim 17, wherein the adjustment assembly comprises a lead screw with threading, wherein the sensor includes a bore having internal threading corresponding to the threading of the lead screw, wherein the position of the sensor is adjustable by rotating the lead screw.

19. The apparatus of claim 18, further comprising a locking assembly operable to selectively prevent rotation of the lead screw.

20. A method for operating on tissue using an electrosurgical instrument, wherein the electrosurgical instrument comprises a body, a shaft extending from the body, an end effector, a sensor, a lever arm, and a controller, the method comprising:
  (a) actuating the end effector from an open position to a closed position to grasp at least some tissue between a first jaw and a second jaw of the end effector;
  (b) pivoting the lever arm about a pivot axis so that an end portion of the lever arm engages the sensor as the end effector moves from the open position to the closed position;
  (c) sensing with the sensor a gap between the first jaw and the second jaw in response to engagement of the lever arm with the sensor;
  (d) communicating a signal to the controller from the sensor based on the sensed gap;
  (e) based on the signal, determining that the sensed gap is less than or equal to a maximum allowable gap; and
  (f) based on the determination, activating electrodes of the first and second jaws to deliver RF energy to the grasped tissue.

* * * * *